US012545673B2

(12) United States Patent
Lee et al.

(10) Patent No.: US 12,545,673 B2
(45) Date of Patent: Feb. 10, 2026

(54) IMIDAZOPYRIDINE DERIVATIVE AND PHARMACEUTICAL COMPOSITION COMPRISING SAME AS ACTIVE INGREDIENT

(71) Applicant: TSD LIFE SCIENCES CO., LTD., Seoul (KR)

(72) Inventors: Jae Won Lee, Seoul (KR); Do Hyun Son, Namyangju-si (KR); Nam Sook Kang, Daejeon (KR); Sung Wook Choi, Daejeon (KR)

(73) Assignee: TSD LIFE SCIENCES CO., LTD., Seoul (KR)

( * ) Notice: Subject to any disclaimer, the term of this patent is extended or adjusted under 35 U.S.C. 154(b) by 941 days.

(21) Appl. No.: 17/637,000

(22) PCT Filed: Aug. 31, 2020

(86) PCT No.: PCT/KR2020/011663
§ 371 (c)(1),
(2) Date: Feb. 21, 2022

(87) PCT Pub. No.: WO2021/040502
PCT Pub. Date: Mar. 4, 2021

(65) Prior Publication Data

US 2022/0396575 A1 Dec. 15, 2022

(30) Foreign Application Priority Data

Aug. 30, 2019 (KR) ........................ 10-2019-0107013

(51) Int. Cl.

| | |
|---|---|
| ***C07D 471/04*** | (2006.01) |
| ***A61P 1/00*** | (2006.01) |
| ***A61P 1/16*** | (2006.01) |
| ***A61P 25/28*** | (2006.01) |
| ***A61P 31/16*** | (2006.01) |
| ***A61P 35/00*** | (2006.01) |
| ***A61P 35/02*** | (2006.01) |

(52) U.S. Cl.
CPC .............. *C07D 471/04* (2013.01); *A61P 1/00* (2018.01); *A61P 1/16* (2018.01); *A61P 25/28* (2018.01); *A61P 31/16* (2018.01); *A61P 35/00* (2018.01); *A61P 35/02* (2018.01)

(58) Field of Classification Search
CPC .......... C07D 471/04; A61P 25/28; A61P 1/16; A61P 35/02; A61P 1/00; A61P 31/16; A61P 35/00
See application file for complete search history.

(56) References Cited

U.S. PATENT DOCUMENTS

| | | | |
|---|---|---|---|
| 2015/0218155 A1 | 8/2015 | Heinrich et al. | |
| 2016/0096834 A1 | 4/2016 | Gaillard et al. | |

FOREIGN PATENT DOCUMENTS

| | | | | |
|---|---|---|---|---|
| EA | 020578 B1 | 12/2014 | | |
| JP | 2012509903 A | 4/2012 | | |
| JP | 2014524451 A | 9/2014 | | |
| JP | 2017533897 A | 11/2017 | | |
| JP | 2018524350 A | 8/2018 | | |
| KR | 10-2011-0036602 A | 4/2011 | | |
| KR | 10-2015-0002639 A | 1/2015 | | |
| RU | 2487121 C2 | 7/2013 | | |
| WO | 2007056155 A1 | 5/2007 | | |
| WO | 2009012283 A1 | 1/2009 | | |
| WO | 2009029609 A1 | 3/2009 | | |
| WO | 2010068483 A2 | 6/2010 | | |
| WO | 2010148197 A1 | 12/2010 | | |
| WO | WO-2013116291 A1 * | 8/2013 | ........... | C07D 493/08 |
| WO | 2013147711 A1 | 10/2013 | | |
| WO | 2015092592 A1 | 6/2015 | | |

OTHER PUBLICATIONS

Armstrong, Folia Neuropathologica, 2013, 51, 3, 169-188 (Year: 2013).*
Blackadar, World Journal of Clinical Oncology, Feb. 10, 2016; 7(1): 54-86 (Year: 2016).*
Hassanpour, Journal of Cancer Research and Practice, 4, 2017, 127-129 (Year: 2017).*
Patel, Journal of Medicinal Chemistry, 2017, 60, 8083-8102 (Year: 2017).*
Younossi, Journal of Hepatology, 2019, vol. 70, pp. 531-544 (Year: 2019).*
Office Action issued in JP patent application serial No. 2022-513547 dated Feb. 14, 2023, with machine English machine translation.
Extended European Search Report issued in EP patent application serial No. 20857012.7 dated Jul. 17, 2023.
Xiao Ding et al., "Leucine-rich repeat kinase 2 inhibitors: a patent review (2014-present)", Expert Opinion on Therapeutic Patents, Feb. 18, 2020 (Feb. 18, 2020), pp. 1-12, XP055671253.
Gallo Kathleen et al., "Therapeutic potential of targeting mixed lineage kinases in cancer and inflammation", Pharmacology & Therapeutics, Elsevier, GB, vol. 207, Dec. 18, 2019 (Dec. 18, 2019), XP086060323.
International Search Report issued for PCT/KR2020/011663, dated Dec. 12, 2020.
Office Action issued in RU patent application serial No. 2022104041, dated Oct. 6, 2022, with machine English Translation.
Written Opinion of the International Searching Authority issued for PCT/KR2020/011663, dated Dec. 22, 2020, with English translation.

* cited by examiner

*Primary Examiner* — Andrew D Kosar
*Assistant Examiner* — Phillip Matthew Rzeczycki
(74) *Attorney, Agent, or Firm* — WESTMAN CHAMPLIN & KOEHLER, P.A.; Amanda M. Prose

(57) ABSTRACT

The present invention relates to an imidazopyridine derivative and a pharmaceutical composition comprising same as an active ingredient and, more particularly, to an imidazopyridine derivative that inhibits protein kinase activity and as such, can be used for preventing or treating cancer, neurodegenerative disease, non-alcoholic fatty liver disease, influenza, etc., and a pharmaceutical composition comprising same as an active ingredient.

4 Claims, 16 Drawing Sheets

Specification includes a Sequence Listing.

[Fig 1]
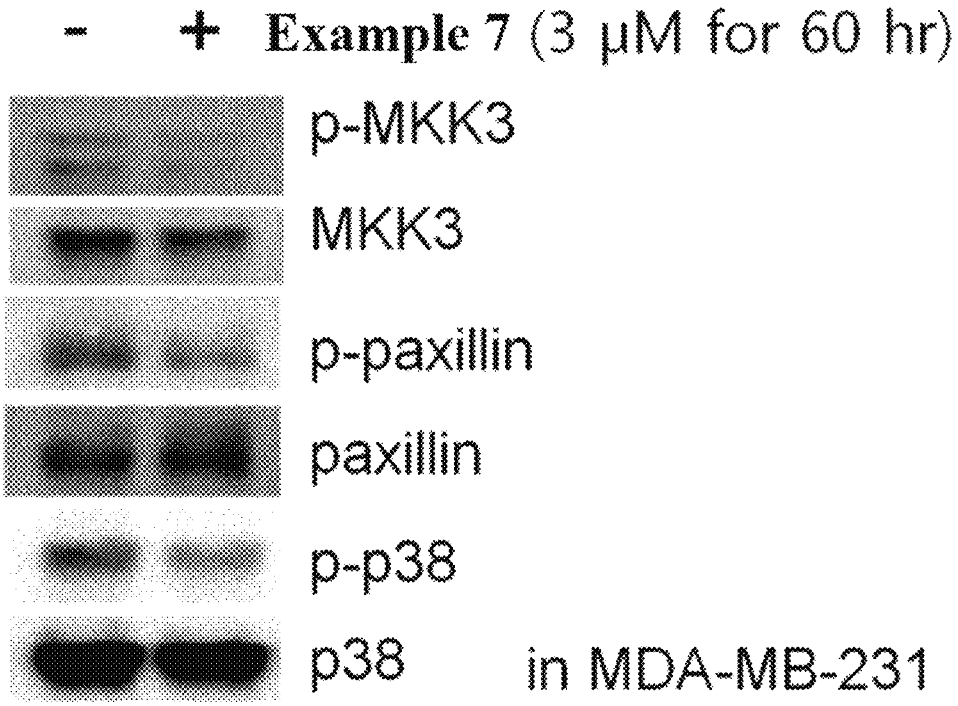

[Fig 2]
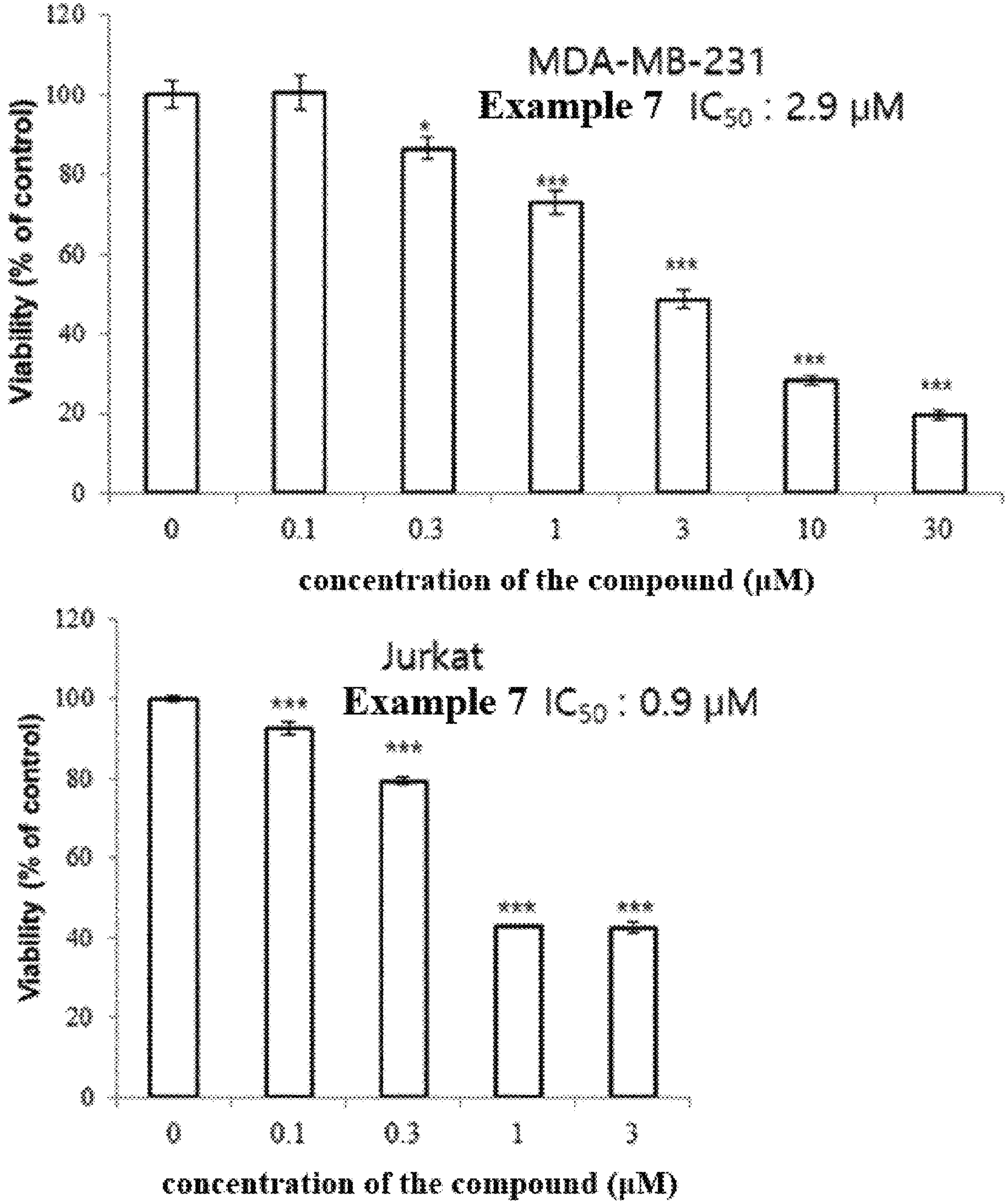

[Fig 3]
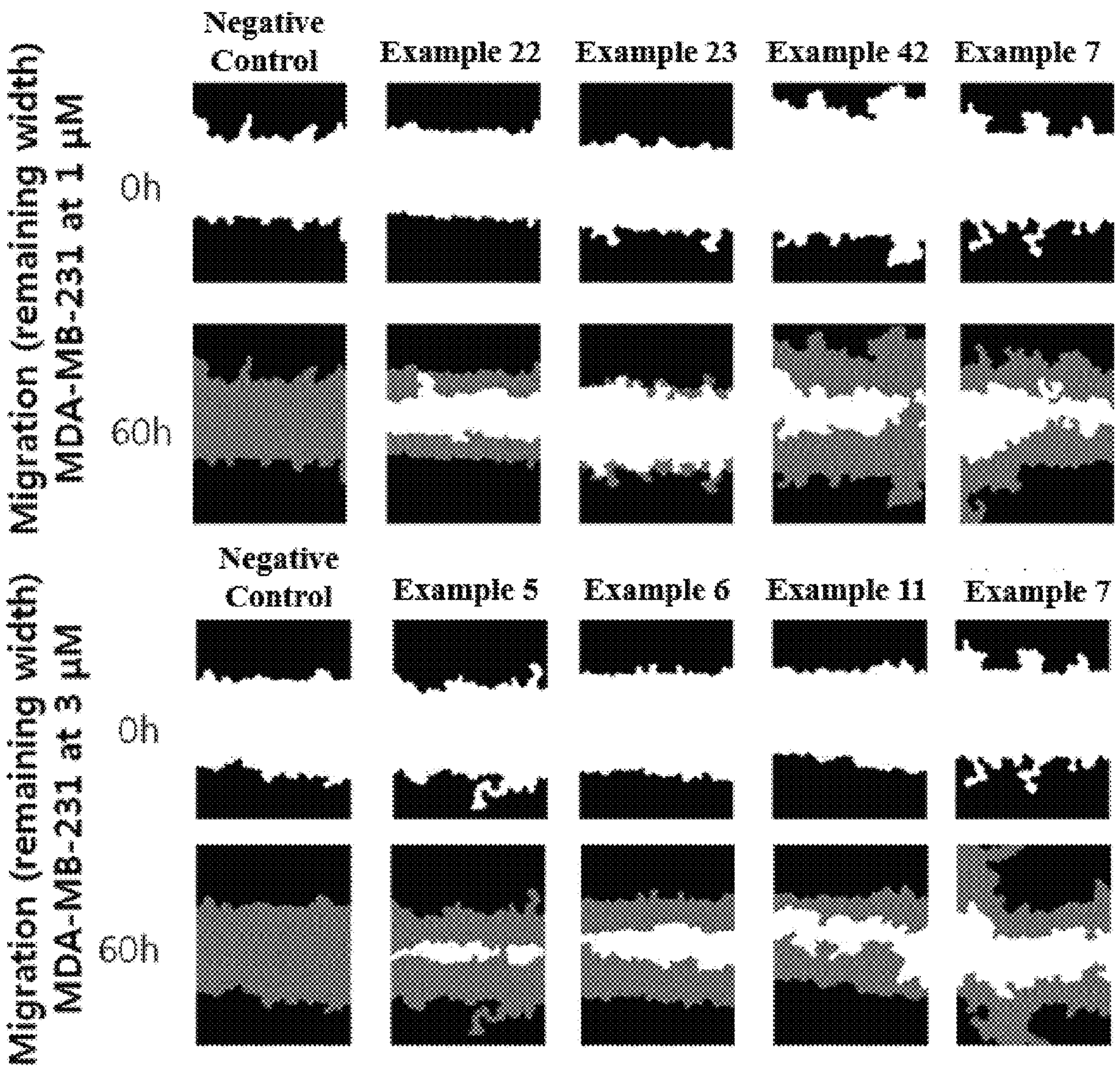

[Fig 4]
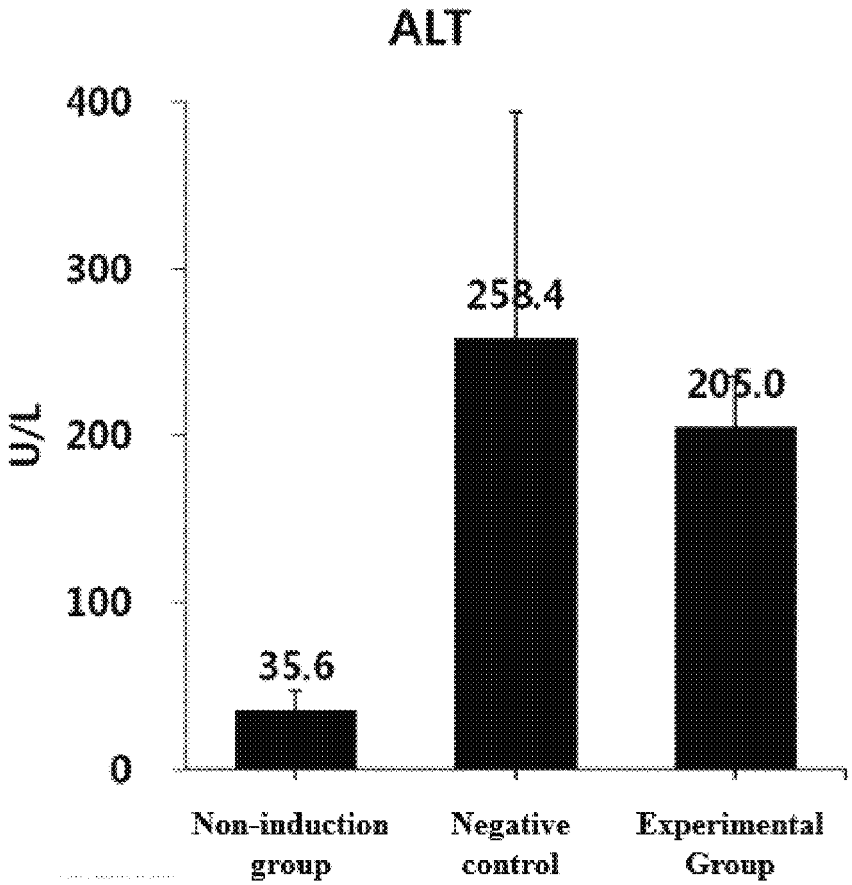

[Fig 5]
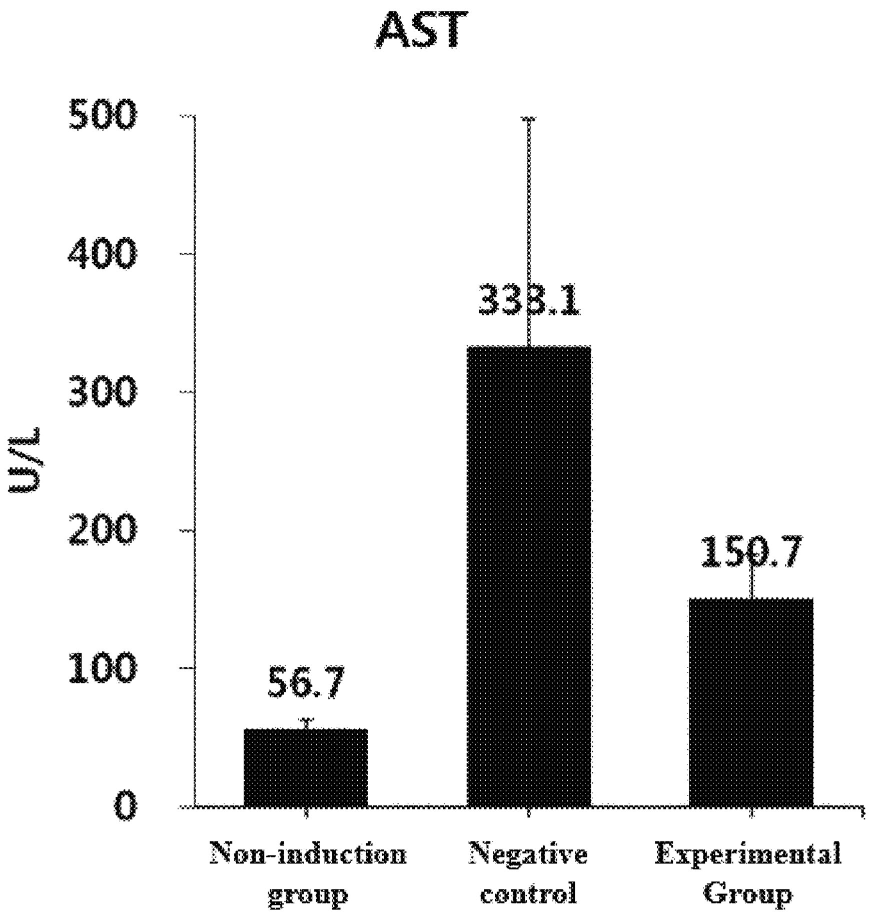

[Fig 6]
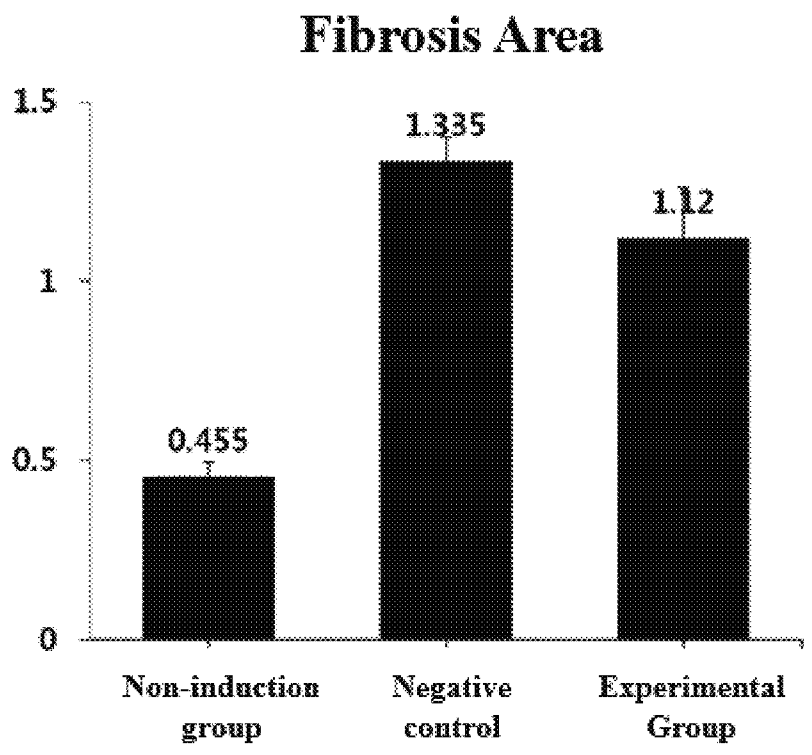

[Fig 7]
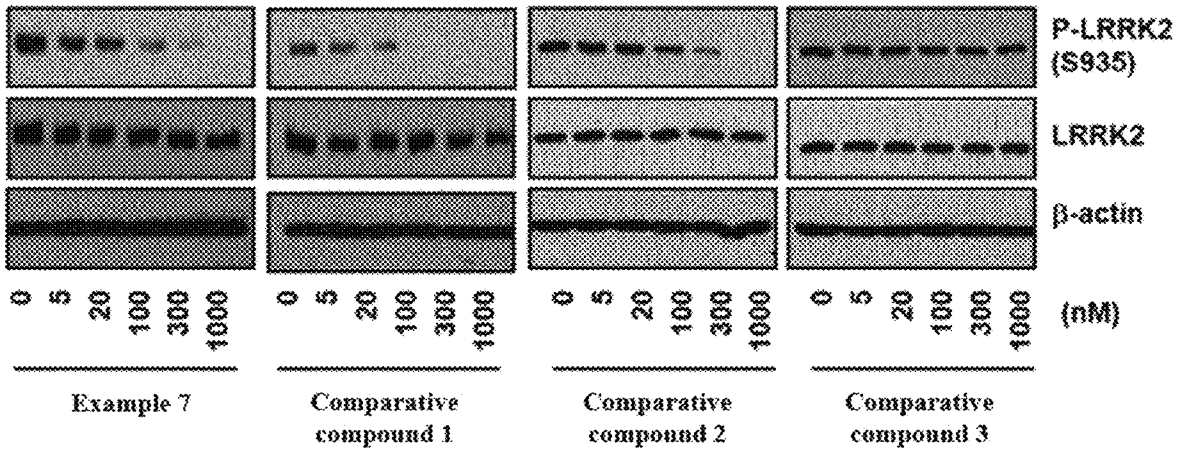

[Fig 8]
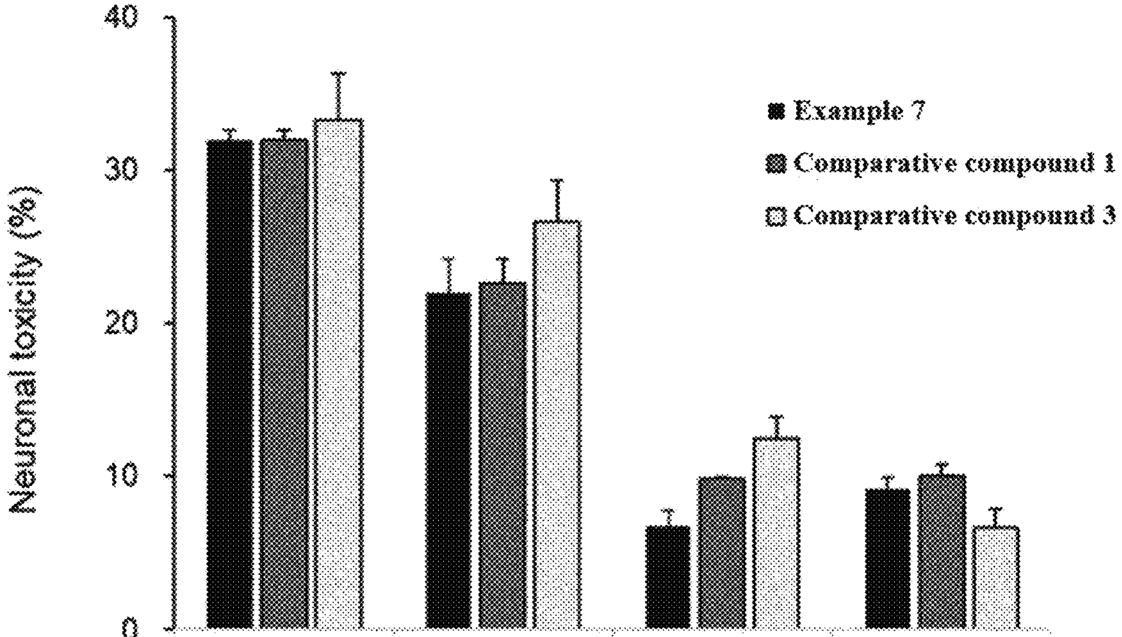
| | DMSO | 0.01μM | 0.1μM | 1μM |
|---|---|---|---|---|
| Example 7 | 31.95 | 21.97 | 6.74 | 9.21 |
| Comparative compound 1 | 31.95 | 22.63 | 9.81 | 10.01 |
| Comparative compound 3 | 33.25 | 26.65 | 12.44 | 6.65 |

[Fig 9]
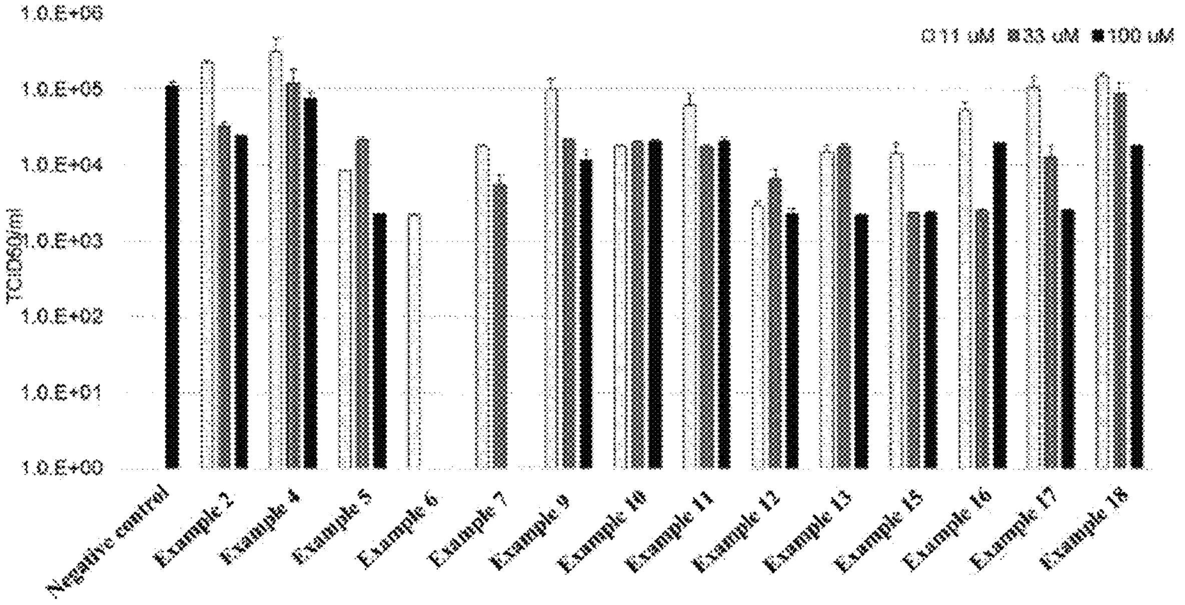

[Fig 10]
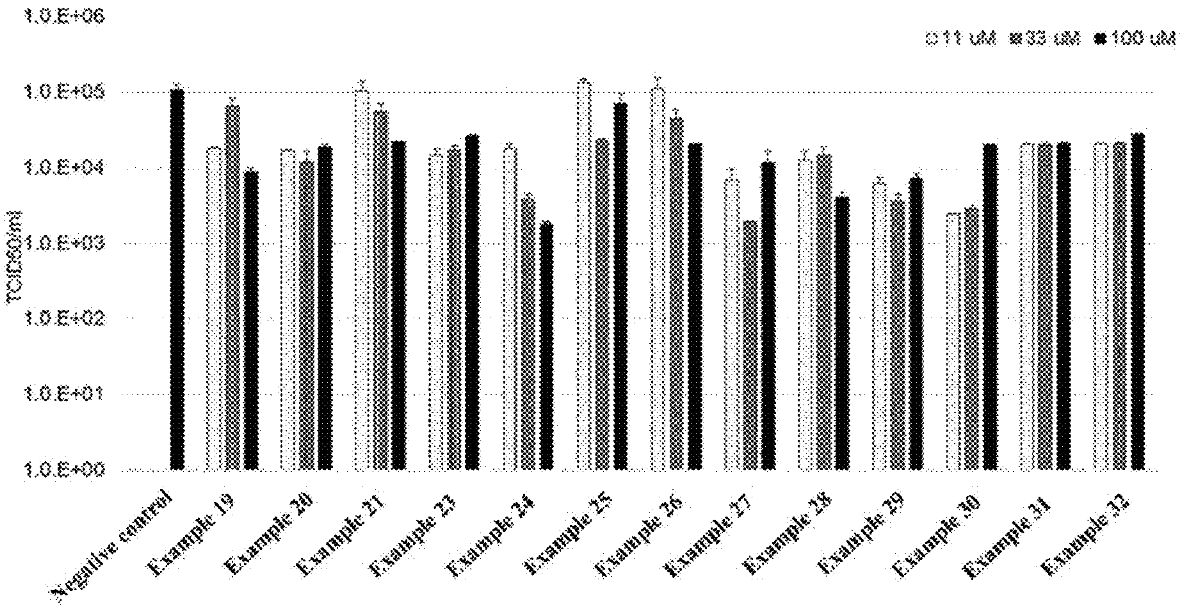

[Fig 11]
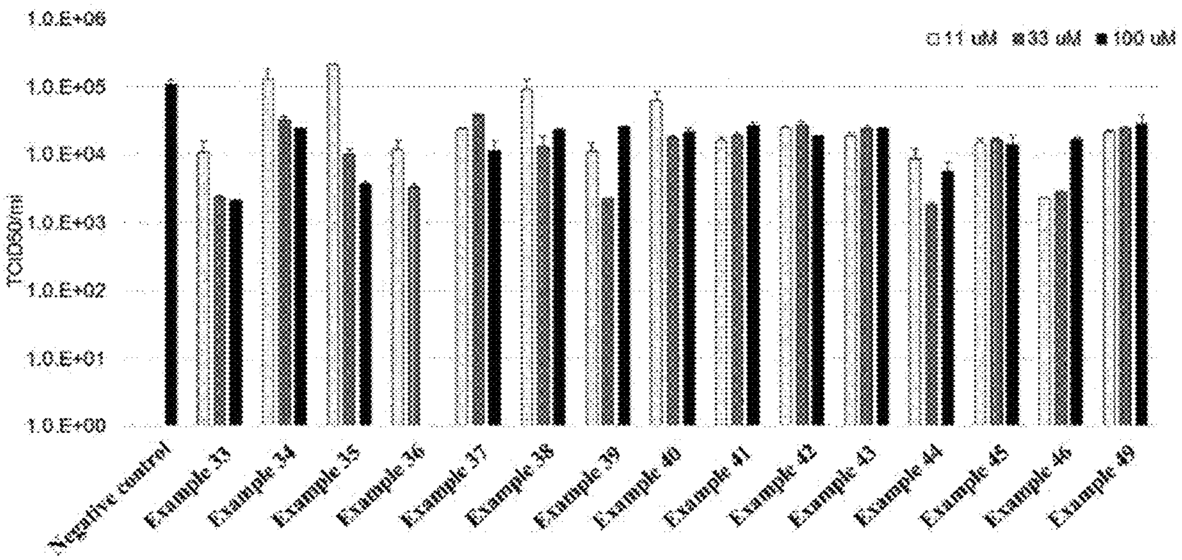

[Fig 12]
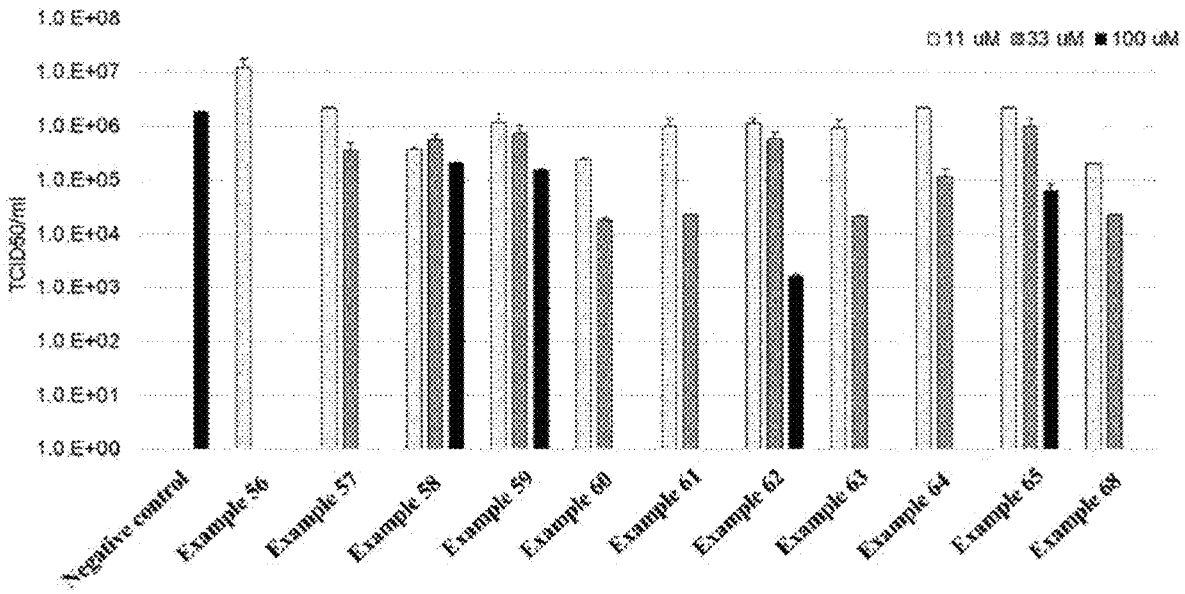

[Fig 13]
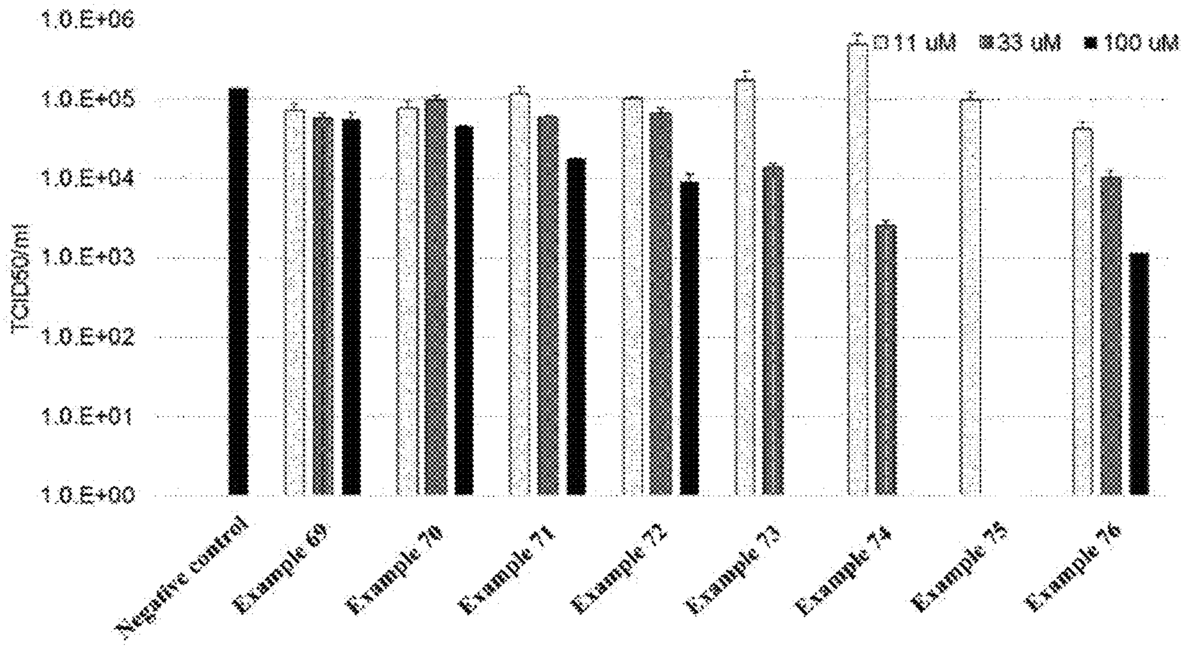

[Fig 14]
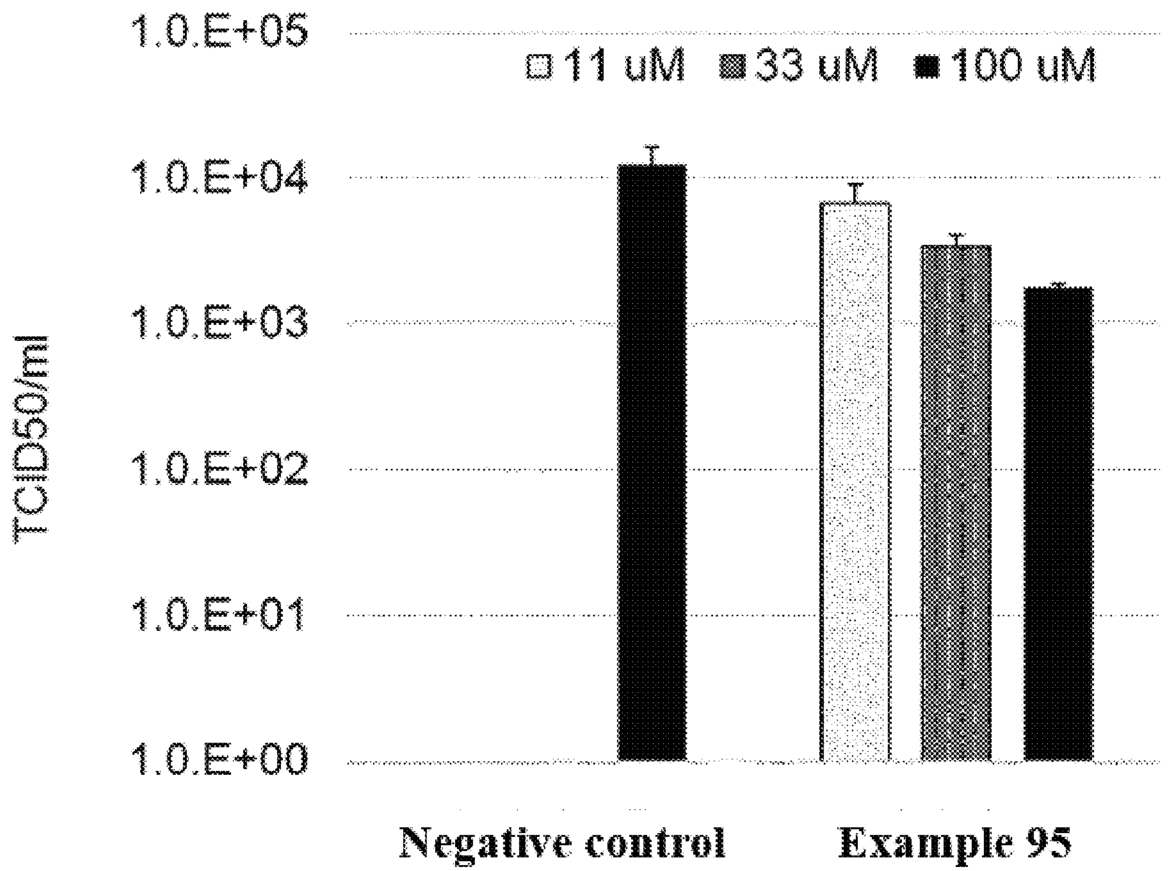

[Fig 15]
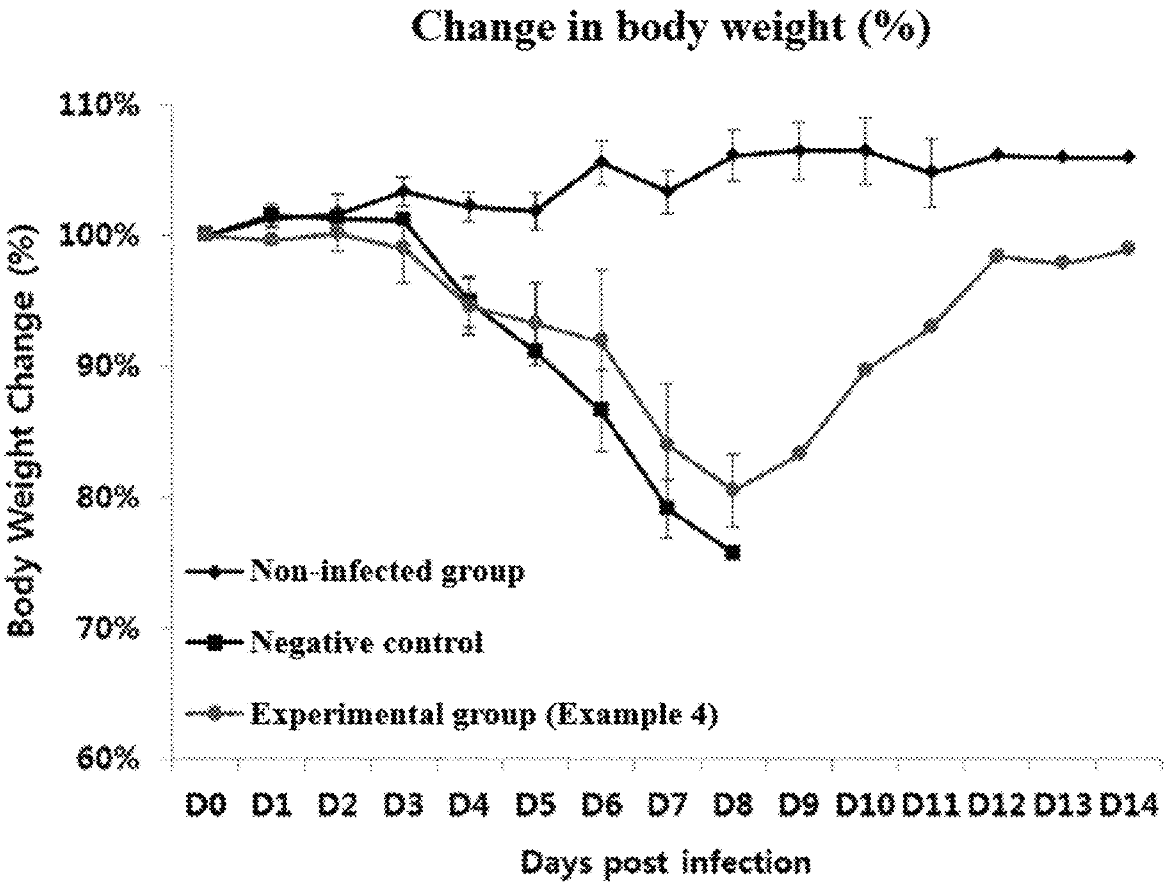

[Fig 16]
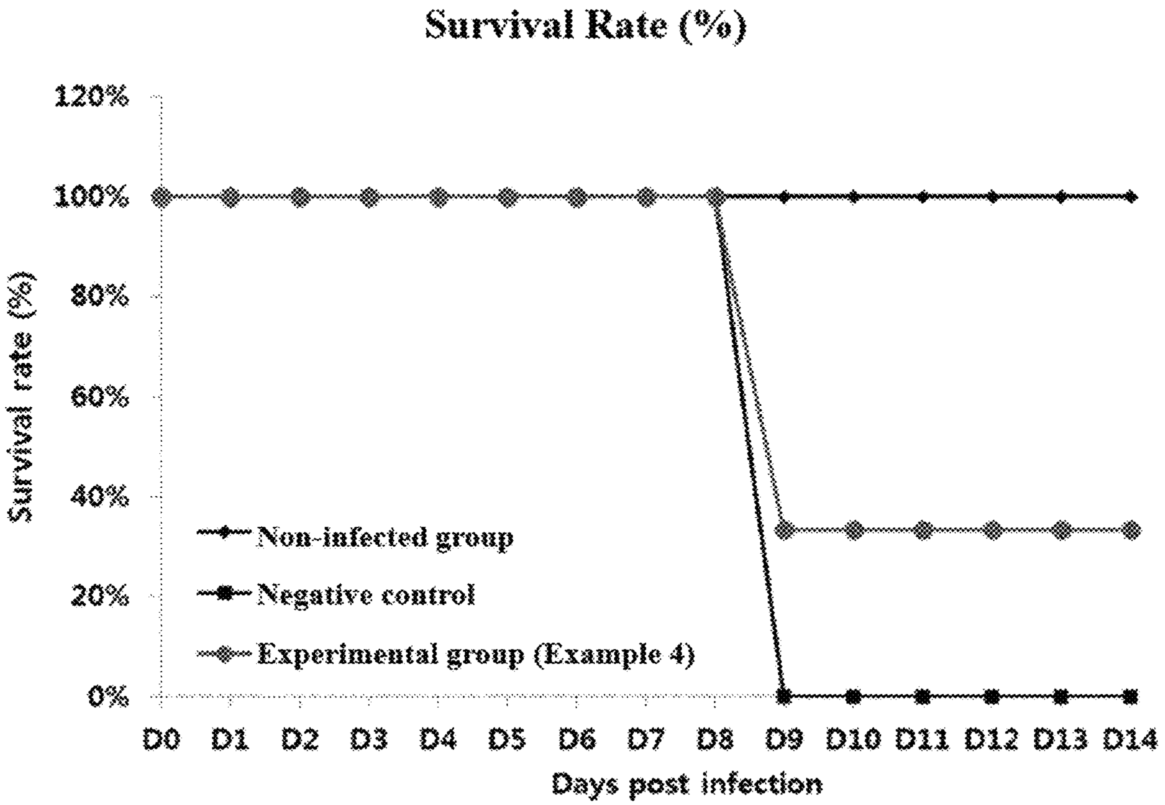

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: beta actin F primer

<400> SEQUENCE: 1

ggacttcgag caagagatgg                                                  20


<210> SEQ ID NO 2
<211> LENGTH: 20
<212> TYPE: DNA
<213> ORGANISM: Artificial Sequence
<220> FEATURE:
<223> OTHER INFORMATION: beta actin R primer

<400> SEQUENCE: 2

agcactgtgt tggcgtacag                                                  20


<210> SEQ ID NO 3
<211> LENGTH: 17
<212> TYPE: DNA
<213> ORGANISM: Artificial Sequence
<220> FEATURE:
<223> OTHER INFORMATION: alpha SMA F primer

<400> SEQUENCE: 3

ccgaccgaat gcagaag                                                     17


<210> SEQ ID NO 4
<211> LENGTH: 21
```

<212> TYPE: DNA
<213> ORGANISM: Artificial Sequence
<220> FEATURE:
<223> OTHER INFORMATION: alpha SMA R primer

<400> SEQUENCE: 4
acagagtatt tgcgctccgg a 21

<210> SEQ ID NO 5
<211> LENGTH: 21
<212> TYPE: DNA
<213> ORGANISM: Artificial Sequence
<220> FEATURE:
<223> OTHER INFORMATION: Col1 A1 F primer

<400> SEQUENCE: 5
cgaagacatc ccaccaatca c 21

<210> SEQ ID NO 6
<211> LENGTH: 21
<212> TYPE: DNA
<213> ORGANISM: Artificial Sequence
<220> FEATURE:
<223> OTHER INFORMATION: Col1 A1 R primer

<400> SEQUENCE: 6
acagatcacg tcatcgcaca a 21

<210> SEQ ID NO 7
<211> LENGTH: 20
<212> TYPE: DNA
<213> ORGANISM: Artificial Sequence
<220> FEATURE:
<223> OTHER INFORMATION: Col6A3 F primer

<400> SEQUENCE: 7
ctctaccgag cccaggtgtt 20

<210> SEQ ID NO 8
<211> LENGTH: 20
<212> TYPE: DNA
<213> ORGANISM: Artificial Sequence
<220> FEATURE:
<223> OTHER INFORMATION: Col6A3 R primer

<400> SEQUENCE: 8
atgagggtgc gaacgtactg 20

<210> SEQ ID NO 9
<211> LENGTH: 20
<212> TYPE: DNA
<213> ORGANISM: Artificial Sequence
<220> FEATURE:
<223> OTHER INFORMATION: beta actin F primer

<400> SEQUENCE: 9
tagccatcca ggctgtgctg 20

<210> SEQ ID NO 10
<211> LENGTH: 21
<212> TYPE: DNA
<213> ORGANISM: Artificial Sequence
<220> FEATURE:
<223> OTHER INFORMATION: beta actin R primer

<400> SEQUENCE: 10

```
caggatcttc atgaggtagt c                                              21


<210> SEQ ID NO 11
<211> LENGTH: 23
<212> TYPE: DNA
<213> ORGANISM: Artificial Sequence
<220> FEATURE:
<223> OTHER INFORMATION: Fibronectin1 F primer

<400> SEQUENCE: 11

ccctatctct gayaccgttg tcc                                            23


<210> SEQ ID NO 12
<211> LENGTH: 22
<212> TYPE: DNA
<213> ORGANISM: Artificial Sequence
<220> FEATURE:
<223> OTHER INFORMATION: Fibronectin1 R primer

<400> SEQUENCE: 12

tgccgcaact actgtgattc gg                                             22


<210> SEQ ID NO 13
<211> LENGTH: 22
<212> TYPE: DNA
<213> ORGANISM: Artificial Sequence
<220> FEATURE:
<223> OTHER INFORMATION: TGF beta1 F primer

<400> SEQUENCE: 13

tgctccaaac cacagagtag gc                                             22


<210> SEQ ID NO 14
<211> LENGTH: 22
<212> TYPE: DNA
<213> ORGANISM: Artificial Sequence
<220> FEATURE:
<223> OTHER INFORMATION: TGF beta1 R primer

<400> SEQUENCE: 14

cccagaacac taagcccatt gc                                             22


<210> SEQ ID NO 15
<211> LENGTH: 18
<212> TYPE: DNA
<213> ORGANISM: Artificial Sequence
<220> FEATURE:
<223> OTHER INFORMATION: alpha SMA F primer

<400> SEQUENCE: 15

tcagcgcctc cagttcct                                                  18


<210> SEQ ID NO 16
<211> LENGTH: 26
<212> TYPE: DNA
<213> ORGANISM: Artificial Sequence
<220> FEATURE:
<223> OTHER INFORMATION: alpha SMA R primer

<400> SEQUENCE: 16

aaaaaaaacc acgagtaaca aatcaa                                         26
```

IMIDAZOPYRIDINE DERIVATIVE AND PHARMACEUTICAL COMPOSITION COMPRISING SAME AS ACTIVE INGREDIENT

BACKGROUND OF THE DISCLOSURE

Field of the Disclosure

The present disclosure relates to an imidazopyridine derivative and a pharmaceutical composition containing the same as an active ingredient and, more particularly, to an imidazopyridine derivative that inhibits protein kinase activity and as such, can be used for preventing or treating cancer, neurodegenerative disease, non-alcoholic fatty liver disease, influenza, etc., and a pharmaceutical composition containing the same as an active ingredient.

Related Art

Kinases mediate a reaction in which a phosphate group from high-energy molecules, in particular, ATP, is transferred to a substrate. Kinases stabilize phosphoric anhydride bonds, and locate the substrate and the phosphate group at a specific position to increase a reaction rate. In most cases, the transition state resulting from the interaction with a phosphate group having a negative charge is electrostatically stabilized through surrounding amino acids having a positive charge, and some kinases may be co-ordinated with the phosphate group through a metal cofactor.

Kinases can be classified as, for example, protein kinases, lipid kinases, and carbohydrate kinases, according to the substrate and characteristics. Proteins, lipids, or carbohydrates may vary in their activity, reactivity, ability to bind to other molecules, etc., depending on the phosphorylation state. Kinases affect intracellular signal transduction and regulate complex biological mechanisms within cells. Due to phosphorylation, some molecules may have enhanced or reduced activities, and their ability to interact with other molecules may be controlled. Because many kinases respond to environmental conditions or signals, cells may control intracellular molecules by using kinases, depending on the situation. As such, kinase plays a crucial role in cell growth, differentiation, proliferation, survival, metabolism, signal transduction, cell transport, secretion, and many other cellular reaction pathways.

Protein kinases may increase or decrease the activity of a protein, become a marker for stabilization or degradation, place a protein in a specific cell compartment, or initiate or disturb interactions of a protein with other proteins. Protein kinases are known to account for the majority of kinases and are considered to be an important research target. Protein kinases regulate, together with phosphatase, proteins and enzymes as well as cell signal transduction. Although cell proteins are subject to numerous covalent bonds, not many of these bonds are reversible. Accordingly, it can be said that phosphorylation of proteins has a regulatory function. Protein kinases may often have multiple substrates, and sometimes, a particular protein may act as a substrate for at least one kinase. For this reason, protein kinases are named using factors that regulate their activities. For example, a calmodulin-dependent protein kinase is regulated by calmodulin. In some cases, kinases may be classified as sub-groups. For example, type I and type II cyclic AMP-dependent protein kinases include identical enzyme subunits, but their regulatory subunits binding to cyclic AMP are different from each other.

A protein kinase is an enzyme that plays an important role in the intracellular signal transduction process through the phosphorylation of the hydroxy group present in tyrosine, serine, or threonine residues of proteins, and plays an important role in signaling growth factors that induce cell growth, differentiation, and proliferation (Melnikova, I. et al., Nature Reviews Drug Discovery, 3 (2004), 993).

A balance between "on-states" and "off-states" of an intracellular signaling pathway is essential for maintenance of homeostasis of a cell. When a normal intracellular signaling pathway of, e.g., mostly continuation of "on-state" of intracellular signals is interrupted due to overexpression or mutation of a specific protein kinase, it may lead to an outbreak of various diseases such as cancer, inflammatory disease, metabolic disease and brain disease. It is estimated that human genome contains 518 protein kinases which constitute approximately 1.7% of all human genes; and the protein kinases can be broadly divided into tyrosine protein kinases (90 or more types) and serine/threonine protein kinases.

Medically important serine/threonine kinases include a family of mitogen-activated protein kinases (MAPKs), which act in a variety of biological processes. MAPK is activated upon phosphorylation by MAPK kinases (MAP2K or MAPKK) at specific tyrosine and threonine residues, and MAP2K is activated upon phosphorylation by MAP2K kinases (MAP3K, MAPKKK) at serine and serine/threonine residues. The MAP3K family includes several, including A/B/C-Raf, MEKK1/4, ASK1/2, MLK1/2/3, MEKK2/3, etc. Several mechanisms are involved in the activation of MAP3K in response to multiple extracellular stimuli, including cytokines, proliferation factors, and environmental stress.

Leucin-rich repeat kinase-2 (LRRK2) is a protein belonging to the leucine-rich repeat kinase family, and consists of a sequence of 2,527 amino acids with high similarity between species. LRRK2 has both GTP hydrolase (guanosine triphosphatase; GTPase) and serine/threonine kinase activity in one protein. The expressed LRRK2 has been observed in various organs and tissues including the brain, and at the cellular level, it is present in the cytoplasm or the cell membrane and the outer mitochondrial membrane.

The LRRK2 has been reported to be associated with Alzheimer's-disease-related mild cognitive impairment progression, L-dopa-induced dyskinesia, and neural-precursor-differentiation-related CNS disorder. Furthermore, the G2019S mutation of the LRRK2 has been reported to increase the incidence of non-skin cancer such as acute myeloid leukemia (AML), kidney cancer, breast cancer, lung cancer, prostate cancer and the like. Specifically, the G2019S mutation of the LRRK2 increases the catalytic activity of the LRRK2 kinase domain. Moreover, it has been reported that the LRRK2 is also associated with amyotrophic lateral sclerosis, rheumatoid arthritis, and ankylosing spondylitis This inappropriately high protein kinase activity is directly or indirectly associated with a number of diseases resulting from abnormal cell actions. Accordingly, attempts have been made to prevent or treat related diseases by selectively inhibiting protein kinase activity.

Related Art Documents

Patent Documents (Patent Document 1) Korean Patent Application No. 10-2018-0021255

(Patent Document 2) International Patent Publication No. WO 2011/038572

SUMMARY

One aspect of the present disclosure is directed to providing an imidazopyridine derivative compound capable of inhibiting protein kinase activity.

Another aspect of the present disclosure is directed to providing a pharmaceutical composition containing an imidazopyridine derivative compound as an active ingredient for preventing or treating cancer, neurodegenerative disease, non-alcoholic fatty liver disease, influenza, etc., by inhibiting protein kinase activity.

According to one embodiment of the present disclosure, there is provided a compound represented by Formula 1 below, a stereoisomer thereof, a solvate thereof, a hydrate thereof, or a pharmaceutically acceptable salt thereof:

[Formula 1]

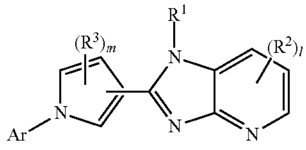

wherein, Ar is $C_6$-$C_{20}$ aryl or 5 to 20 membered heteroaryl; $R^1$, $R^2$ and $R^3$ are each, independently of one another, selected from the group consisting of hydrogen, halogen, hydroxy, cyano, nitro, —$SR^a$, —S(=O) $R^a$, —S(=O)$_2R^a$, —$NR^bR^c$, —$CO_2R^b$, —CO—$NR^b$ $R^c$, $C_1$-$C_{20}$ alkyl, $C_1$-$C_6$ haloalkyl, $C_1$-$C_6$ hydroxyalkyl, $C_1$-$C_6$ alkoxyalkyl, $C_1$-$C_6$ aminoalkyl, $C_2$-$C_{20}$ alkenyl, $C_2$-$C_{20}$ alkynyl, $C_1$-$C_8$ alkoxy, $C_3$-$C_{12}$ cycloalkyl, $C_4$-$C_{12}$ cycloalkylalkyl, 3-12 membered heterocyclyl, 3-12 membered heterocyclylalkyl, $C_6$-$C_{20}$ aryl, and 5-20 membered heteroaryl; the $R^a$, $R^b$ and $R^c$ are each, independently of one another, selected from the group consisting of hydrogen, halogen, hydroxy, cyano, nitro, $C_1$-$C_{20}$ alkyl, $C_1$-$C_6$ haloalkyl, $C_1$-$C_6$ hydroxyalkyl, $C_1$-$C_6$ alkoxyalkyl, $C_1$ —$C_6$ aminoalkyl, $C_2$-$C_{20}$ alkenyl, $C_2$-$C_{20}$ alkynyl, $C_1$-$C_8$ alkoxy, $C_3$-$C_{12}$ cycloalkyl, $C_4$-$C_{12}$ cycloalkylalkyl, 3-12 membered heterocyclyl, 3-12 membered heterocyclylalkyl, $C_6$-$C_{20}$ aryl, and 5-20 membered heteroaryl; the 1 is an integer of 0 to 3; and m is an integer of 0 to 3, wherein the alkyl, haloalkyl, hydroxyalkyl, alkoxyalkyl, aminoalkyl, alkenyl, alkynyl, alkoxy, cycloalkyl, cycloalkylalkyl, heterocyclyl, heterocyclylalkyl, aryl and heteroaryl each may be substituted with one or more substituents selected from the group consisting of hydrogen, halogen, hydroxy, cyano, nitro, —$SR^a$, —S(=O) $R^a$, —S(=O)$_2R^a$, —$NR^bR^c$, —$CO_2R^b$, —CO—$NR^bR^c$, $C_1$-$C_{10}$ alkyl, $C_1$-$C_4$ haloalkyl, $C_1$-$C_4$ hydroxyalkyl, $C_1$-$C_4$ alkoxyalkyl, $C_1$-$C_4$ aminoalkyl, $C_2$-$C_{10}$ alkenyl, $C_2$-$C_{10}$ alkynyl, $C_1$-$C_4$ alkoxy, $C_3$-$C_{10}$ cycloalkyl, $C_4$-$C_{10}$ cycloalkylalkyl, 3-10 membered heterocyclyl, 3-10 membered heterocyclylalkyl, $C_6$-$C_{12}$ aryl, and 5-12 membered heteroaryl.

According to another embodiment of the present disclosure, there is provided a compound represented by Formula 2 below, a stereoisomer thereof, a solvate thereof, a hydrate thereof, or a pharmaceutically acceptable salt thereof:

[Formula 2]

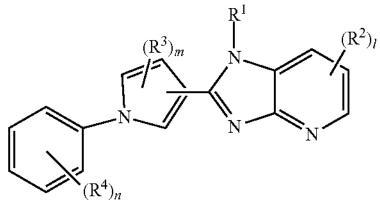

wherein, $R^1$ to $R^3$, 1 and m are the same as defined in Formula 1 above; $R^4$ is independently of one another, selected from the group consisting of hydrogen, halogen, hydroxy, cyano, nitro, —$SR^a$, —S(=O) $R^a$, —S(=O)$_2R^2$, —$NR^bR^c$, —$CO_2R^b$, —CO—$NR^bR^c$, $C_1$-$C_{10}$ alkyl, $C_1$-$C_4$ haloalkyl, $C_1$-$C_4$ hydroxyalkyl, $C_1$-$C_4$ alkoxyalkyl, $C_1$-$C_4$ aminoalkyl, $C_2$-$C_{10}$ alkenyl, $C_2$-$C_{10}$ alkynyl, $C_1$-$C_4$ alkoxy, $C_3$-$C_{10}$ cycloalkyl, $C_4$-$C_{10}$ cycloalkylalkyl, 3-10 membered heterocyclyl, 3-10 membered heterocyclylalkyl, $C_6$-$C_{12}$ aryl, and 5-12 membered heteroaryl, or adjacent groups may be linked to each other to form a ring; and n is an integer of 0 to 5, wherein the alkyl, haloalkyl, hydroxyalkyl, alkoxyalkyl, aminoalkyl, alkenyl, alkynyl, alkoxy, cycloalkyl, cycloalkylalkyl, heterocyclyl, heterocyclylalkyl, aryl and heteroaryl each may be further substituted with one or more substituents selected from the group consisting of hydrogen, halogen, hydroxy, cyano, nitro, —$SR^a$, —S(=O) $R^a$, —S(=O)$_2R^a$, —$NR^bR^c$, —$CO_2R^b$, —CO—$NR^bR^c$, $C_1$-$C_{10}$ alkyl, $C_1$-$C_4$ haloalkyl, $C_1$-$C_4$ hydroxyalkyl, $C_1$-$C_4$ alkoxyalkyl, $C_1$-$C_4$ aminoalkyl, $C_2$-$C_{10}$ alkenyl, $C_2$-$C_{10}$ alkynyl, $C_1$-$C_4$ alkoxy, $C_3$-$C_{10}$ cycloalkyl, $C_4$-$C_{10}$ cycloalkylalkyl, 3-10 membered heterocyclyl, 3-10 membered heterocyclylalkyl, $C_6$-$C_{12}$ aryl, and 5-12 membered heteroaryl.

According to yet another embodiment of the present disclosure, there is provided a compound represented by Formula 3 or Formula 4 below, a stereoisomer thereof, a solvate thereof, a hydrate thereof, or a pharmaceutically acceptable salt thereof:

[Formula 3]

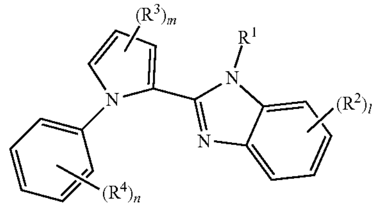

[Formula 4]

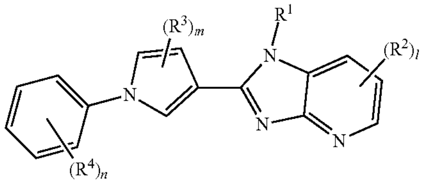

wherein, $R^1$ to $R^4$, 1, m and n are the same as defined in Formula 2 above.

According to yet another embodiment of the present disclosure, there is provided a compound represented by Formula 5 below, a stereoisomer thereof, a solvate thereof, a hydrate thereof, or a pharmaceutically acceptable salt thereof:

[Formula 5]

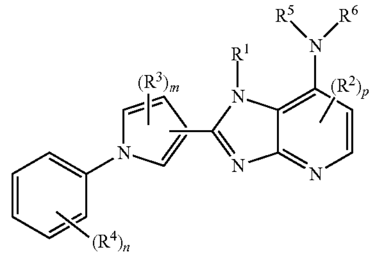

wherein, $R^1$ to $R^4$, 1, m and n are the same as defined in Formula 2 above; p is an integer from 0 to 2; and $R^5$ and $R^6$ are each, independently of one another, selected from the group consisting of hydrogen, halogen, hydroxy, cyano, nitro, $C_1$-$C_{20}$ alkyl, $C_1$-$C_6$ haloalkyl, $C_1$-$C_6$ hydroxyalkyl, $C_1$-$C_6$ alkoxyalkyl, $C_1$-$C_6$ aminoalkyl, $C_2$-$C_{20}$ alkenyl, $C_2$-$C_{20}$ alkynyl, $C_1$-$C_8$ alkoxy, $C_3$-$C_{12}$ cycloalkyl, $C_4$-$C_{12}$ cycloalkylalkyl, 3-12 membered heterocyclyl, 3-12 membered heterocyclylalkyl, $C_6$-$C_{20}$ aryl, and 5-20 membered heteroaryl, wherein the alkyl, haloalkyl, hydroxyalkyl, alkoxyalkyl, aminoalkyl, alkenyl, alkynyl, alkoxy, cycloalkyl, cycloalkylalkyl, heterocyclyl, heterocyclylalkyl, aryl and heteroaryl each may be substituted with one or more substituents selected from the group consisting of hydrogen, halogen, hydroxy, cyano, nitro, —$SR^a$, —S(═O) $R^a$, —S(═O)$_2R^2$, —$NR^bR^c$, —$CO_2R^b$, —CO—$NR^bR^c$, $C_1$-$C_{10}$ alkyl, $C_1$-$C_4$ haloalkyl, $C_1$-$C_4$ hydroxyalkyl, $C_1$-$C_4$ alkoxyalkyl, $C_1$-$C_4$ aminoalkyl, $C_2$-$C_{10}$ alkenyl, $C_2$-$C_{10}$ alkynyl, $C_1$-$C_4$ alkoxy, $C_3$-$C_{10}$ cycloalkyl, $C_4$-$C_{10}$ cycloalkylalkyl, 3-10 membered heterocyclyl, 3-10 membered heterocyclylalkyl, $C_6$-$C_{12}$ aryl, and 5-12 membered heteroaryl.

It may be a compound represented by Formula 6 or Formula 7 below, a stereoisomer thereof, a solvate thereof, a hydrate thereof, or a pharmaceutically acceptable salt thereof:

[Formula 6]

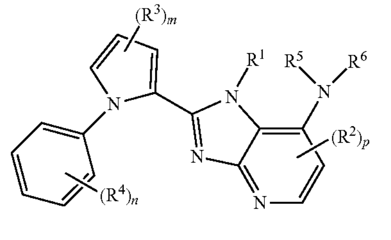

[Formula 7]

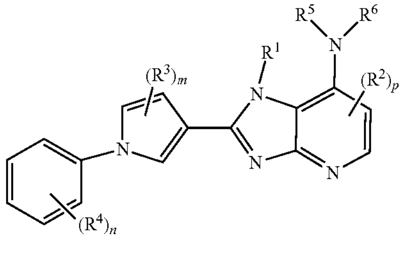

wherein, $R^1$ to $R^6$, m, n and p are the same as defined in Formula 5 above.

The compound represented by Formula 1 may be a compound selected from the group consisting of the following compounds, a stereoisomer thereof, a solvate thereof, a hydrate thereof, or a pharmaceutically acceptable salt thereof:

1) (S)-6-bromo-2-(2,5-dimethyl-1-(4-morpholinophenyl)-1H-pyrrol-3-yl)-N-(1-(ethylsulfonyl) pyrrolidine-3-yl)-3H-imidazo[4,5-b]pyridine-7-amine;
2) (S)-6-bromo-2-(2,5-dimethyl-1-(3-morpholinophenyl)-1H-pyrrol-3-yl)-N-(1-(ethylsulfonyl) pyrrolidine-3-yl)-3H-imidazo[4,5-b]pyridine-7-amine;
3) (S)-6-bromo-2-(2,5-dimethyl-1-(3-(2-morpholinoethoxy) phenyl)-1H-pyrrol-3-yl)-N-(1-(ethylsulfonyl) pyrrolidine-3-yl)-1H-imidazo[4,5-b]pyridine-7-amine;
4) (S)-6-bromo-2-(2,5-dimethyl-1-(4-(2-morpholinoethoxy) phenyl)-1H-pyrrol-3-yl)-N-(1-(ethylsulfonyl) pyrrolidine-3-yl)-1H-imidazo[4,5-b]pyridine-7-amine;
5) (S)-(4-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)phenyl) (morpholino) methanone;
6) (S)-(3-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)phenyl) (morpholino) methanone;
7)N-(3-(3-(6-bromo-7-(((S)-1-(ethylsulfonyl) pyrrolidine-3-yl)amino)-3H-imidazo[4,5-b]pyridine-2-yl)-2,5-dimethyl-1H-pyrrol-1-yl)-4-methylphenyl) methanesulfonamide;
8)N-(4-(3-(6-bromo-7-(((S)-1-(ethylsulfonyl) pyrrolidine-3-yl)amino)-3H-imidazo[4,5-b]pyridine-2-yl)-2,5-dimethyl-1H-pyrrol-1-yl)-3-methylphenyl) methanesulfonamide;
9)N-(3-(3-(6-bromo-7-(((S)-1-(ethylsulfonyl) pyrrolidine-3-yl)amino)-3H-imidazo[4,5-b]pyridine-2-yl)-2,5-dimethyl-1H-pyrrol-1-yl)-2-methylphenyl) methanesulfonamide;
10) (S)-6-bromo-2-(2,5-dimethyl-1-(4-(morpholinosulfonyl)phenyl)-1H-pyrrol-3-yl)-N-(1-(ethylsulfonyl) pyrrolidine-3-yl)-3H-imidazo[4,5-b]pyridine-7-amine;
11) (S)-6-bromo-2-(2,5-dimethyl-1-(3-(morpholinosulfonyl)phenyl)-1H-pyrrol-3-yl)-N-(1-(ethylsulfonyl) pyrrolidine-3-yl)-3H-imidazo[4,5-b]pyridine-7-amine;
12) (S)—N-(3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)phenyl) methanesulfonamide;
13) (S)-6-bromo-2-(1-(2,6-dichlorophenyl)-2,5-dimethyl-1H-pyrrol-3-yl)-N-(1-(ethylsulfonyl) pyrrolidine-3-yl)-3H-imidazo[4,5-b]pyridine-7-amine;
14) 6-bromo-2-(1-(2,5-dichlorophenyl)-2,5-dimethyl-1H-pyrrol-3-yl)-N—((S)-1-(ethylsulfonyl) pyrrolidine-3-yl)-3H-imidazo[4,5-b]pyridine-7-amine;
15) (S)-6-bromo-2-(1-(3,4-dichlorophenyl)-2,5-dimethyl-1H-pyrrol-3-yl)-N-(1-(ethylsulfonyl) pyrrolidine-3-yl)-3H-imidazo[4,5-b]pyridine-7-amine;
16) 6-bromo-2-(1-(2-chlorophenyl)-2,5-dimethyl-1H-pyrrol-3-yl)-N—((S)-1-(ethylsulfonyl) pyrrolidine-3-yl)-3H-imidazo[4,5-b]pyridine-7-amine;
17)3-(3-(6-bromo-7-(((S)-1-(ethylsulfonyl) pyrrolidine-3-yl)amino)-3H-imidazo[4,5-b]pyridine-2-yl)-2,5-dimethyl-1H-pyrrol-1-yl)-4-chlorobenzenesulfonamide;
18) (S)-3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)-N-methylbenzenesulfonamide;
19) (S)-3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)-N-ethylbenzenesulfonamide;

20) (S)-3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)benzamide;

21) (S)-6-bromo-N-(1-(ethylsulfonyl) pyrrolidine-3-yl)-2-(1-(3-(2-methoxyethoxy)phenyl)-2,5-dimethyl-1H-pyrrol-3-yl)-1H-imidazo[4,5-b]pyridine-7-amine;

22) (S)-6-bromo-N-(1-(ethylsulfonyl) pyrrolidine-3-yl)-2-(1-(4-(2-methoxyethoxy)phenyl)-2,5-dimethyl-1H-pyrrol-3-yl)-1H-imidazo[4,5-b]pyridine-7-amine;

23) (S)-3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)benzenesulfonamide;

24) (S)-4-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)benzenesulfonamide;

25) (S)-6-bromo-2-(2,5-dimethyl-1-phenyl-1H-pyrrol-3-yl)-N-(1-(ethylsulfonyl) pyrrolidine-3-yl)-3H-imidazo[4,5-b]pyridine-7-amine;

26)$_3$-((6-bromo-2-(1-(2,6-dichlorophenyl)-2,5-dimethyl-1H-pyrrol-3-yl)-3H-imidazo[4,5-b]pyridine-7-yl)amino)benzenesulfonamide;

27)$_3$-(6-bromo-2-(2,5-dimethyl-1-(4-(morpholine-4-carbonyl)phenyl)-1H-pyrrol-3-yl)-3H-imidazo[4,5-b]pyridine-7-yl)amino)benzenesulfonamide;

28)$_3$-((6-bromo-2-(2,5-dimethyl-1-(3-(morpholine-4-carbonyl)phenyl)-1H-pyrrol-3-yl)-3H-imidazo[4,5-b]pyridine-7-yl)amino)benzenesulfonamide;

29)$_3$-((6-bromo-2-(2,5-dimethyl-1-(4-(morpholinosulfonyl)phenyl)-1H-pyrrol-3-yl)-3H-imidazo[4,5-b]pyridine-7-yl)amino)benzenesulfonamide;

30)$_3$-((6-bromo-2-(2,5-dimethyl-1-(3-(morpholinosulfonyl)phenyl)-1H-pyrrol-3-yl)-3H-imidazo[4,5-b]pyridine-7-yl)amino)benzenesulfonamide;

31)$_3$-((6-bromo-2-(1-(2-chlorophenyl)-2,5-dimethyl-1H-pyrrol-3-yl)-3H-imidazo[4,5-b]pyridine-7-yl)amino)benzenesulfonamide;

32)$_3$-((6-bromo-2-(2,5-dimethyl-1-(2-methyl-4-(methylsulfonamido)phenyl)-1H-pyrrol-3-yl)-3H-imidazo[4,5-b]pyridine-7-yl)amino)benzenesulfonamide;

33)$_3$-((6-bromo-2-(2,5-dimethyl-1-(2-methyl-5-(methylsulfonamido)phenyl)-1H-pyrrol-3-yl)-3H-imidazo[4,5-b]pyridine-7-yl)amino)benzenesulfonamide;

34)$_3$-((6-bromo-2-(2,5-dimethyl-1-(2-methyl-3-(methylsulfonamido)phenyl)-1H-pyrrol-3-yl)-3H-imidazo[4,5-b]pyridine-7-yl)amino)benzenesulfonamide;

35)$_3$-((6-bromo-2-(1-(2,5-dichlorophenyl)-2,5-dimethyl-1H-pyrrol-3-yl)-3H-imidazo[4,5-b]pyridine-7-yl)amino)benzenesulfonamide;

36)$_3$-(3-(6-bromo-7-((3-sulfamoylphenyl)amino)-3H-imidazo[4,5-b]pyridine-2-yl)-2,5-dimethyl-1H-pyrrole-1-yl)-4-chlorobenzenesulfonamide;

37)$_3$-((6-bromo-2-(2,5-dimethyl-1-(3-morpholinophenyl)-1H-pyrrol-3-yl)-3H-imidazo[4,5-b]pyridine-7-yl)amino)benzenesulfonamide;

38)$_3$-((6-bromo-2-(2,5-dimethyl-1-(3-(2-morpholinoethoxy)phenyl)-1H-pyrrol-3-yl)-1H-imidazo[4,5-b]pyridine-7-yl)amino)benzenesulfonamide;

39)$_3$-((6-bromo-2-(2,5-dimethyl-1-(4-(2-morpholinoethoxy)phenyl)-1H-pyrrol-3-yl)-1H-imidazo[4,5-b]pyridine-7-yl)amino)benzenesulfonamide;

40)$_3$-((6-bromo-2-(2,5-dimethyl-1-(4-morpholinophenyl)-1H-pyrrol-3-yl)-3H-imidazo[4,5-b]pyridine-7-yl)amino)benzenesulfonamide;

41)$_3$-((2-(1-(benzo[d][1,3]dioxole-5-yl)-2,5-dimethyl-1H-pyrrol-3-yl)-6-bromo-3H-imidazo[4,5-b]pyridine-7-yl)amino)benzenesulfonamide;

42)$_3$-((6-bromo-2-(1-(3-(2-methoxyethoxy)phenyl)-2,5-dimethyl-1H-pyrrol-3-yl)-1H-imidazo[4,5-b]pyridine-7-yl)amino)benzenesulfonamide;

43)$_3$-((6-bromo-2-(2,5-dimethyl-1-phenyl-1H-pyrrol-3-yl)-1H-imidazo[4,5-b]pyridine-7-yl)amino)benzenesulfonamide;

44)$_3$-(3-(7-(benzo[d][1,3]dioxole-5-yl-amino)-6-bromo-3H-imidazo[4,5-b]pyridine-2-yl)-2,5-dimethyl-1H-pyrrol-1-yl)benzenesulfonamide;

45)$_2$-(1-(benzo[d][1,3]dioxole-5-yl)-2,5-dimethyl-1H-pyrrol-3-yl)-6-bromo-N-(4-(2-methoxyethoxy)phenyl)-3H-imidazo[4,5-b]pyridine-7-amine;

46)$_3$-(3-(6-bromo-7-((4-(2-methoxyethoxy)phenyl)amino)-3H-imidazo[4,5-b]pyridine-2-yl)-2,5-dimethyl-1H-pyrrol-1-yl)benzenesulfonamide;

47)$_3$-((6-bromo-2-(2,5-dimethyl-1-(pyridine-3-yl)-1H-pyrrol-3-yl)-1H-imidazo[4,5-b]pyridine-7-yl)amino)benzenesulfonamide;

48)$_3$-((6-bromo-2-(2,5-dimethyl-1-(pyridine-4-ylmethyl)-1H-pyrrol-3-yl)-1H-imidazo[4,5-b]pyridine-7-yl)amino)benzenesulfonamide;

(S)-2-(1-(benzo[d][1,3]dioxole-5-yl)-2,5-dimethyl-1H-pyrrol-3-yl)-6-bromo-N-(1-(ethylsulfonyl) pyrrolidine-3-yl)-3H-imidazo[4,5-b]pyridine-7-amine;

50)N-(3-(3-(7-(((S)-1-(ethylsulfonyl) pyrrolidine-3-yl)amino)-3H-imidazo[4,5-b]pyridine-2-yl)-2,5-dimethyl-1H-pyrrol-1-yl)-4-methylphenyl) methanesulfonamide;

51)N-(3-(3-(6-chloro-7-(((S)-1-(ethylsulfonyl) pyrrolidine-3-yl)amino)-3H-imidazo[4,5-b]pyridine-2-yl)-2,5-dimethyl-1H-pyrrol-1-yl)-4-methylphenyl) methanesulfonamide;

52) (S)-6-chloro-2-(2,5-dimethyl-1-(4-(2-morpholinoethoxy)phenyl)-1H-pyrrol-3-yl)-N-(1-(ethylsulfonyl) pyrrolidine-3-yl)-1H-imidazo[4,5-b]pyridine-7-amine;

53) (S)-2-(2,5-dimethyl-1-(4-(2-morpholinoethoxy)phenyl)-1H-pyrrol-3-yl)-N-(1-(ethylsulfonyl) pyrrolidine-3-yl)-1H-imidazo[4,5-b]pyridine-7-amine;

54) (S)-(3-(3-(6-chloro-7-((1-(ethylsulfonyl) pyrrolidine-3-yl)amino)-1H-imidazo[4,5-b]pyridine-2-yl)-2,5-dimethyl-1H-pyrrol-1-yl)phenyl) (morpholino) methanone;

55) (S)-(3-(3-(7-((1-(ethylsulfonyl) pyrrolidine-3-yl)amino)-3H-imidazo[4,5-b]pyridine-2-yl)-2,5-dimethyl-1H-pyrrol-1-yl)phenyl) (morpholino) methanone;

56) (S)-3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)-N-(2-(diethylamino)ethyl)benzamide;

57) (S)-4-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)-N-(2-(diethylamino)ethyl)benzamide;

58) (S)-3-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)benzoic acid;

59) (S)-4-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)benzoic acid;

60) (S)-3-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)-N-((dimethylamino)methyl)benzamide;

61) (S)-3-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)-N-(2-(dimethylamino)ethyl)-N-methylbenzamide;

62) (S)-4-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)-N-(2-(dimethylamino)ethyl)benzamide;

63) (S)-4-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)-N-(2-(dimethylamino)ethyl)-N-methylbenzamide;

64) (S)—N-(3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)phenyl)-2-(dimethylamino) acetamide;

65) (S)—N-(3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)phenyl)-2-(4-methylpiperazine-1-yl) acetamide;

66) (S)—N-(3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)phenyl)-2-morpholinoacetamide;

67) (S)-(4-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)phenyl) (4-methylpiperazine-1-yl) methanone;

68) (S)-(3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)phenyl) (4-methylpiperazine-1-yl) methanone;

69) (S)-3-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)-N-(2-morpholinoethyl)benzamide;

70) (S)-4-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)-N-(2-morpholinoethyl)benzamide;

71) (S)-3-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)-N-(2-(4-methylpiperazine-1-yl) ethyl)benzamide;

$72)_3$ (S)-4-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)-N-(2-(4-methylpiperazine-1-yl) ethyl)benzamide;

73)N-(4-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-3-methylphenyl)-2-(dimethylamino) acetamide;

74)N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-4-methylphenyl)-2-(dimethylamino) acetamide;

75)N-(4-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-3-methylphenyl)-2-(4-methylpiperazine-1-yl) acetamide;

76)N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-4-methylphenyl)-2-(4-methylpiperazine-1-yl) acetamide;

77)N-(4-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-3-methylphenyl)-2-morpholinoacetamide;

78)N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-4-methylphenyl)-2-morpholinoacetamide;

79)N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-2-methylphenyl)-3-(dimethylamino) propanamide;

80)N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-4-methylphenyl)-3-(dimethylamino) propanamide;

81) (3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-2-methylphenyl) (4-methylpiperazine-1-yl) methanone;

$82)_3$-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-N-(2-(dimethylamino)ethyl)-2-methylbenzamide;

83) (3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-2-methylphenyl) (morpholino) methanone;

84)N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-2-methylphenyl)-2-(dimethylamino) acetamide;

85)N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-2-methylphenyl)-2-morpholinoacetamide;

86)N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-2-methylphenyl)-3-(dimethylamino) propanamide;

87)N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-2-methylphenyl)-2-(4-methylpiperazine-1-yl) acetamide;

88)N-(3-(3-(6-bromo-7-((3-sulfamoylphenyl)amino)-1H-imidazo[4,5-b]pyridine-2-yl)-2,5-dimethyl-1H-pyrrol-1-yl)-4-methylphenyl)-2-morpholinoacetamide;

89)N-(3-(3-(6-bromo-7-((3-sulfamoylphenyl)amino)-1H-imidazo[4,5-b]pyridine-2-yl)-2,5-dimethyl-1H-pyrrol-1-yl)-4-methylphenyl)-2-(4-methylpiperazine-1-yl) acetamide;

90)N-(3-(3-(6-bromo-7-((3-sulfamoylphenyl)amino)-1H-imidazo[4,5-b]pyridine-2-yl)-2,5-dimethyl-1H-pyrrol-1-yl)-4-methylphenyl)-2-(dimethylamino) acetamide;

91) (3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-4-methylphenyl) (morpholino) methanone;

92) (3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-4-methylphenyl) (4-methylpiperazine-1-yl) methanone;

$93)_3$-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-N-(2-(dimethylamino)ethyl)-4-methylbenzamide;

$94)_3$-((6-bromo-2-(2,5-dimethyl-1-(2-methyl-5-(morpholine-4-carbonyl)phenyl)-1H-pyrrol-3-yl)-1H-imidazo[4,5-b]pyridine-7-yl)amino)benzenesulfonamide;

$95)_3$-((6-bromo-2-(2,5-dimethyl-1-(2-methyl-5-(4-methylpiperazine-1-carbonyl)phenyl)-1H-pyrrol-3-yl)-1H-imidazo[4,5-b]pyridine-7-yl)amino)benzenesulfonamide;

$96)_3$-(3-(6-bromo-7-((3-sulfamoylphenyl)amino)-1H-imidazo[4,5-b]pyridine-2-yl)-2,5-dimethyl-1H-pyrrol-1-yl)-N-(2-(dimethylamino)ethyl)-4-methylbenzamide;

97) (4-(3-(6-bromo-7-(((S)-1-(ethylsulfonyl) pyrrolidine-3-yl)amino)-3H-imidazo[4,5-b]pyridine-2-yl)-2,5-dimethyl-1H-pyrrol-1-yl)-3-methylphenyl) (4-methylpiperazine-1-yl) methanone;

98) (4-(3-(6-bromo-7-(((S)-1-(ethylsulfonyl) pyrrolidine-3-yl)amino)-3H-imidazo[4,5-b]pyridine-2-yl)-2,5-dimethyl-1H-pyrrol-1-yl)-3-methylphenyl) (morpholino) methanone.

According to yet another embodiment of the present disclosure, there is provided a pharmaceutical composition for preventing or treating diseases selected from the group consisting of cancer, degenerative brain disease, non-alcoholic fatty liver disease, and influenza, wherein the pharmaceutical composition contains the compound represented by Formula 1, a stereoisomer thereof, a solvate thereof, a hydrate thereof, or a pharmaceutically acceptable salt thereof as an active ingredient.

The compound may inhibit protein kinase activity.

The protein kinase may be at least one selected from the group consisting of MLK1, MLK2, MLK3, MLK4, DLK, LZK, ZAK and LRRK2.

The cancer may be at least one selected from the group consisting of pseudomyxoma, intrahepatic cholangiocarcinoma, hepatoblastoma, liver cancer, thyroid cancer, colon cancer, testicular cancer, myelodysplastic syndrome, glioblastoma, oral cancer, lip cancer, mycosis fungoides, acute myelogenous leukemia, acute lymphocytic leukemia, basal cell carcinoma, ovarian epithelial cancer, ovarian germ cell carcinoma, male breast cancer, brain cancer, pituitary adenoma, multiple myeloma, gallbladder cancer, biliary cancer, colon cancer, chronic myelogenous leukemia, chronic lymphocytic leukemia, retinoblastoma, choroidal melanoma, diffuse large B cell lymphoma, ampulla of Vater cancer, bladder cancer, peritoneal cancer, parathyroid cancer, adrenal gland cancer, sinunasal cancer, non-small cell lung cancer, non-Hodgkin's lymphoma, tongue cancer, astrocytoma, small cell lung cancer, pediatric brain cancer, pediatric lymphoma, childhood leukemia, small bowel cancer, meningioma, esophagus cancer, glioma, neuroblastoma, renal cancer, kidney cancer, heart cancer, duodenal cancer, malignant soft tissue tumor, malignant bone cancer, malignant lymphoma, malignant mesothelioma, malignant melanoma, eye cancer, vulvar cancer, ureteral cancer, urethral cancer, cancer of unknown primary site, gastric lymphoma, gastric cancer, gastric carcinoid, gastrointestinal stromal cancer, Wilms' tumor, breast cancer, sarcoma, penile cancer, pharyngeal cancer, getstational trophoblatic disease, cervical cancer, endometrial cancer, uterine sarcoma, prostate cancer, metastatic bone cancer, metastatic brain cancer, mediastinal cancer, rectal cancer, rectal carcinoid, vaginal cancer, spinal cord cancer, vestibular schwannoma, pancreatic cancer, salivary gland cancer, Kaposi's sarcoma, Paget's disease, tonsil cancer, squamous cell carcinoma, adenocarcinoma of lung, lung cancer, squamous cell carcinoma of lung, skin cancer, anal cancer, rhabdomyosarcoma, laryngeal cancer, pleural cancer, and thymus cancer.

The degenerative brain disease may be at least one selected from the group consisting of Alzheimer's disease, Down syndrome, Parkinson's disease, Lou Gehrig's disease, dementia, Huntington's disease, multiple sclerosis, proximal lateral sclerosis, apoplexy, stroke and mild cognitive impairment.

The non-alcoholic fatty liver disease may be at least one selected from the group consisting of non-alcoholic fatty liver, non-alcoholic steatohepatitis, cirrhosis and liver cancer.

The influenza may be influenza A or influenza B.

Advantageous Effects

A novel imidazopyridine derivative compound and pharmaceutically acceptable salt thereof according to the present disclosure have excellent activity against protein kinase. Accordingly, a pharmaceutical composition containing the same as an active ingredient can be usefully used for preventing or treating protein kinase-related diseases.

In particular, it can be effectively used for prevention, treatment or improvement of cancer, degenerative brain disease, non-alcoholic fatty liver disease or influenza.

BRIEF DESCRIPTION OF THE DRAWINGS

FIG. 1 is a photograph showing the results of an MLK3 activity inhibition experiment of a compound according to an embodiment of the present disclosure.

FIG. 2 is a graph showing the results of a cancer cell proliferation inhibitory activity according to a concentration of the compound according to an embodiment of the present disclosure.

FIG. 3 is a photograph showing the results of a cancer cell metastasis inhibition activity of the compound according to an embodiment of the present disclosure.

FIG. 4 is a graph showing a comparison of the ALT evaluation results for the animal group of the experimental example of the present disclosure.

FIG. 5 is a graph showing a comparison of the AST evaluation results for the animal group of the experimental example of the present disclosure.

FIG. 6 is a graph showing a comparison of fibrosis area evaluation results for the animal group of the experimental example of the present disclosure.

FIG. 7 is a graph showing the results of inhibition of LRRK2 phosphorylation for the example and comparative compounds of the present disclosure.

FIG. 8 is a graph showing a comparison of the neuronal damage protective effect of the example and comparative compounds of the present disclosure.

FIG. 9 is a graph showing a comparison of the antiviral effect of the negative control group and the examples of the present disclosure.

FIG. 10 is a graph showing a comparison of the antiviral effect of the negative control group and the examples of the present disclosure.

FIG. 11 is a graph showing a comparison of the antiviral effect of the negative control group and the examples of the present disclosure.

FIG. 12 is a graph showing a comparison of the antiviral effect of the negative control group and the examples of the present disclosure.

FIG. 13 is a graph showing a comparison of the antiviral effect of the negative control group and the examples of the present disclosure.

FIG. 14 is a graph showing a comparison of the antiviral effect of the negative control group and the examples of the present disclosure.

FIG. 15 is a graph showing the change in body weight as a result of an antiviral experiment of a compound according to an embodiment of the present disclosure.

FIG. 16 is a graph showing the survival rate as a result of an antiviral experiment of a compound according to an embodiment of the present disclosure.

DESCRIPTION OF EXEMPLARY EMBODIMENTS

The present disclosure may be understood more readily by reference to the following detailed description of the preferred embodiments of the present disclosure and the examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular form includes plural references unless indicated otherwise. For example, "a" substituent includes one or more substituents.

The present disclosure described herein suitably may be practiced in the absence of any element(s) not specifically disclosed herein. Thus, for example, in each instance herein any of the terms "comprising", "consisting essentially of", and "consisting of" may be replaced with either of the other two terms As used herein, the term "halo" or "halogen" refers to fluorine (F), chlorine (Cl), bromine (Br) or iodine (I), unless otherwise specified.

As used herein, the term "alkyl" refers to a saturated, monovalent aliphatic hydrocarbon radical including straight chain and branched chain groups having the specified number of carbon atoms, unless otherwise specified. Alkyl groups typically contain 1 to 20 carbon atoms ("$C_1$-$C_{20}$ alkyl"), preferably 1 to 12 carbon atoms ("$C_1$-$C_{12}$ alkyl"), more preferably 1 to 8 carbon atoms ("$C_1$-cs alkyl"), or 1 to 6 carbon atoms ("$C_1$-$C_6$ alkyl"), or 1 to 4 carbon atoms ("$C_1$-$C_4$ alkyl"). Examples of alkyl groups include methyl, ethyl, n-propyl, isopropyl, n-butyl, iso-butyl, tert-butyl, n-pentyl, isopentyl, neopentyl, n-hexyl, n-heptyl, n-octyl and the like. Alkyl groups may be substituted or unsubstituted. In particular, unless otherwise specified, alkyl groups may be substituted by one or more halo groups, up to the total number of hydrogen atoms present on the alkyl moiety. Thus, $C_1$-$C_4$ alkyl includes halogenated alkyl groups, and for example, fluorinated alkyl groups, having 1 to 4 carbon atoms, e.g., trifluoromethyl ($—CF_3$) or difluoroethyl ($—CH_2CHF_2$).

Alkyl groups described herein as optionally substituted may be substituted by one or more substituent groups, which are selected independently unless otherwise indicated. The total number of substituent groups may equal the total number of hydrogen atoms on the alkyl moiety, to the extent such substitution makes chemical sense. Optionally substituted alkyl groups typically contain from 1 to 6 optional substituents, sometimes 1 to 5 optional substituents, preferably from 1 to 4 optional substituents, or more preferably from 1 to 3 optional substituents.

Optional substituent groups suitable for alkyl include, but are not limited to $C_1$-$C_8$ alkyl, $C_2$-$C_8$ akenyl, $C_2$-$C_8$ akynyl, $C_3$-$C_8$ cycloalkyl, 3-12 membered heterocyclyl, $C_6$-$C_{12}$ aryl and 5-12 membered heteroaryl, halo, =O (oxo), =S (thiono), =N—CN, =N—$OR^x$, =NR, —CN, —C(O) $R^x$, —$CO_2R^x$, —C(O) $NR^xR^y$, —$SR^x$, —$SOR^x$, —$SO_2R$, —$SO_2NR^xR^y$, —$NO_2$, —$NR^xR^y$, —$NR^x$C(O) $R^Y$, —$NR^x$C(O) $NR^xR^y$, —$NR^X$C(O)$OR^x$, —$NR^xSO_2R^y$, —$NR^xSO_2NR^xR^y$, —OR, —OC(O) $R^x$ and —OC(O) $NR^xR^y$; wherein each $R^x$ and $R^y$ is independently hydrogen (H), $C_1$-$C_8$ alkyl, $C_1$-$C_8$ acyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl, or 5-12 membered heteroaryl, or $R^x$ and $R^y$ may be taken together with the N atom to which they are attached to form a 3-12 membered heterocyclyl or 5-12 membered heteroaryl ring, each optionally containing 1, 2 or 3 additional heteroatoms selected from O, N and S(O), where q is 0-2; each $R^x$ and $R^y$ is optionally substituted with 1 to 3 substituents independently selected from the group consisting of halo, =O, =S, =N—CN, =N—OR', =NR', —CN, —C(O) R', —$CO_2$R', —C(O) NR'2, —SOR', —$SO_2$R', —$SO_2$NR'2, —$NO_2$, —NR'2, —NR'C(O) R', —NR'C(O) NR'2, —NR'C (O) OR', —NR'$SO_2$R', —NR'$SO_2$NR'2, —OR', —OC(O) R' and —OC(O) NR'2, wherein each R' is independently hydrogen (H), $C_1$-$C_8$ alkyl, $C_1$-$C_8$ acyl, $C_2$—$C_8$ alkenyl, $C_2$-$C_8$ alkynyl, $C_3$-$C_8$ cycloalkyl, 3-12 membered heterocyclyl, $C_6$-$C_{12}$ aryl, or $C_5$-$C_{12}$ heteroaryl; and wherein each said $C_1$-$C_8$ alkyl, $C_2$-$C_8$ akenyl, $C_2$-$C_8$ akynyl, $C_3$-$C_8$ cycloalkyl, 3-12 membered heterocyclyl, $C_6$-$C_{12}$ aryl and 5-12 membered heteroaryl is optionally substituted as further defined herein.

Optionally substituted alkyl groups are specifically named by reference to the substituent group.

For example, as used herein, the term "haloalkyl" refers to an alkyl group having the specified number of carbon atoms that is substituted by one or more halo substituents, and typically contain 1-6 carbon atoms, or preferably 1-4 carbon atoms or 1-2 carbon atoms and 1, 2 or 3 halo atoms (i.e., "$C_1$-$C_6$ haloalkyl", $C_1$-$C_4$ haloalkyl" or $C_1$-$C_2$ haloalkyl"), unless otherwise specified. For example, fluorinated alkyl groups may be specifically referred to as fluoroalkyl groups, e.g., $C_1$-$C_6$, $C_1$-$C_4$ or $C_1$-$C_2$ fluoroalkyl groups, which are typically substituted by 1, 2 or 3 fluoro atoms. Thus, a $C_1$-$C_4$ fluoroalkyl includes trifluoromethyl ($—CF_3$), difluoromethyl ($—CF_2H$), fluoromethyl ($—CFH_2$), difluoroethyl ($—CH_2CF_2H$), and the like.

As used herein, the term "hydroxyalkyl" refers to an alkyl group having the specified number of carbon atoms that is substituted by one or more hydroxy substituents, and typically contain 1-6 carbon atoms, preferably 1-4 carbon atoms, and 1, 2 or 3 hydroxy (i.e., "$C_1$-$C_6$ hydroxyalkyl"), unless otherwise specified. Thus, $C_1$-$C_6$ hydroxyalkyl includes hydroxymethyl ($—CH_2OH$) and 2-hydroxyethyl ($—CH_2CH_2OH$).

As used herein, the term "alkoxyalkyl" refers to an alkyl group having the specified number of carbon atoms that is substituted by one or more alkoxy substituents, unless otherwise specified. Alkoxyalkyl groups typically contain 1-6 carbon atoms in the alkyl portion and are substituted by 1, 2 or 3 $C_1$-$C_4$ alkyloxy substituents. Such groups are sometimes described herein as $C_1$-$C_4$ alkyloxy-$C_1$-$C_6$ alkyl.

As used herein, the term "aminoalkyl" refers to alkyl group having the specified number of carbon atoms that is substituted by one or more substituted or unsubstituted amino groups, as such groups are further defined herein, unless otherwise specified. Aminoalkyl groups typically contain 1-6 carbon atoms in the alkyl portion and are substituted by 1, 2 or 3 amino substituents. Thus, a $C_1$-$C_6$ aminoalkyl includes, for example, aminomethyl ($—CH_2NH_2$), N,N-dimethylaminoethyl ($—CH_2CH_2N(CH_3)_2$), 3-(N-cyclopropylamino) propyl ($—CH_2CH_2CH_2NH$-$^c$Pr) and N-pyrrolidinylethyl ($—CH_2CH_2$—N-pyrrolidinyl).

As used herein, the term "alkenyl" refers to an alkyl group, as defined herein, consisting of at least two carbon atoms and at least one carbon-carbon double bond, unless otherwise specified. Typically, alkenyl groups have 2 to 20 carbon atoms ("$C_2$-$C_{20}$ alkenyl"), preferably 2 to 12 carbon atoms ("$C_2$-$C_{12}$ alkenyl"), more preferably 2 to 8 carbon atoms ("$C_2$-$C_8$ alkenyl"), or 2 to 6 carbon atoms ("$C_2$-$C_6$ alkenyl"), or 2 to 4 carbon atoms ("$C_2$-$C_4$ alkenyl"). Accordingly, alkenyl includes, for example, ethenyl, 1-propenyl, 2-propenyl, 1-, 2-, or 3-butenyl, and the like. Alkenyl groups are unsubstituted or substituted by the same groups that are described herein as suitable for alkyl.

As used herein, the term "alkynyl" refers to an alkyl group, as defined herein, consisting of at least two carbon atoms and at least one carbon-carbon triple bond, unless otherwise specified. Alkynyl groups have 2 to 20 carbon atoms ("$C_2$-$C_{20}$ alkynyl"), preferably 2 to 12 carbon atoms ("$C_2$-$C_{12}$ alkynyl"), more preferably 2 to 8 carbon atoms ("$C_2$-$C_8$ alkynyl"), or 2 to 6 carbon atoms ("$C_2$-$C_6$ alkynyl"), or 2 to 4 carbon atoms ("$C_2$-$C_4$ alkynyl"). Representative examples include, but are not limited to, ethynyl, 1-propynyl, 2-propynyl, 1-, 2-, or 3-butynyl, and the like. Alkynyl groups are unsubstituted or substituted by the same groups that are described herein as suitable for alkyl.

As used herein, the term "alkylene" refers to a divalent hydrocarbyl group having the specified number of carbon atoms which can link two other groups together, unless otherwise specified. Sometimes it refers to a group $-(CH_2)_n-$where n is 1-8, and preferably n is 1-4. Where specified, an alkylene can also be substituted by other groups and may include one or more degrees of unsaturation (i.e., an alkenylene or alkynlene moiety) or rings. The open valences of an alkylene need not be at opposite ends of the chain. Thus, branched alkylene groups such as —CH (Me)-, —$CH_2$CH (Me)- and —$C(Me)_2$— are also included within the scope of the term 'alkylenes', as are cyclic groups such as cyclopropan-1,1-diyl and unsaturated groups such as ethylene (—CH═CH—) or propylene (—$CH_2$—CH═CH—). An alkylene group is substituted or unsubstituted by the same groups as described herein as suitable for alkyl.

As used herein, the term "heteroalkylene" refers to an alkylene group as described above, wherein one or more non-contiguous carbon atoms of the alkylene chain are replaced by —N(R)—, —O— or —S(O)—, where R is hydrogen (H) or a suitable substituent group and x is 0-2, unless otherwise specified. For example, the group —O—$(CH_2)_{1-4}$— is a '$C_2$-$C_5$'-heteroalkylene group, where one of the carbon atoms of the corresponding alkylene is replaced by O. A heteroalkylene group is substituted or unsubstituted by the same groups as described herein as suitable for alkyl.

As used herein, the term "alkoxy" refers to a monovalent-O-alkyl group, wherein the alkyl portion has the specified number of carbon atoms, unless otherwise specified. Alkoxy groups typically contain 1 to 8 carbon atoms ("$C_1$-$C_8$ alkoxy"), or 1 to 6 carbon atoms ("$C_1$-$C_6$ alkoxy"), or 1 to 4 carbon atoms ("$C_1$-$C_4$ alkoxy"). For example, $C_1$-$C_4$ alkoxy includes methoxy (—$OCH_3$), ethoxy (—$OCH_2CH_3$), isopropoxy (—$OCH(CH_3)_2$), tert-butyloxy (—$OC(CH_3)_3$), and the like. Alkoxy groups are unsubstituted or substituted on the alkyl portion by the same groups that are described herein as suitable for alkyl. In particular, alkoxy groups may be optionally substituted by one or more halo atoms, and in particular one or more fluoro atoms, up to the total number of hydrogen atoms present on the alkyl portion. Such groups are referred to as "haloalkoxy" (for example, where fluorinated, more specifically as "fluoroalkoxy") groups having the specified number of carbon atoms and substituted by one or more halo substituents, Typically such groups contain from 1-6 carbon atoms, preferably 1-4 carbon atoms, and sometimes 1-2 carbon atoms, and 1, 2 or 3 halo atoms (i.e., "$C_1$-$C_6$ haloalkoxy", "$C_1$-$C_4$ haloalkoxy" or "$C_1$-$C_2$ haloalkoxy"). More specifically, fluorinated alkyl groups may be specifically referred to as fluoroalkoxy groups, e.g., $C_1$-$C_6$, $C_1$-$C_4$ or $C_1$-$C_2$ fluoroalkoxy groups, which are typically substituted by 1, 2 or 3 fluoro atoms. Thus, a $C_1$-$C_4$ fluoroalkoxy includes trifluoromethyloxy (—$OCF_3$), difluoromethyloxy (—$OCF_2H$), fluoromethyloxy (—$OCFH_2$), difluoroethyloxy (—$OCH_2CF_2H$), and the like.

As used herein, the term "thioalkoxy" refers to a monovalent-S-alkyl group, wherein the alkyl portion has the specified number of carbon atoms, and is optionally substituted on the alkyl portion by the same groups that are described herein as suitable for alkyl, unless otherwise specified. For example, a $C_1$-$C_4$ thioalkoxy includes —$SCH_3$ and —$SCH_2CH_3$.

As used herein, the term "cycloalkyl" refers to a non-aromatic, saturated or partially unsaturated carbocyclic ring system containing the specified number of carbon atoms, which may be a monocyclic, spirocyclic, bridged or fused bicyclic or polycyclic ring system that is connected to the base molecule through a carbon atom of the cycloalkyl ring, unless otherwise specified. Typically, the cycloalkyl groups of the present disclosure contain 3 to 12 carbon atoms ("$C_3$-$C_{12}$ cycloalkyl"), preferably 3 to 8 carbon atoms ("$C_3$-$C_8$ cycloalkyl"). Representative examples include, e.g., cyclopropane, cyclobutane, cyclopentane, cyclopentene, cyclohexane, cyclohexene, cyclohexadiene, cycloheptane, cycloheptatriene, adamantane, and the like. Cycloalkyl groups are unsubstituted or substituted by the same groups that are described herein as suitable for alkyl.

As used herein, the term "cycloalkylalkyl" is used to describe a cycloalkyl ring, typically a $C_3$-$C_8$ cycloalkyl, which is connected to the base molecule through an alkylene linker, typically a $C_1$-$C_4$ alkylene. Cycloalkylalkyl groups are sometimes described by the total number of carbon atoms in the carbocyclic ring and linker, and typically contain from 4-12 carbon atoms ("$C_4$-$C_{12}$ cycloalkylalkyl"), unless otherwise specified. Thus, a cyclopropylmethyl group is a $C_4$-cycloalkylalkyl group and a cyclohexylethyl is a $C_8$-cycloalkylalkyl. Cycloalkylalkyl groups are unsubstituted or substituted on the cycloalkyl and/or alkylene portions by the same groups that are described herein as suitable for alkyl groups. Sometimes cycloalkylalkyl groups are described herein, as -L-$C_3$-$C_8$-cycloalkyl, where the cycloalkyl group has the number of carbon atoms indicated and -L- refers to an alkylene linker. It will be understood that when -L- is a bond, the group is cycloalkyl.

As used herein, the terms "heterocyclyl", "heterocyclic" or "heteroalicyclic" are used interchangeably herein to refer to a non-aromatic, saturated or partially unsaturated ring system containing the specified number of ring atoms, including at least one heteroatom selected from N, O and S as a ring member, where ring S atoms are optionally substituted by one or two oxo groups (i.e., S(O), where x is 0, 1 or 2) and where the heterocyclic ring is connected to the base molecule via a ring atom, which may be C or N, unless otherwise specified. Heterocyclic rings include rings which are spirocyclic, bridged, or fused to one or more other heterocyclic or carbocyclic rings, where such spirocyclic, bridged, or fused rings may themselves be saturated, partially unsaturated or aromatic to the extent unsaturation or aromaticity makes chemical sense, provided the point of attachment to the base molecule is an atom of the heterocyclic portion of the ring system. Preferably, heterocyclic rings contain 1 to 4 heteroatoms selected from N, O, and $S(O)_q$ as ring members, and more preferably 1 to 2 ring heteroatoms, provided that such heterocyclic rings do not contain two contiguous oxygen atoms. Heterocyclyl groups are unsubstituted or substituted by suitable substituent groups, for example the same groups that are described herein as suitable for alkyl, aryl or heteroaryl. Such substituents may be present on the heterocyclic ring attached to the base molecule, or on a spirocyclic, bridged or fused ring attached thereto. In addition, ring N atoms are optionally substituted by groups suitable for an amine, e.g., alkyl, acyl, carbamoyl, sulfonyl substituents, and the like.

Heterocycles typically include 3-12 membered heterocyclyl groups, preferably 3-10 membered heterocyclyl groups, and more preferably 5-6 membered heterocyclyl groups, in accordance with the definition herein.

In various embodiments, heterocyclic groups contain 3-12 ring members, including both carbon and non-carbon heteroatoms, and preferably 4-7 ring members. In certain preferred embodiments, substituent groups comprising 3-12 membered heterocycles are selected from azetidinyl, pyrrolidinyl, piperidinyl, piperazinyl, azepanyl, diazepanyl, tetrahydrofuranyl, tetrahydropyranyl, tetrahydrothiophenyl, tetrahydrothiopyranyl, morpholinyl and thiomorpholinyl rings, each of which are optionally substituted as described for the particular substituent group, to the extent such substitution makes chemical sense.

It is understood that no more than two N, O or S atoms are ordinarily connected sequentially, except where an oxo group is attached to N or S to form a nitro or sulfonyl group, or in the case of certain heteroaromatic rings, such as triazine, triazole, tetrazole, oxadiazole, thiadiazole, and the like.

As used herein, the term "heterocyclylalkyl" may be used to describe a heterocyclic group of the specified size that is connected to the base molecule through an alkylene linker of the specified length, unless otherwise specified. Typically, such groups contain an optionally substituted 3-12 membered heterocycle attached to the base molecule through a $C_1$-$C_4$ alkylene linker. Where so indicated, such groups are optionally substituted on the alkylene portion by the same groups that are described herein as suitable for alkyl groups and on the heterocyclic portion by groups described as suitable for heterocyclic rings. Sometimes heterocyclylalkyl groups are described herein as -L-heterocyclylalkyl, where the heterocyclylalkyl group has the number of ring atoms indicated and -L- refers to an alkylene linker. It will be understood that when -L- is a bond, the group is heterocyclyl.

As used herein, the term "aryl" or "aromatic" refers to an optionally substituted monocyclic or fused bicyclic or polycyclic ring system having the well-known characteristics of aromaticity, wherein at least one ring contains a completely conjugated pi-electron system, unless otherwise specified. Typically, aryl groups contain 6 to 20 carbon atoms ("$C_5$-$C_{20}$ aryl") as ring members, preferably 6 to 14 carbon atoms ("$C_6$-$C_{14}$ aryl") or more preferably, 6 to 12 carbon atoms ("$C_6$-$C_{12}$ aryl"). Fused aryl groups may include an aryl ring (e.g., a phenyl ring) fused to another aryl or heteroaryl ring, or fused to a saturated or partially unsaturated carbocyclic or heterocyclic ring, provided the point of attachment to the base molecule on such fused ring systems is an atom of the aromatic portion of the ring system. For example, aryl groups include phenyl, biphenyl, naphthyl, anthracenyl, phenanthrenyl, indanyl, indenyl, and tetrahydronaphthyl. The aryl group is unsubstituted or substituted as further described herein.

As used herein, the term "heteroaryl" or "heteroaromatic" refers to monocyclic or fused bicyclic or polycyclic ring systems having the well-known characteristics of aromaticity that contain the specified number of ring atoms and include at least one heteroatom selected from N, O and S as a ring member in an aromatic ring, unless otherwise specified. The inclusion of a heteroatom permits aromaticity in 5-membered rings as well as 6-membered rings. Typically, heteroaryl groups contain 5 to 20 ring atoms ("5-20 membered heteroaryl"), preferably 5 to 14 ring atoms ("5-14 membered heteroaryl"), and more preferably 5 to 12 ring atoms ("5-12 membered heteroaryl"). Heteroaryl rings are attached to the base molecule via a ring atom of the heteroaromatic ring, such that aromaticity is maintained. Thus, 6-membered heteroaryl rings may be attached to the base molecule via a ring C atom, while 5-membered heteroaryl rings may be attached to the base molecule via a ring C or N atom. Heteroaryl groups may also be fused to another aryl or heteroaryl ring, or fused to a saturated or partially unsaturated carbocyclic or heterocyclic ring, provided the point of attachment to the base molecule on such fused ring systems is an atom of the heteroaromatic portion of the ring system. Examples of unsubstituted heteroaryl groups include pyrrole, furan, thiophene, pyrazole, imidazole, isoxazole, oxazole, isothiazole, thiazole, triazole, oxadiazole, thiadiazole, tetrazole, pyridine, pyridazine, pyrimidine, pyrazine, benzofuran, benzothiophene, indole, benzimidazole, indazole, quinoline, isoquinoline, purine, triazine, naphthryidine and carbazole. In various embodiments, 5- or 6-membered heteroaryl groups are selected from the group consisting of pyrrolyl, furanyl, thiophenyl, pyrazolyl, imidazolyl, isoxazolyl, oxazolyl, isothiazolyl, thiazolyl, triazolyl, pyridinyl and pyrimidinyl, pyrazinyl or pyridazinyl rings. The heteroaryl group is unsubstituted or substituted as further described herein.

Aryl, heteroaryl and heterocyclyl moieties described herein as optionally substituted may be substituted by one or more substituent groups, which are selected independently unless otherwise indicated. The total number of substituent groups may equal the total number of hydrogen atoms on the aryl, heteroaryl or heterocyclyl moiety, to the extent such substitution makes chemical sense and aromaticity is maintained in the case of aryl and heteroaryl rings. Optionally substituted aryl, heteroaryl or heterocyclyl groups typically contain from 1 to 5 optional substituents, sometimes 1 to 4 optional substituents, preferably 1 to 3 optional substituents, or more preferably from 1-2 optional substituents.

Optional substituent groups suitable for aryl, heteroaryl and heterocyclyl rings include, but are not limited to: $C_1$-$C_8$ alkyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl and 5-12 membered heteroaryl; and halo, ═O (iodine), ═S (thiono), ═N—CN, ═N—OR$^x$, ═NR$^x$, —CN, —C(O) R$^x$, —CO$_2$R$^x$, —C(O) NR$^x$R$^y$, —SR$^x$, —SOR$^x$, —SO$_2$R$^x$, —SO$_2$NR$^x$R$^y$, —NO$_2$, —NR$^x$R$^y$, —NR$^x$C(O) R$^y$, —NR$^x$C(O) NR$^x$R$^y$, —NR$^x$C(O) OR$^x$, —NR$^x$SO$_2$R$^y$, —NR$^x$SO$_2$NR$^x$R$^y$, —OR$^x$, —OC(O) R$^x$ and —OC(O) NR$^x$R$^y$; where each R$^x$ and R$^y$ is independently hydrogen (H), $C_1$-$C_8$ alkyl, $C_1$-$C_8$ acyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl, or 5-12 membered heteroaryl, or Rand R$^y$ may be taken together with the N atom to which they are attached to form a 3-12 membered heterocyclyl or 5-12 membered heteroaryl, each optionally containing 1, 2 or 3 additional heteroatoms selected from O, N and S(O), where q is 0-2; each R$^x$ and R$^y$ is optionally substituted with 1 to 3 substituents independently selected from the group consisting of halo, ═O, ═S, ═N—CN, ═N—OR', ═NR', —CN, —C(O) R', —CO$_2$R', —C(O) NR'2, —SR', —SOR', —SO$_2$R', —SO$_2$NR'2, —NO$_2$, —NR'2, —NR'C(O) R', —NR'C(O) NR'2, —NR'C(O) OR', —NR'SO$_2$R', —NR'SO$_2$NR'2, —OR', —OC(O) R' and —OC(O) NR'2, wherein each R' is independently hydrogen (H), $C_1$-$C_8$ alkyl, $C_1$-$C_8$ acyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl, or 5-12 membered heteroaryl; and each said $C_1$-$C_8$ alkyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl and 5-12 membered heteroaryl is optionally substituted as further defined herein.

As used herein, the term "arylalkyl" group refers to an aryl group as described herein which is linked to the base molecule through an alkylene or similar linker. Arylalkyl groups are described by the total number of carbon atoms in the ring and linker. Thus a benzyl group is a $C_7$-arylalkyl group and a phenylethyl is a $C_8$-arylalkyl. Typically, arylalkyl groups contain 7-16 carbon atoms ("$C_7$-$C_{16}$ arylalkyl"), wherein the aryl portion contains 6-12 carbon atoms and the alkylene portion contains 1~4 carbon atoms. Such groups may also be represented as —$C_1$-$C_4$ alkylene-$C_6$-$C_{12}$ aryl.

As used herein, the term "heteroarylalkyl" refers to a heteroaryl group as described above that is attached to the base molecule through an alkylene linker, and differs from "arylalkyl" in that at least one ring atom of the aromatic moiety is a heteroatom selected from N, O and S. Heteroarylalkyl groups are sometimes described herein according to the total number of non-hydrogen atoms (i.e., C, N, S and O atoms) in the ring and linker combined, excluding substituent groups. Thus, for example, pyridinylmethyl may be referred to as a "$C_7$"-heteroarylalkyl. Typically, unsubstituted heteroarylalkyl groups contain 6-20 non-hydrogen atoms (including C, N, S and O atoms), wherein the heteroaryl portion typically contains 5-12 atoms and the alkylene portion typically contains 1~4 carbon atoms. Such groups may also be represented as —$C_1$-$C_4$ alkylene-5-12 membered heteroaryl. Sometimes heteroarylalkyl groups are described herein as -L-heteroarylalkyl, where the heteroarylalkyl group has the number of ring atoms indicated and -L- refers to an alkylene linker. It will be understood that when -L- is a bond, the group is heteroaryl.

As used herein, the terms "arylalkoxy" and "heteroarylalkoxy" refer to aryl and heteroaryl groups, attached to the base molecule through a heteroalkylene linker (i.e., —O-alkylene-), wherein the groups are described according to the total number of non-hydrogen atoms (i.e., C, N, S and O atoms) in the ring and linker combined, unless otherwise specified. Thus, —O—$CH_2$-phenyl and —O—$CH_2$-pyridinyl groups would be referred to as $C_8$-arylalkoxy and $C_8$-heteroarylalkoxy groups, respectively.

Where an arylalkyl, arylalkoxy, heteroarylalkyl or heteroarylalkoxy is described as optionally substituted, the substituents may be on either the divalent linker portion or on the aryl or heteroaryl portion of the group. The substituents optionally present on the alkylene or heteroalkylene portion are the same as those described above for alkyl or alkoxy groups generally, while the substituents optionally present on the aryl or heteroaryl portion are the same as those described above for aryl or heteroaryl groups generally.

As used herein, the term "hydroxy" refers to an —OH group, unless otherwise specified.

As used herein, the term "acyloxy" refers to a monovalent group —OC(O)alkyl, wherein the alkyl portion has the specified number of carbon atoms (typically $C_1$-$C_8$, preferably $C_1$-$C_6$ or $C_1$-$C_4$) that are optionally substituted by groups suitable for alkyl, unless otherwise specified. Thus, $C_1$-$C_4$ acyloxy includes an —OC(O) $C_1$-$C_4$ alkyl substituent, e.g., —OC(O) $CH_3$.

As used herein, the term "acyl" refers to a monovalent group —C(O)alkyl, wherein the alkyl portion has the specified number of carbon atoms (typically $C_1$-$C_8$, preferably $C_1$-$C_8$ or $C_1$-$C_4$) and may be optionally substituted by groups suitable for alkyl, e.g., by F, OH or alkoxy, unless otherwise specified. Thus, optionally substituted-C(O) $C_1$-$C_4$ alkyl includes unsubstituted acyl groups, such as —C(O) $CH_3$ (i.e., acetyl) and —C(O) $CH_2CH_3$ (i.e., propionyl), as well as substituted acyl groups such as —C(O) $CF_3$ (trifluoroacetyl), —C(O) $CH_2OH$ (hydroxyacetyl), —C(O) $CH_2OCH_3$ (methoxyacetyl), —C(O) $CF_2H$ (difluoroacetyl), and the like.

As used herein, the term "acylamino" refers to a monovalent group, —NHC(O)alkyl or —NRC(O)alkyl, wherein the alkyl portion has the specified number of carbon atoms (typically $C_1$-$C_8$, preferably $C_1$-$C_6$ or $C_1$-$C_4$) and is optionally substituted by groups suitable for alkyl, unless otherwise specified. Thus, $C_1$-$C_4$ acylamino includes an —NHC (O) $C_1$-$C_4$ alkyl substituent, e.g., —NHC(O) $CH_3$.

As used herein, the term "aryloxy" or "heteroaryloxy" refer to optionally substituted-O-aryl or —O-heteroaryl, in each case where aryl and heteroaryl are as further defined herein, unless otherwise specified.

As used herein, the term "arylamino" or "heteroarylamino" refer to optionally substituted —NH-aryl, —NR-aryl, —NH-heteroaryl or -NR-heteroaryl, in each case where aryl and heteroaryl are as further defined herein and R represents a substituent suitable for an amine, e.g., an alkyl, acyl, carbamoyl or sulfonyl group, or the like, unless otherwise specified.

As used herein, the term "cyano" refers to a —C≡N group, unless otherwise specified.

As used herein, the term "unsubstituted amino" refers to a group —$NH_2$, unless otherwise specified. Where the amino is described as substituted or optionally substituted, the term includes groups of the form —$NR^xR^y$, where each or $R^x$ and $R^y$ is independently hydrogen (H), alkyl, alkenyl, alkynyl, cycloalkyl, heterocyclyl, acyl, thioacyl, aryl, heteroaryl, cycloalkylalkyl, arylalkyl or heteroarylalkyl, in each case having the specified number of atoms and optionally substituted as described herein. For example, "alkylamino" refers to a group —$NR^xR^y$, wherein one of $R^x$ and $R^y$ is an alkyl moiety and the other is H, and "dialkylamino" refers to —$NR^xR^y$ wherein both of $R^x$ and $R^y$ are alkyl moieties, where the alkyl moieties having the specified number of carbon atoms (e.g., —NH—$C_1$-$C_4$ alkyl or -N($C_1$-$C_4$ alkyl)$_2$). Typically, alkyl substituents on amines contain 1 to 8 carbon atoms, preferably 1 to 6 carbon atoms, or more preferably 1 to 4 carbon atoms. The term also includes forms wherein $R^x$ and $R^y$ are taken together with the N atom to which they are attached to form a 3-12 membered heterocyclyl or 5-12 membered heteroaryl ring, each of which may itself be optionally substituted as described herein for heterocyclyl or heteroaryl rings, and which may contain 1 to 3 additional heteroatoms selected from N, O and S(O), where x is 0-2 as ring members, provided that such rings do not contain two contiguous oxygen atoms.

As used herein, the term "optional" or "optionally" means that the subsequently described event or circumstance may but need not occur, and the description includes instances where the event or circumstance occurs and instances in which it does not.

As used herein, the terms "optionally substituted" and "substituted or unsubstituted" are used interchangeably to indicate that the particular group being described may have no non-hydrogen substituents (i.e., unsubstituted), or the group may have one or more non-hydrogen substituents (i.e., substituted). If not otherwise specified, the total number of substituents that may be present is equal to the number of H atoms present on the unsubstituted form of the group being described. Where an optional substituent is attached via a double bond, such as an oxo (═O) substituent, the group occupies two available valences, so the total number of other substituents that are included is reduced by two. In the case where optional substituents are selected independently from a list of alternatives, the selected groups are the same or different. Throughout the disclosure, it will be understood that the number and nature of optional substituent groups will be limited to the extent that such substitutions make chemical sense.

An embodiment of the present disclosure provides a compound represented by Formula 1 below or pharmaceutically acceptable salt thereof:

[Formula 1]

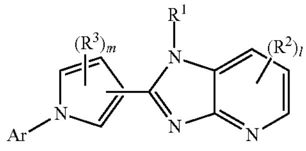

wherein:

Ar is $C_6$-$C_{20}$ aryl or 5 to 20 membered heteroaryl;

$R^1$, $R^2$ and $R^3$ are each, independently of one another, selected from the group consisting of hydrogen, halogen, hydroxy, cyano, nitro, —$SR^a$, —S(═O) $R_a$, —$S(═O)_2R^a$, —$NR^bR^c$, —$CO_2R^b$, —CO—$NR^bR^c$, $C_1$-$C_{20}$ alkyl, $C_1$-$C_6$ haloalkyl, $C_1$-$C_6$ hydroxyalkyl, $C_1$-$C_6$ alkoxyalkyl, $C_1$-$C_6$ aminoalkyl, $C_2$-$C_{20}$ alkenyl, $C_2$-$C_{20}$ alkynyl, $C_1$-$C_8$ alkoxy, $C_3$-$C_{12}$ cycloalkyl, $C_4$-$C_{12}$ cycloalkylalkyl, 3-12 membered heterocyclyl, 3-12 membered heterocyclylalkyl, $C_6$-$C_{20}$ aryl, and 5-20 membered heteroaryl;

the $R_a$, $R_b$ and $R_e$ are each, independently of one another, selected from the group consisting of hydrogen, halogen, hydroxy, cyano, nitro, $C_1$-$C_{20}$ alkyl, $C_1$-$C_6$ haloalkyl, $C_1$-$C_6$ hydroxyalkyl, $C_1$-$C_6$ alkoxyalkyl, $C_1$-$C_6$ aminoalkyl, $C_2$-$C_{20}$ alkenyl, $C_2$-$C_{20}$ alkynyl, $C_1$-$C_8$ alkoxy, $C_3$-$C_{12}$ cycloalkyl, $C_4$-$C_{12}$ cycloalkylalkyl, 3-12 membered heterocyclyl, 3-12 membered heterocyclylalkyl, $C_6$-$C_{20}$ aryl, and 5-20 membered heteroaryl;

the 1 is an integer of 0 to 3; and m is an integer of 0 to 3, wherein the alkyl, haloalkyl, hydroxyalkyl, alkoxyalkyl, aminoalkyl, alkenyl, alkynyl, alkoxy, cycloalkyl, cycloalkylalkyl, heterocyclyl, heterocyclylalkyl, aryl and heteroaryl each may be substituted with one or more substituents selected from the group consisting of hydrogen, halogen, hydroxy, cyano, nitro, —$SR^a$, —S(═O) $R^a$, —$S(═O)_2R^a$, —$NR^bR^c$, —$CO_2R'$, —CO—$NR^bR^c$, $C_1$-$C_{10}$ alkyl, $C_1$-$C_4$ haloalkyl, $C_1$-$C_4$ hydroxyalkyl, $C_1$-$C_4$ alkoxyalkyl, $C_1$-$C_4$ aminoalkyl, $C_2$-$C_{10}$ alkenyl, $C_2$-$C_{10}$ alkynyl, $C_1$-$C_4$ alkoxy, $C_3$-$C_{10}$ cycloalkyl, $C_4$-$C_{10}$ cycloalkylalkyl, 3-10 membered heterocyclyl, 3-10 membered heterocyclylalkyl, $C_6$-$C_{12}$ aryl, and 5-12 membered heteroaryl.

Specifically, the compound represented by Formula 1 above may be represented by Formula 2 below.

[Formula 2]

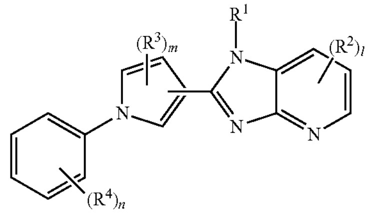

wherein, $R^1$ to $R^3$, 1 and m are the same as defined in Formula 1 above;

$R^4$ is independently of one another, selected from the group consisting of hydrogen, halogen, hydroxy, cyano, nitro, —$SR^a$, —S(═O) $R^a$, —$S(═O)_2R^2$, —$NR^bR^c$, —$CO_2R'$, —CO—$NR^bR^c$, $C_1$-$C_{10}$ alkyl, $C_1$-$C_4$ haloalkyl, $C_1$-$C_4$ hydroxyalkyl, $C_1$-$C_4$ alkoxyalkyl, $C_1$-$C_4$ aminoalkyl, $C_2$-$C_{10}$ alkenyl, $C_2$-$C_{10}$ alkynyl, $C_1$-$C_4$ alkoxy, $C_3$-$C_{10}$ cycloalkyl, $C_4$-$C_{10}$ cycloalkylalkyl, 3-10 membered heterocyclyl, 3-10 membered heterocyclylalkyl, $C_6$-$C_{12}$ aryl, and 5-12 membered heteroaryl, or adjacent groups may be linked to each other to form a ring; and n is an integer of 0 to 5, wherein the alkyl, haloalkyl, hydroxyalkyl, alkoxyalkyl, aminoalkyl, alkenyl, alkynyl, alkoxy, cycloalkyl, cycloalkylalkyl, heterocyclyl, heterocyclylalkyl, aryl and heteroaryl each may be further substituted with one or more substituents selected from the group consisting of hydrogen, halogen, hydroxy, cyano, nitro, —$SR^a$, —S(═O) $R^a$, —$S(═O)_2R^2$, —$NR^bR^c$, —$CO_2R^b$, —CO—$NR^bR^c$, $C_1$-$C_{10}$ alkyl, $C_1$-$C_4$ haloalkyl, $C_1$-$C_4$ hydroxyalkyl, $C_1$-$C_4$ alkoxyalkyl, $C_1$-$C_4$ aminoalkyl, $C_2$-$C_{10}$ alkenyl, $C_2$-$C_{10}$ alkynyl, $C_1$-$C_4$ alkoxy, $C_3$-$C_{10}$ cycloalkyl, $C_4$-$C_{10}$ cycloalkylalkyl, 3-10 membered heterocyclyl, 3-10 membered heterocyclylalkyl, $C_6$-$C_{12}$ aryl, and 5-12 membered heteroaryl.

In addition, specifically, the compound represented by Formula 2 above may be represented by Formula 3 or 4 below.

[Formula 3]

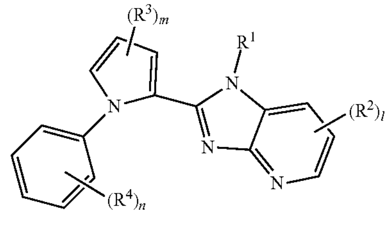

[Formula 4]

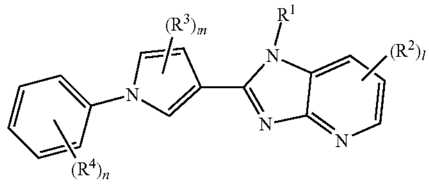

wherein, $R^1$ to $R^4$, 1, m and n are the same as defined in Formula 2 above.

In addition, specifically, the compound represented by Formula 2 above may be represented by Formula 5 below.

[Formula 5]

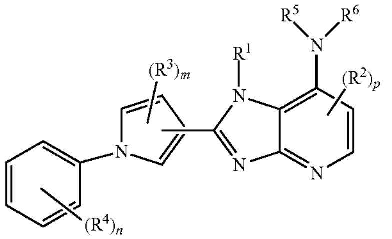

wherein, $R^1$ to $R^4$, 1, m and n are the same as defined in Formula 2 above;

p is an integer from 0 to 2; and $R^5$ and $R^e$ are each, independently of one another, selected from the group consisting of hydrogen, halogen, hydroxy, cyano, nitro, $C_1$-$C_{20}$ alkyl, $C_1$-$C_6$ haloalkyl, $C_1$-$C_6$ hydroxyalkyl, $C_1$ —$C_6$ alkoxyalkyl, $C_1$-$C_6$ aminoalkyl, $C_2$-$C_{20}$ alkenyl, $C_2$-$C_{20}$ alkynyl, $C_1$-$C_8$ alkoxy, $C_3$-$C_{12}$ cycloalkyl, $C_4$-$C_{12}$ cycloalkylalkyl, 3-12 membered heterocyclyl, 3-12 membered heterocyclylalkyl, $C_6$-$C_{20}$ aryl, and 5-20 membered heteroaryl, wherein the alkyl, haloalkyl, hydroxyalkyl, alkoxyalkyl, aminoalkyl, alkenyl, alkynyl, alkoxy, cycloalkyl, cycloalkylalkyl, heterocyclyl, heterocyclylalkyl, aryl and heteroaryl each may be substituted with one or more substituents selected from the group consisting of hydrogen, halogen, hydroxy, cyano, nitro, —$SR^a$, —S(═O) $R^a$, —S(═O)$_2R^a$, —$NR^bR^c$, —$CO_2R^b$, —CO—$NR^bR^c$, $C_1$-$C_{10}$ alkyl, $C_1$-$C_4$ haloalkyl, $C_1$-$C_4$ hydroxyalkyl, $C_1$-$C_4$ alkoxyalkyl, $C_1$-$C_4$ aminoalkyl, $C_2$-$C_{10}$ alkenyl, $C_2$-$C_{10}$ alkynyl, $C_1$-$C_4$ alkoxy, $C_3$-$C_{10}$ cycloalkyl, $C_4$-$C_{10}$ cycloalkylalkyl, 3-10 membered heterocyclyl, 3-10 membered heterocyclylalkyl, $C_6$-$C_{12}$ aryl, and 5-12 membered heteroaryl.

In addition, specifically, the compound represented by Formula 5 above may be represented by Formula 6 or 7 below.

[Formula 6]

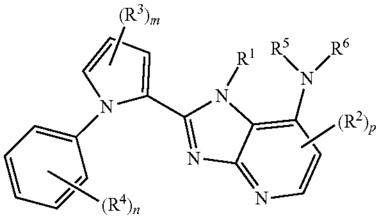

[Formula 7]

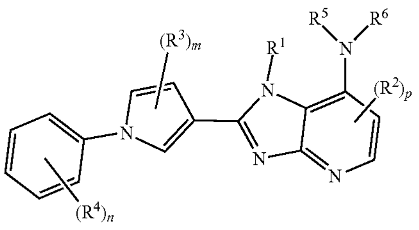

wherein, $R^1$ to $R^{\circ}$, m, n and p are the same as defined in Formula 5 above.

In addition, specifically, the compound represented by Formula 1 may be a compound selected from the group consisting of the following compounds, but is not limited thereto.

1) (S)-6-bromo-2-(2,5-dimethyl-1-(4-morpholinophenyl)-1H-pyrrol-3-yl)-N-(1-(ethylsulfonyl) pyrrolidine-3-yl)-3H-imidazo[4,5-b]pyridine-7-amine;

2) (S)-6-bromo-2-(2,5-dimethyl-1-(3-morpholinophenyl)-1H-pyrrol-3-yl)-N-(1-(ethylsulfonyl) pyrrolidine-3-yl)-3H-imidazo[4,5-b]pyridine-7-amine;

3) (S)-6-bromo-2-(2,5-dimethyl-1-(3-(2-morpholinoethoxy)phenyl)-1H-pyrrol-3-yl)-N-(1-(ethylsulfonyl) pyrrolidine-3-yl)-1H-imidazo[4,5-b]pyridine-7-amine;

4) (S)-6-bromo-2-(2,5-dimethyl-1-(4-(2-morpholinoethoxy)phenyl)-1H-pyrrol-3-yl)-N-(1-(ethylsulfonyl) pyrrolidine-3-yl)-1H-imidazo[4,5-b]pyridine-7-amine;

5) (S)-(4-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)phenyl) (morpholino) methanone;

6) (S)-(3-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)phenyl) (morpholino) methanone;

7)N-(3-(3-(6-bromo-7-(((S)-1-(ethylsulfonyl) pyrrolidine-3-yl)amino)-3H-imidazo[4,5-b]pyridine-2-yl)-2,5-dimethyl-1H-pyrrol-1-yl)-4-methylphenyl) methanesulfonamide;

8)N-(4-(3-(6-bromo-7-(((S)-1-(ethylsulfonyl) pyrrolidine-3-yl)amino)-3H-imidazo[4,5-b]pyridine-2-yl)-2,5-dimethyl-1H-pyrrol-1-yl)-3-methylphenyl) methanesulfonamide;

9)N-(3-(3-(6-bromo-7-(((S)-1-(ethylsulfonyl) pyrrolidine-3-yl)amino)-3H-imidazo[4,5-b]pyridine-2-yl)-2,5-dimethyl-1H-pyrrol-1-yl)-2-methylphenyl) methanesulfonamide;

10) (S)-6-bromo-2-(2,5-dimethyl-1-(4-(morpholinosulfonyl)phenyl)-1H-pyrrol-3-yl)-N-(1-(ethylsulfonyl) pyrrolidine-3-yl)-3H-imidazo[4,5-b]pyridine-7-amine;

11) (S)-6-bromo-2-(2,5-dimethyl-1-(3-(morpholinosulfonyl)phenyl)-1H-pyrrol-3-yl)-N-(1-(ethylsulfonyl) pyrrolidine-3-yl)-3H-imidazo[4,5-b]pyridine-7-amine;

12) (S)—N-(3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)phenyl) methanesulfonamide;

13) (S)-6-bromo-2-(1-(2,6-dichlorophenyl)-2,5-dimethyl-1H-pyrrol-3-yl)-N-(1-(ethylsulfonyl) pyrrolidine-3-yl)-3H-imidazo[4,5-b]pyridine-7-amine;

14) 6-bromo-2-(1-(2,5-dichlorophenyl)-2,5-dimethyl-1H-pyrrol-3-yl)-N—((S)-1-(ethylsulfonyl) pyrrolidine-3-yl)-3H-imidazo[4,5-b]pyridine-7-amine;

15) (S)-6-bromo-2-(1-(3,4-dichlorophenyl)-2,5-dimethyl-1H-pyrrol-3-yl)-N-(1-(ethylsulfonyl) pyrrolidine-3-yl)-3H-imidazo[4,5-b]pyridine-7-amine;

16) 6-bromo-2-(1-(2-chlorophenyl)-2,5-dimethyl-1H-pyrrol-3-yl)-N—((S)-1-(ethylsulfonyl) pyrrolidine-3-yl)-3H-imidazo[4,5-b]pyridine-7-amine;

17)$_3$-(3-(6-bromo-7-(((S)-1-(ethylsulfonyl) pyrrolidine-3-yl)amino)-3H-imidazo[4,5-b]pyridine-2-yl)-2,5-dimethyl-1H-pyrrol-1-yl)-4-chlorobenzenesulfonamide;

18) (S)-3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)-N-methylbenzenesulfonamide;

19) (S)-3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)-N-ethylbenzenesulfonamide;

20) (S)-3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)benzamide;

21) (S)-6-bromo-N-(1-(ethylsulfonyl) pyrrolidine-3-yl)-2-(1-(3-(2-methoxyethoxy)phenyl)-2,5-dimethyl-1H-pyrrol-3-yl)-1H-imidazo[4,5-b]pyridine-7-amine;

22) (S)-6-bromo-N-(1-(ethylsulfonyl) pyrrolidine-3-yl)-2-(1-(4-(2-methoxyethoxy)phenyl)-2,5-dimethyl-1H-pyrrol-3-yl)-1H-imidazo[4,5-b]pyridine-7-amine;

23) (S)-3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)benzenesulfonamide;

24) (S)-4-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)benzenesulfonamide;

25) (S)-6-bromo-2-(2,5-dimethyl-1-phenyl-1H-pyrrol-3-yl)-N-(1-(ethylsulfonyl) pyrrolidine-3-yl)-3H-imidazo [4,5-b]pyridine-7-amine;

26)$_3$-((6-bromo-2-(1-(2,6-dichlorophenyl)-2,5-dimethyl-1H-pyrrol-3-yl)-3H-imidazo[4,5-b]pyridine-7-yl) amino)benzenesulfonamide;

27)$_3$-((6-bromo-2-(2,5-dimethyl-1-(4-(morpholine-4-carbonyl)phenyl)-1H-pyrrol-3-yl)-3H-imidazo[4,5-b] pyridine-7-yl)amino)benzenesulfonamide;

28)$_3$-((6-bromo-2-(2,5-dimethyl-1-(3-(morpholine-4-carbonyl)phenyl)-1H-pyrrol-3-yl)-3H-imidazo[4,5-b] pyridine-7-yl)amino)benzenesulfonamide;

29)$_3$-((6-bromo-2-(2,5-dimethyl-1-(4-(morpholinosulfonyl)phenyl)-1H-pyrrol-3-yl)-3H-imidazo[4,5-b]pyridine-7-yl)amino)benzenesulfonamide;

30)$_3$-((6-bromo-2-(2,5-dimethyl-1-(3-(morpholinosulfonyl)phenyl)-1H-pyrrol-3-yl)-3H-imidazo[4,5-b]pyridine-7-yl)amino)benzenesulfonamide;

31)$_3$-((6-bromo-2-(1-(2-chlorophenyl)-2,5-dimethyl-1H-pyrrol-3-yl)-3H-imidazo[4,5-b]pyridine-7-yl)amino) benzenesulfonamide;

32)$_3$-((6-bromo-2-(2,5-dimethyl-1-(2-methyl-4-(methylsulfonamido)phenyl)-1H-pyrrol-3-yl)-3H-imidazo[4,5-b]pyridine-7-yl)amino)benzenesulfonamide;

33)$_3$-((6-bromo-2-(2,5-dimethyl-1-(2-methyl-5-(methylsulfonamido)phenyl)-1H-pyrrol-3-yl)-3H-imidazo[4,5-b]pyridine-7-yl)amino)benzenesulfonamide;

34)$_3$-((6-bromo-2-(2,5-dimethyl-1-(2-methyl-3-(methylsulfonamido)phenyl)-1H-pyrrol-3-yl)-3H-imidazo[4,5-b]pyridine-7-yl)amino)benzenesulfonamide;

35)$_3$-((6-bromo-2-(1-(2,5-dichlorophenyl)-2,5-dimethyl-1H-pyrrol-3-yl)-3H-imidazo[4,5-b]pyridine-7-yl) amino)benzenesulfonamide;

36)$_3$-(3-(6-bromo-7-((3-sulfamoylphenyl)amino)-3H-imidazo[4,5-b]pyridine-2-yl)-2,5-dimethyl-1H-pyrrole-1-yl)-4-chlorobenzenesulfonamide;

37)$_3$-((6-bromo-2-(2,5-dimethyl-1-(3-morpholinophenyl)-1H-pyrrol-3-yl)-3H-imidazo[4,5-b]pyridine-7-yl) amino)benzenesulfonamide;

38)$_3$-((6-bromo-2-(2,5-dimethyl-1-(3-(2-morpholinoethoxy)phenyl)-1H-pyrrol-3-yl)-1H-imidazo[4,5-b]pyridine-7-yl)amino)benzenesulfonamide;

39)$_3$-((6-bromo-2-(2,5-dimethyl-1-(4-(2-morpholinoethoxy)phenyl)-1H-pyrrol-3-yl)-1H-imidazo[4,5-b]pyridine-7-yl)amino)benzenesulfonamide;

40)$_3$-((6-bromo-2-(2,5-dimethyl-1-(4-morpholinophenyl)-1H-pyrrol-3-yl)-3H-imidazo[4,5-b]pyridine-7-yl) amino)benzenesulfonamide;

41)$_3$-((2-(1-(benzo[d][1,3]dioxole-5-yl)-2,5-dimethyl-1H-pyrrol-3-yl)-6-bromo-3H-imidazo[4,5-b]pyridine-7-yl)amino)benzenesulfonamide;

42)$_3$-((6-bromo-2-(1-(3-(2-methoxyethoxy)phenyl)-2,5-dimethyl-1H-pyrrol-3-yl)-1H-imidazo[4,5-b]pyridine-7-yl)amino)benzenesulfonamide;

43)$_3$-((6-bromo-2-(2,5-dimethyl-1-phenyl-1H-pyrrol-3-yl)-1H-imidazo[4,5-b]pyridine-7-yl)amino)benzenesulfonamide;

44)$_3$-(3-(7-(benzo[d][1,3]dioxole-5-yl-amino)-6-bromo-3H-imidazo[4,5-b]pyridine-2-yl)-2,5-dimethyl-1H-pyrrol-1-yl)benzenesulfonamide;

45)$_2$-(1-(benzo[d][1,3]dioxole-5-yl)-2,5-dimethyl-1H-pyrrol-3-yl)-6-bromo-N-(4-(2-methoxyethoxy)phenyl)-3H-imidazo[4,5-b]pyridine-7-amine;

46)$_3$-(3-(6-bromo-7-((4-(2-methoxyethoxy)phenyl) amino)-3H-imidazo[4,5-b]pyridine-2-yl)-2,5-dimethyl-1H-pyrrol-1-yl)benzenesulfonamide;

47)$_3$-((6-bromo-2-(2,5-dimethyl-1-(pyridine-3-yl)-1H-pyrrol-3-yl)-1H-imidazo[4,5-b]pyridine-7-yl)amino) benzenesulfonamide;

48)$_3$-((6-bromo-2-(2,5-dimethyl-1-(pyridine-4-ylmethyl)-1H-pyrrol-3-yl)-1H-imidazo[4,5-b]pyridine-7-yl)amino)benzenesulfonamide;

49) (S)-2-(1-(benzo[d][1,3]dioxole-5-yl)-2,5-dimethyl-1H-pyrrol-3-yl)-6-bromo-N-(1-(ethylsulfonyl) pyrrolidine-3-yl)-3H-imidazo[4,5-b]pyridine-7-amine;

50)N-(3-(3-(7-(((S)-1-(ethylsulfonyl) pyrrolidine-3-yl) amino)-3H-imidazo[4,5-b]pyridine-2-yl)-2,5-dimethyl-1H-pyrrol-1-yl)-4-methylphenyl) methanesulfonamide;

51)N-(3-(3-(6-chloro-7-(((S)-1-(ethylsulfonyl) pyrrolidine-3-yl)amino)-3H-imidazo[4,5-b]pyridine-2-yl)-2,5-dimethyl-1H-pyrrol-1-yl)-4-methylphenyl) methanesulfonamide;

52) (S)-6-chloro-2-(2,5-dimethyl-1-(4-(2-morpholinoethoxy)phenyl)-1H-pyrrol-3-yl)-N-(1-(ethylsulfonyl) pyrrolidine-3-yl)-1H-imidazo[4,5-b]pyridine-7-amine;

53) (S)-2-(2,5-dimethyl-1-(4-(2-morpholinoethoxy)phenyl)-1H-pyrrol-3-yl)-N-(1-(ethylsulfonyl) pyrrolidine-3-yl)-1H-imidazo[4,5-b]pyridine-7-amine;

54) (S)-(3-(3-(6-chloro-7-((1-(ethylsulfonyl) pyrrolidine-3-yl)amino)-1H-imidazo[4,5-b]pyridine-2-yl)-2,5-dimethyl-1H-pyrrol-1-yl)phenyl) (morpholino) methanone;

55) (S)-(3-(3-(7-((1-(ethylsulfonyl) pyrrolidine-3-yl) amino)-3H-imidazo[4,5-b]pyridine-2-yl)-2,5-dimethyl-1H-pyrrol-1-yl)phenyl) (morpholino) methanone;

56) (S)-3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)-N-(2-(diethylamino)ethyl)benzamide;

57) (S)-4-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)-N-(2-(diethylamino)ethyl)benzamide;

58) (S)-3-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)benzoic acid;

59) (S)-4-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)benzoic acid;

60) (S)-3-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)-N-((dimethylamino)methyl) benzamide;

61) (S)-3-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)-N-(2-(dimethylamino)ethyl)-N-methylbenzamide;

62) (S)-4-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)-N-(2-(dimethylamino)ethyl) benzamide;

63) (S)-4-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)-N-(2-(dimethylamino)ethyl)-N-methylbenzamide;

64) (S)—N-(3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)phenyl)-2-(dimethylamino) acetamide;

65) (S)—N-(3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)phenyl)-2-(4-methylpiperazine-1-yl) acetamide;

66) (S)—N-(3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)phenyl)-2-morpholinoacetamide;

67) (S)-(4-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)phenyl) (4-methylpiperazine-1-yl) methanone;

68) (S)-(3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)phenyl) (4-methylpiperazine-1-yl) methanone;

69) (S)-3-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)-N-(2-morpholinoethyl)benzamide;

70) (S)-4-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)-N-(2-morpholinoethyl)benzamide;

71) (S)-3-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)-N-(2-(4-methylpiperazine-1-yl)ethyl)benzamide;

72) (S)-4-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)-N-(2-(4-methylpiperazine-1-yl)ethyl)benzamide;

73)N-(4-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-3-methylphenyl)-2-(dimethylamino) acetamide;

74)N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-4-methylphenyl)-2-(dimethylamino) acetamide;

75)N-(4-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-3-methylphenyl)-2-(4-methylpiperazine-1-yl) acetamide;

76)N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-4-methylphenyl)-2-(4-methylpiperazine-1-yl) acetamide;

77)N-(4-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-3-methylphenyl)-2-morpholinoacetamide;

78)N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-4-methylphenyl)-2-morpholinoacetamide;

79)N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-2-methylphenyl)-3-(dimethylamino) propanamide;

80)N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-4-methylphenyl)-3-(dimethylamino) propanamide;

81) (3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-2-methylphenyl) (4-methylpiperazine-1-yl) methanone;

82)$_3$-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-N-(2-(dimethylamino)ethyl)-2-methylbenzamide;

83) (3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-2-methylphenyl) (morpholino) methanone;

84)N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-2-methylphenyl)-2-(dimethylamino) acetamide;

85)N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-2-methylphenyl)-2-morpholinoacetamide;

86)N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-2-methylphenyl)-3-(dimethylamino) propanamide;

87)N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-2-methylphenyl)-2-(4-methylpiperazine-1-yl) acetamide;

88)N-(3-(3-(6-bromo-7-((3-sulfamoylphenyl)amino)-1H-imidazo[4,5-b]pyridine-2-yl)-2,5-dimethyl-1H-pyrrol-1-yl)-4-methylphenyl)-2-morpholinoacetamide;

89)N-(3-(3-(6-bromo-7-((3-sulfamoylphenyl)amino)-1H-imidazo[4,5-b]pyridine-2-yl)-2,5-dimethyl-1H-pyrrol-1-yl)-4-methylphenyl)-2-(4-methylpiperazine-1-yl) acetamide;

90)N-(3-(3-(6-bromo-7-((3-sulfamoylphenyl)amino)-1H-imidazo[4,5-b]pyridine-2-yl)-2,5-dimethyl-1H-pyrrol-1-yl)-4-methylphenyl)-2-(dimethylamino) acetamide;

91) (3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-4-methylphenyl) (morpholino) methanone;

92) (3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-4-methylphenyl) (4-methylpiperazine-1-yl) methanone;

93)$_3$-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-N-(2-(dimethylamino)ethyl)-4-methylbenzamide;

94) 3-((6-bromo-2-(2,5-dimethyl-1-(2-methyl-5-(morpholine-4-carbonyl)phenyl)-1H-pyrrol-3-yl)-1H-imidazo[4,5-b]pyridine-7-yl)amino)benzenesulfonamide;

95) 3-((6-bromo-2-(2,5-dimethyl-1-(2-methyl-5-(4-methylpiperazine-1-carbonyl)phenyl)-1H-pyrrol-3-yl)-1H-imidazo[4,5-b]pyridine-7-yl)amino)benzenesulfonamide;

96) 3-(3-(6-bromo-7-((3-sulfamoylphenyl)amino)-1H-imidazo[4,5-b]pyridine-2-yl)-2,5-dimethyl-1H-pyrrol-1-yl)-N-(2-(dimethylamino)ethyl)-4-methylbenzamide;

97) (4-(3-(6-bromo-7-(((S)-1-(ethylsulfonyl) pyrrolidine-3-yl)amino)-3H-imidazo[4,5-b]pyridine-2-yl)-2,5-dimethyl-1H-pyrrol-1-yl)-3-methylphenyl) (4-methylpiperazine-1-yl) methanone;

98) (4-(3-(6-bromo-7-(((S)-1-(ethylsulfonyl) pyrrolidine-3-yl)amino)-3H-imidazo[4,5-b]pyridine-2-yl)-2,5-dimethyl-1H-pyrrol-1-yl)-3-methylphenyl) (morpholino) methanone.

The compound represented by Formula 1 of the present disclosure may be used as a form of a pharmaceutically acceptable salt, in which the salt is preferably acid addition salt formed by pharmaceutically acceptable free acids. The acid addition salt herein may be obtained from inorganic acids such as hydrochloric acid, nitric acid, phosphoric acid, sulfuric acid, hydrobromic acid, hydriodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid in which at least one halogen selected from the group consisting of F, Cl, Br and I is substituted or unsubstituted. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate and mandelate.

The acid addition salt in the present disclosure may be prepared by the conventional method known to those in the art. For example, the compound represented by Formula 1 is dissolved in an organic solvent such as methanol, ethanol, acetone, methylenechloride, or acetonitrile, to which organic acid or inorganic acid is added to induce precipitation. Then, the precipitate is filtered and dried to give the salt. Alternatively, the solvent and the excessive acid are distillated under reduced pressure, and dried to give the salt. Alternatively, the precipitate is crystallized in an organic solvent to give the same.

A pharmaceutically acceptable metal salt may be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. In this connection, the metal salt is preferably prepared in the pharmaceutically suitable form of sodium, potassium, or calcium salt. And the corresponding silver salt is prepared by the reaction of alkali metal or alkali earth metal salt with proper silver salt (for example, silver nitrate).

Moreover, the present disclosure includes not only the compound represented by Formula 1 but also a pharmaceutically acceptable salt thereof, and a solvate, a stereoisomer, or a hydrate possibly produced therefrom.

The term "solvate" may include a molecular complex including the compound of the present disclosure and at least one pharmaceutically acceptable solvent molecule, e.g., ethanol or water. A complex, in which the solvent molecule is water, is also referred to as "hydrate."

Compounds of the present disclosure may exist as stereoisomers, such as racemates, enantiomers, or diastereomers.

Stereoisomers of the compounds of the formulae herein can include cis and trans isomers, optical isomers such as (R) and(S) enantiomers, diastereomers, geometric isomers, rotational isomers, atropisomers, conformational isomers, and tautomers of the compounds of the present disclosure, including compounds exhibiting more than one type of isomerism, and mixtures thereof (such as racemates and diastereomeric pairs).

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the present disclosure may exhibit the phenomena of tautomerism and structural isomerism. For example, the compounds may exist in several tautomeric forms, including the enol and imine form, and the keto and enamine form and geometric isomers and mixtures thereof. All such tautomeric forms are included within the scope of compounds of the present disclosure. Tautomers exist as mixtures of a tautomeric set in solution. In solid form, usually one tautomer predominates. Even though one tautomer may be described, the present disclosure includes all tautomers of the compounds of the formulae provided.

In addition, some of the compounds of the present disclosure may form atropisomers (e.g., substituted biaryls). Atropisomers are conformational stereoisomers which occur when rotation about a single bond in the molecule is prevented, or greatly slowed, as a result of steric interactions with other parts of the molecule and the substituents at both ends of the single bond are unsymmetrical. The interconversion of atropisomers is slow enough to allow separation and isolation under predetermined conditions. The energy barrier to thermal racemization may be determined by the steric hindrance to free rotation of one or more bonds forming a chiral axis.

Where a compound of the present disclosure contains an alkenyl or alkenylene group, geometric cis/trans (or Z/E) isomers are possible. Cis/trans isomers may be separated by conventional techniques well known to those skilled in the art, for example, chromatography and fractional crystallization.

Conventional methods for the preparation/isolation of individual enantiomers include chiral synthesis from a suitable optically pure precursor or resolution of the racemate (or the racemate of a salt or derivative) using, for example, chiral high pressure liquid chromatography (HPLC) or superfluid critical chromatography (SFC).

Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art.

The present disclosure also includes isotopically-labeled compounds, which are identical to those recited in one of the formulae provided, but for the fact that one or more atoms are replaced by an atom having an atomic mass or mass number different from the atomic mass or mass number usually found in nature.

Isotopically-labeled compounds of the present disclosure can generally be prepared by conventional techniques known to those skilled in the art or by processes analogous to those described herein, using an appropriate isotopically-labeled reagent in place of the non-labeled reagent otherwise employed.

Furthermore, the present disclosure provides a pharmaceutical composition containing the compound represented by Formula 1 or a pharmaceutically acceptable salt thereof as an active ingredient.

The pharmaceutical composition may be used for preventing and treating diseases selected from the group consisting of cancer, degenerative brain disease, non-alcoholic fatty liver disease, and influenza.

The compound represented by Formula 1 may inhibit protein kinase activity.

For example, in terms of protein kinase activity, the MAPK pathway includes ERK1/2 module, JNK/p38 module, ERK5 module, and the like.

In the ERK1/2 module, the MAPK1/2 signaling cascade is activated by ligand binding to receptor tyrosine kinase (RTK), the activated receptor recruits and phosphorylates the adapter proteins Grb2 and SOS, which in turn, interacts with the membrane-bound GTPase Ras and causes its activation. In its activated GTP-binding form, Ras recruits and activates Raf kinases (A-Rf, B-Raf, and C-Raf/Raf-1). Activated Raf kinase activates MAPK 1/2 (MKK1/2), which in turn, catalyzes the phosphorylation of threonine and tyrosine residues in the activation sequence Thr-Glu-Tyr of ERK1/2.

In the JNK/p38 module, the upstream kinases, MAP3Ks, such as MEKK1/4, ASK1/2, and MLK1/2/3, activate MAP2K3/6 (MKK3/6), MAP2K4 (MKK4), and MAP2K7 (MKK7). These MAP2Ks in turn activate JNK protein kinases, including JNK1, JNK2, and JNK3, as well as p38 $\alpha/\beta/\gamma/\delta$. To fulfill their function, JNKs activate several transcription factors including c-Jun, ATF-2, NF-ATc1, HSF-1 and STAT1.

For the ERK5 module, the kinases upstream of MAP2K5 (MKK5) are MEKK2 and MEKK3.

Accordingly, it is possible to prevent or treat related diseases by inhibiting the activity of protein kinases belonging to MAP3K in the MAPK pathway and blocking the upstream.

On the other hand, LRRK2 or LRRK2 mutations have been found in the majority of patients with degenerative brain disease. Mutations present in the LRRK2 kinase domain result in enhancement of LRRK2 kinase activity. In the human brain, LRRK2 expression is highest in the same region of the brain affected by Parkinson's disease, and LRRK2 is found in Lewy bodies, a hallmark of Parkinson's disease. In addition, LRRK2 mutations have been implicated in Alzheimer's disease-like pathology, which may partially overlap between neurodegenerative pathways in both Alzheimer's and Parkinson's disease.

Accordingly, it is possible to prevent or treat degenerative brain diseases such as Parkinson's disease and Alzheimer's disease by using a strong selective brain penetration protein kinase inhibitor for LRRK2.

In the present disclosure, the protein kinase may be MLK family (Mixed lineage kinase family) or LRRK2, and the MLK family may consist of MLK1, MLK2, MLK3, MLK4, DLK, LZK or ZAK.

The cancer may be at least one selected from the group consisting of pseudomyxoma, intrahepatic cholangiocarcinoma, hepatoblastoma, liver cancer, thyroid cancer, colon cancer, testicular cancer, myelodysplastic syndrome, glioblastoma, oral cancer, lip cancer, mycosis fungoides, acute myelogenous leukemia, acute lymphocytic leukemia, basal cell carcinoma, ovarian epithelial cancer, ovarian germ cell carcinoma, male breast cancer, brain cancer, pituitary adenoma, multiple myeloma, gallbladder cancer, biliary cancer, colon cancer, chronic myelogenous leukemia, chronic lymphocytic leukemia, retinoblastoma, choroidal melanoma, diffuse large B cell lymphoma, ampulla of Vater cancer, bladder cancer, peritoneal cancer, parathyroid cancer, adrenal gland cancer, sinunasal cancer, non-small cell lung cancer, non-Hodgkin's lymphoma, tongue cancer, astrocytoma, small cell lung cancer, pediatric brain cancer, pediatric lymphoma, childhood leukemia, small bowel cancer, meningioma, esophagus cancer, glioma, neuroblastoma, renal cancer, kidney cancer, heart cancer, duodenal cancer, malignant soft tissue tumor, malignant bone cancer, malignant lymphoma, malignant mesothelioma, malignant melanoma, eye cancer, vulvar cancer, ureteral cancer, urethral cancer, cancer of unknown primary site, gastric lymphoma, gastric cancer, gastric carcinoid, gastrointestinal stromal cancer, Wilms' tumor, breast cancer, sarcoma, penile cancer, pharyngeal cancer, getstational trophoblatic disease, cervical cancer, endometrial cancer, uterine sarcoma, prostate cancer, metastatic bone cancer, metastatic brain cancer, mediastinal cancer, rectal cancer, rectal carcinoid, vaginal cancer, spinal cord cancer, vestibular schwannoma, pancreatic cancer, salivary gland cancer, Kaposi's sarcoma, Paget's disease, tonsil cancer, squamous cell carcinoma, adenocarcinoma of lung, lung cancer, squamous cell carcinoma of lung, skin cancer, anal cancer, rhabdomyosarcoma, laryngeal cancer, pleural cancer, and thymus cancer.

The degenerative brain disease may be at least one selected from the group consisting of Alzheimer's disease, Down syndrome, Parkinson's disease, Lou Gehrig's disease, dementia, Huntington's disease, multiple sclerosis, proximal lateral sclerosis, apoplexy, stroke and mild cognitive impairment.

The non-alcoholic fatty liver disease may be at least one selected from the group consisting of non-alcoholic fatty liver, non-alcoholic steatohepatitis, cirrhosis and liver cancer.

The influenza may be influenza A or influenza B.

The compound represented by Formula 1 according to the present disclosure may be administered in various forms of oral and parenteral administrations at the time of clinical administration. In the case of formulation, it may be prepared using diluents or excipients such as fillers, extenders, binders, wetting agents, disintegrating agents, surfactants and the like which are usually used.

Solid preparation for oral administration include tablets, pills, powders, granules, capsules, troches and the like, and may be prepared by mixing one or more excipients such as starch, calcium carbonate, sucrose or lactose, gelatin, and the like with the compounds of the present disclosure. In addition, in addition to the simple excipients, lubricants such as magnesium stearate, talc, and the like may also be used. Examples of the liquid preparation for oral administration include suspensions, solutions, emulsions and syrups. In addition to water and liquid paraffin, which are commonly used and are simple diluents, various excipients such as wetting agents, sweeteners, air freshener, preservatives and the like may be included.

Formulations for parenteral administration may include sterilized aqueous solutions, non-aqueous solutions, suspensions, emulsions, lyophilized formulations, and suppositories.

Examples of the non-aqueous solvent and suspension solvent include propylene glycol, polyethylene glycol, vegetable oil such as olive oil, and injectable ester such as ethyl oleate. As a suppository base, witepsol, macrogol, tween 61, cacao butter, laurinum, glycerogelatin and the like may be used.

Furthermore, the present disclosure provides a method for treating cancer, wherein the method includes administering to a subject a therapeutically effective amount of the compound, a stereoisomer thereof, or a pharmaceutically acceptable salt thereof.

The therapeutically effective amount refers to an amount sufficient to alleviate symptoms or improve conditions of a subject when administered into the body, depending on the administration method. In addition, the amount may vary depending on the weight, age, gender, condition, and family history of the subject to be administered. The treatment method in the present disclosure, therefore, may set different doses according to different conditions depending on the subject.

The “effective amount” refers to an amount that is efficient in treating proliferative, inflammatory, infectious, neurological or cardiovascular disorder or in treating the disease. In another specific embodiment, the “effective amount” of a compound refers to at least the minimum amount capable of inhibiting the proliferation of the disease.

The compound and the composition according to the method of the present disclosure may be administered at an effective dose by a random administration pathway for the treatment of a disease. The exact amount required may vary subject to subject, depending on the species, age, and general condition of a subject, severity of infection, a specific agent and its mode of administration, etc. The compound of the present disclosure may be frequently formulated in a dose unit form for ease of administration and uniformity of dosage. The term “dose unit form” means a physically independent unit of formulation which is appropriate for the treatment of a target subject, as used herein. However, it is understood that the total daily dose of the compound and the composition of the present disclosure may be determined by a doctor within the scope of sound medical judgment. The particular effective dosage level for any particular subject or organism will depend on a variety of factors, including the followings.

The term “subject” herein indicates an animal, for example a mammal, such as a human.

The pharmaceutical composition of the present disclosure may be administered to humans and other animals systemically or locally, orally or parenterally (nasal, transpulmonary, intravenous, rectal, subcutaneous, intramuscular, transdermal, etc.) depending on the severity of the infection to be treated.

In order to obtain a desired therapeutic effect by using the pharmaceutical composition of the present disclosure for actual treatment, the dosage of the compound represented by Formula 1 of the present disclosure as an active ingredient, or a pharmaceutically acceptable salt thereof, is appropriately determined according to the age, gender, body weight, disease, and degree of treatment of a patient. For example, in the case of oral administration, in the range of roughly 0.001 to 3,000 mg/Kg per day for adults (body weight of 60 kg), it may be appropriately administered once for all or in several divided doses, and may be administered orally or parenterally once or multiple times per two days, per week or per month. The dose for a specific subject or a patient should be determined in light of several related factors such as the patient’s body weight, age, gender, health condition, diet, time of administration, method of administration, severity of disease, etc. It is to be understood that the dose may be appropriately adjusted by a practitioner. The dose is not intended to limit the scope of the present disclosure in any aspects.

Liquid formulation for oral administration includes pharmaceutically acceptable emulsions, microemulsions, solutions, suspensions, syrups and elixirs, but not always limited thereto. In addition to the active compound, the liquid formulation may additionally include inert diluents of the following examples commonly used in the art: water or other solvents, solubilizing agents and emulsifying agents such as ethyl alcohol, isopropyl alcohol, ethyl carbonate, ethyl acetate, benzyl alcohol, benzyl benzoate, propylene glycol, 1,3-butylene glycol, dimethyl formamide, oil (for example, cotton seed oil, peanut oil, corn oil, bacteria oil, olive oil, caster oil, and sesame oil), glycerol, tetrahydrofuryl alcohol, polyethylene glycol, fatty acid ester of sorbitan, and mixtures thereof. In addition to the inert diluents, the formulation for oral administration may also include adjuvants such as wetting agents, emulsifying and suspending agents, sweetening agents, flavoring agents, and flavoring agents.

Injectable preparations, for example, sterile injectable aqueous or lipid productive suspensions may be formulated by using proper dispersing or wetting agents and suspending agents according to the well known art. The sterile injectable preparations may also be sterile injectable solutions, suspensions or emulsions in a non-toxic parenterally acceptable diluent or solvent, for example 1,3-butanediol solution. Among usable vehicles and solvents, water, Ringer’s solution, USP and isotonic sodium chloride solution may be selected. A sterilized fixed oil has been used conventionally as a solvent or a dispersion medium. A random blend fixed oil including synthetic mono- or diglyceride may be used for this purpose. In addition, fatty acids such as oleic acid may be used for the preparation of injectable preparations.

The injectable formulations may be sterilized by filtering using a bacteria-fixed filter or incorporating a germicide as a sterilized solid composition form that may be dissolved or dispersed in sterilized water or other sterilized injectable media.

To obtain a continued effect of the compound of the present disclosure, slow absorption of the compound from subcutaneous or intramuscular injection is often desired. This slow absorption may be achieved by using a liquid suspension of crystalline or amorphous material having poor water solubility.

The absorption rate of a compound depends on the dissolution rate affected by the crystal size and the crystal form. Alternatively, delayed absorption of the parenterally administered compound may be achieved by dissolving or suspending the compound in an oil vehicle. The injectable depot formulation may be prepared by forming a microencapsule matrix of the compound in a biodegradable polymer such as polylactide-polyglycolide. According to the ratio of the compound to the polymer and the characteristics of the particular polymer used herein, the discharge rate of the compound may be regulated. Examples of other biodegradable polymers include poly(orthoester) and poly(anhydride). The injectable depot formulation may also be prepared by entrapping the compound in liposome or microemulsion compatible with body tissues.

The composition for rectal or vaginal administration is, for example, a suppository which may be prepared by mixing the compound of the present disclosure with a suitable non-irritating excipient or a carrier such as cocoa butter, polyethylene glycol or suppository wax. This suppository is a solid at a room temperature, but is a liquid at body temperature and therefore melts in the rectum or vagina to release the active compound.

Solid formulations for oral administration include capsules, tablets, pills, powders, and granules. In such solid formulations for oral administration, the active compound is mixed with at least one inert, pharmaceutically acceptable excipient or carrier such as sodium citrate or dicalcium phosphate and/or a) fillers or extenders such as starch, lactose, sucrose, glucose, mannitol and silicic acid, b) binders such as carboxymethylcellulose, alginate, gelatin, polyvinylpyrrolidinone, sucrose and acacia, c) humectant such as glycerol, d) disintegrating agent such as agar, calcium carbonate, potato or tapioca starch, alginic acid, any specific silicate and sodium carbonate, e) solution retarders such as paraffin, f) absorption accelerators such as quaternary ammonium compounds, g) wetting agents such as cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the administration formulations may also contain buffering agents.

Solid compositions of a similar type may also be employed as fillers in soft and hard-filled gelatin capsules using excipients such as lactose or milk sugar as well as high molecular polyethylene glycol. Solid formulations such as tablets, dragees, capsules, tablets, and granules may be prepared by mixing with coating materials and shells such as enteric coating materials and other coating materials well known in the field of pharmaceutical formulation technology. The composition may contain an opacifying agent. The composition of the present disclosure may be a composition that releases only the active ingredient(s), for example, in a particular part of the intestinal tract in a delayed manner. A usable embedding composition is exemplified by a polymeric substance and wax. Solid compositions of a similar type may also be employed as fillers in soft and hard-filled gelatin capsules using excipients such as lactose or milk sugar as well as high molecular polyethylene glycol.

The active compound may also be in a microencapsulated form with one or more excipients as described above. Solid formulations such as tablets, dragees, capsules, tablets, and granules may be prepared by mixing with coating materials and shells such as enteric coating materials and other coating materials well known in the field of pharmaceutical formulation technology. In such solid formulations, the active compound may be mixed with one or more inert diluents such as sucrose, lactose and starch. Such administration formulations may also contain additional substances other than inert diluents, such as tableting lubricants and other tableting aids such as magnesium stearate and microcrystalline cellulose. In the case of capsules, tablets and pills, the administration formulations may also contain buffering agents. The composition may contain an opacifying agent. The composition of the present disclosure may be a composition that releases only the active ingredient(s), for example, in a particular part of the intestinal tract in a delayed manner. A usable embedding composition is exemplified by a polymeric substance and wax.

The formulations for topical or transdermal administration of the present disclosure include ointments, pastes, creams, lotions, gels, powders, solutions, sprays, inhalants or patches. The active ingredient is mixed with a pharmaceutically acceptable carrier and any necessary preservative or buffer under the sterile condition. Ophthalmic formulations, ear drops, and eye drops are also contemplated as being within the scope of the present disclosure. The present disclosure additionally includes transdermal patches which had advantage of providing controlled cleavage of the compound to the body. Such administration formulations may be prepared by dissolving or dispersing the compound in a proper medium. An absorption enhancer may also be used to increase the flow of the compound across the skin. The absorption rate may be controlled by providing a rate controlling membrane or by dispersing the compound in a polymer matrix or gel.

In a preferred embodiment of the present disclosure, the compound of the present disclosure or the pharmaceutical composition comprising the same may be administered with an anticancer agent. In the present disclosure, the term "anticancer agent" refers to any agent that is administered to a subject with cancer for the purpose of cancer treatment.

Combination therapy includes administration of the therapeutic agents concurrently or sequentially. Alternatively, the therapeutic agent may be combined into one composition to be administered to a subject.

In a preferred embodiment of the present disclosure, the compound of the present disclosure is co-treated with other therapeutic agents. The compound of the present disclosure may be administered alone or treated together with cytotoxic drugs, radiation therapy, and immunotherapy.

Additional agents may be administered separately from the combination therapy provided as a part of a multiple dose regimen. Alternatively, the agents may be a part of a single dosage form mixed with the compound of the present disclosure. If administered as a part of a combination therapy, the two therapeutic agents may be administered simultaneously, sequentially, or intermittently. The combination therapy may be used for any of symptoms described herein. In a preferred embodiment of the present disclosure, the combination therapy is performed to treat a proliferative disorder (for example, cancer) of a subject.

In another aspect of the present disclosure, the present disclosure relates to inhibit the aforementioned disease in a biological sample or a subject. The method comprises administering the compound represented by Formula 1 or the composition comprising the said compound, or contacting the biological sample with the said compound. The term "biological sample" herein includes in vivo, in vitro and ex vivo materials, and also includes cell cultures or extracts thereof; biopsied materials obtained from a mammal or extracts thereof; and blood, saliva, urine, feces, semen, tears, or other body fluids or extracts thereof.

The compound or the pharmaceutically acceptable salt thereof according to the present disclosure has been identified through experiments to be efficient in preventing or treating cancer, degenerative brain disease, non-alcoholic fatty liver disease, and influenza.

To evaluate the inhibitory activity of the compound of the present disclosure on enzymes, the experiment was performed as described in Experimental Example 1 or 2 below. As a result, it was identified that the compound of the examples of the present disclosure had inhibitory activity against MLK family, and that the compound demonstrated excellent inhibitory activity at nanomole level. Thus, the compound of the present disclosure may be effectively used for the prevention or treatment of not only the diseases related with the enzymes listed above but also cancers induced therefrom.

In addition, the cancer cell proliferation inhibition activity of the compound of the present disclosure was evaluated with various cancer cell lines as shown in Experimental Examples 3 to 6 below. As a result, the cancer cell proliferation inhibition activity was identified to be surprisingly excellent. Moreover, as shown in Experimental Example 7 below, it was identified that the compound inhibited cancer metastasis and excellently inhibited cancer cell proliferation (cancer cell death). Thus, the compound of the present disclosure was identified to be useful for the prevention or treatment of cancer.

In addition, as a result of evaluating the fibrosis inhibitory activity, which is a symptom of non-alcoholic steatohepatitis, in human liver cancer cell lines as in Experimental Examples 8 and 9 below, the compound according to the present disclosure was identified to have an excellent anti-fibrotic effect, and was identified to improve the evaluation index for non-alcoholic steatohepatitis induced by the MCD diet as in Experimental Example 10 below. Thus, the compound of the present disclosure was identified to be useful for the prevention or treatment of non-alcoholic fatty liver disease.

In addition, the compound according to the present disclosure was identified to have an excellent inhibitory activity on LRRK2 as in Experimental Examples 11 to 13 below. Thus, the compound of the present disclosure was identified to be useful as a drug for preventing or treating degenerative brain disease.

In addition, the compound according to the present disclosure was identified to have an excellent effect on antivirals as in Experimental Examples 14 to 16 below. Thus, the compound of the present disclosure was identified to be useful as a drug for preventing or treating influenza.

Hereinafter, the present disclosure will be described in detail by way of Examples and Experimental Examples. However, the following Examples and Experimental Examples are merely illustrative of the present disclosure, and the content of the present disclosure is not limited thereto.

EXAMPLES

The compounds of the present disclosure may be prepared by the following Synthesis Methods 1 to 3 as examples.

For reference, as in Synthesis Method 1 below, the reaction may proceed after substituting a halogen atom (X) in the pyridine ring in the preparation of Compound B, and after completion of the reaction, the removal of the halogen atom (X) may further proceed, or the halogen atom (X) may not be removed.

In addition, as in the preparation of Compound C of Synthesis Method 2 below, the reaction may proceed without substituting a halogen atom (X) in the pyridine ring.

<Synthesis Method 1>

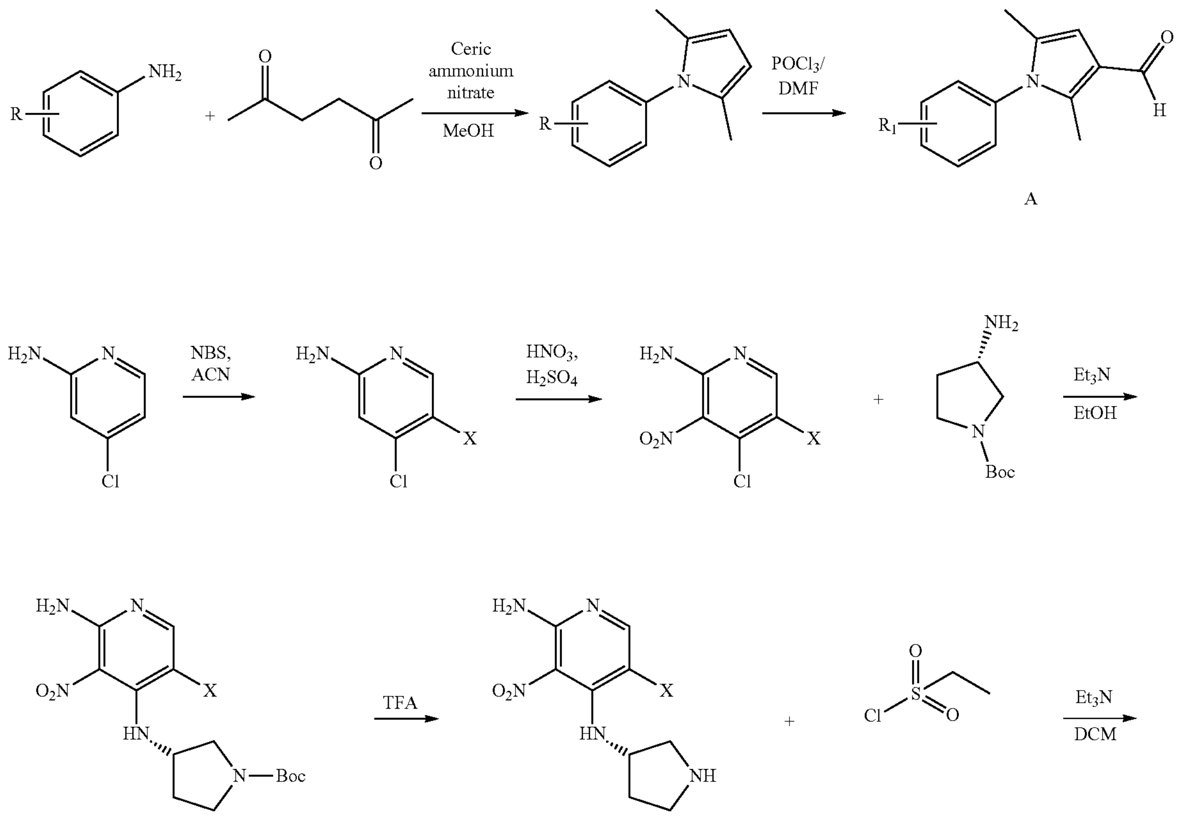

A

-continued
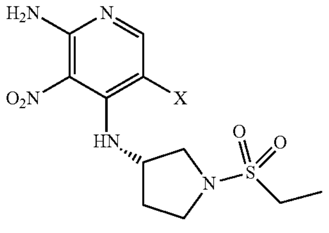
B
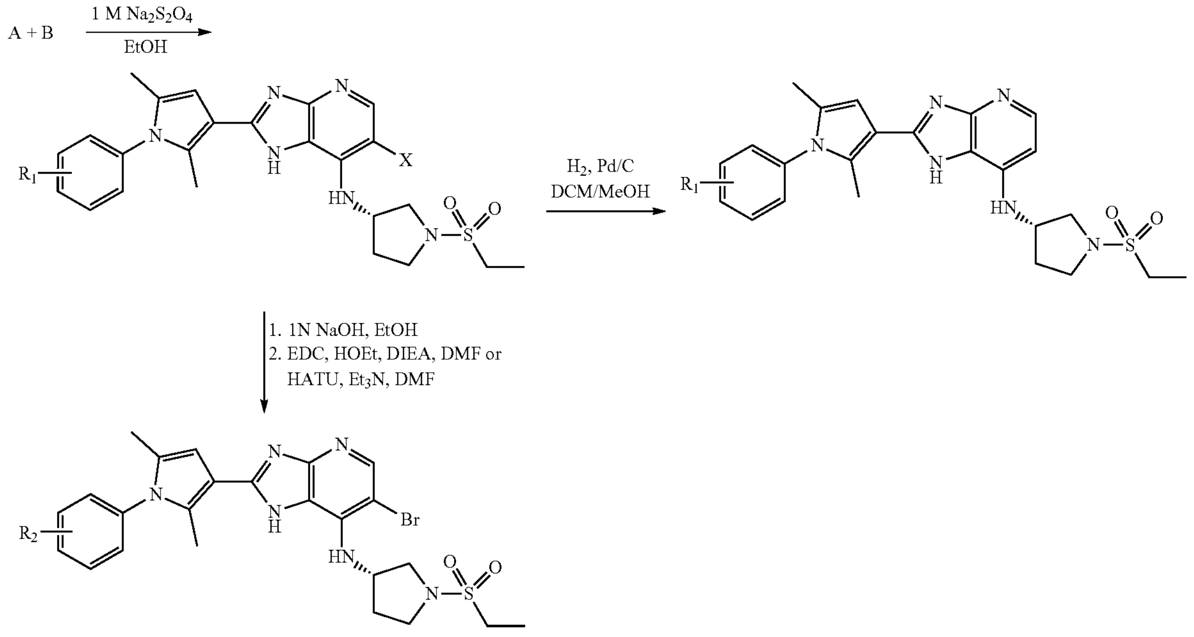
<Synthesis Method 2>
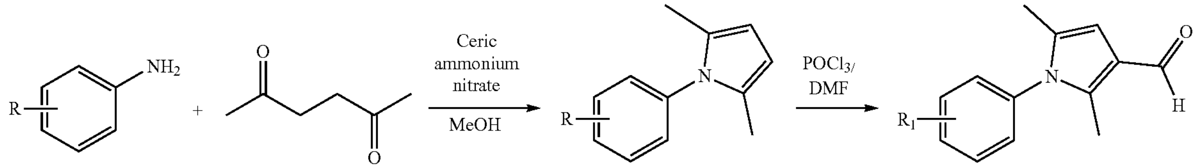
A
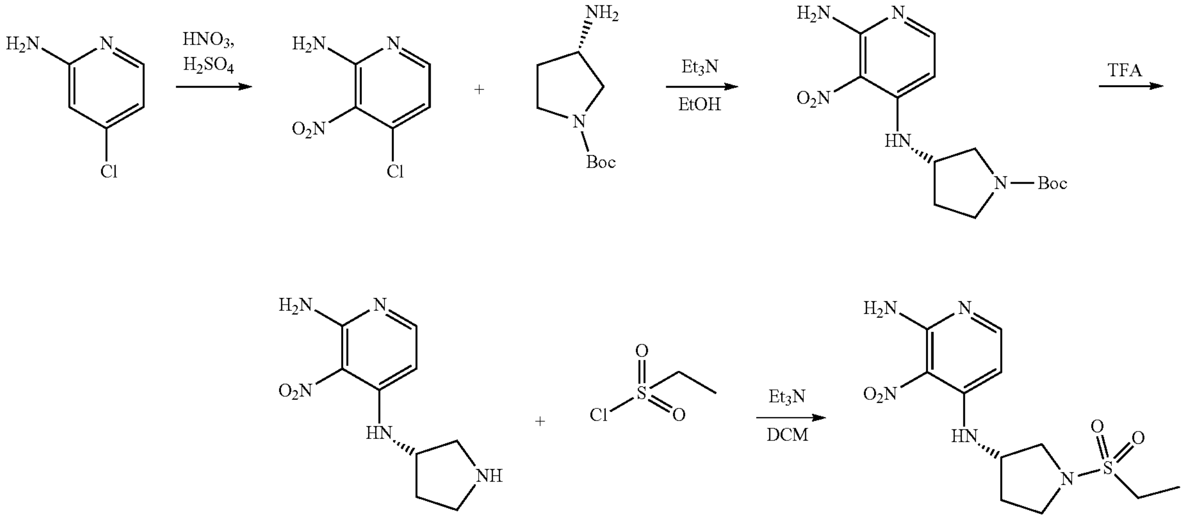
C -continued
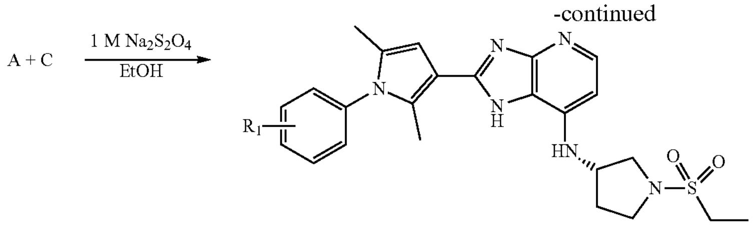
<Synthesis Method 3>
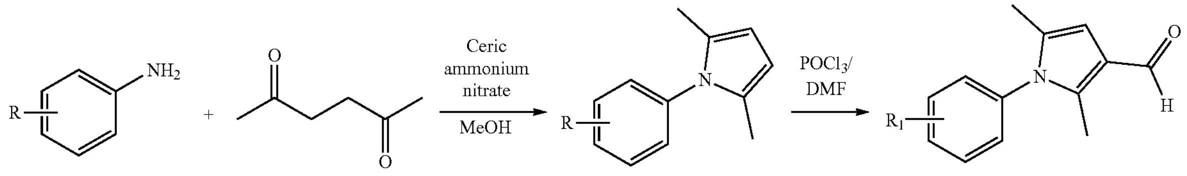
A
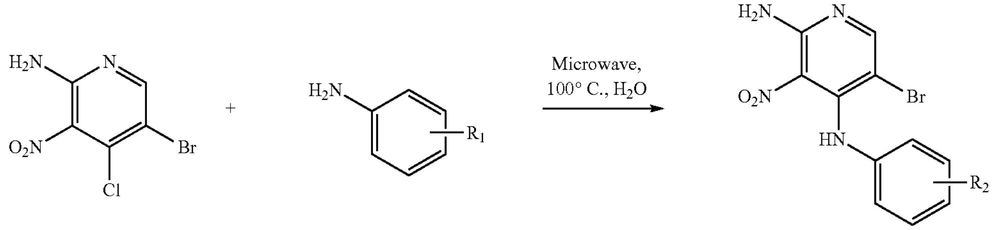
D
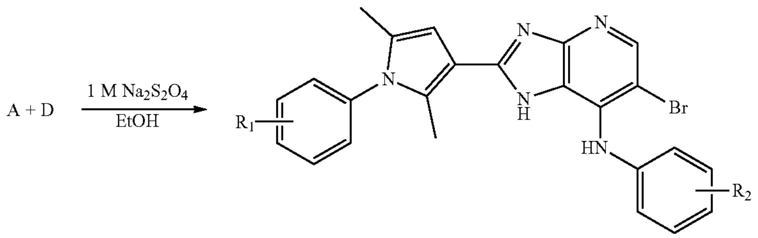
Example 1: (S)-6-bromo-2-(2,5-dimethyl-1-(4-morpholinophenyl)-1H-pyrrol-3-yl)-N-(1-(ethylsulfonyl)pyrrolidine-3-yl)-3H-imidazo[4,5-b]pyridine-7-amine
The compound of Example 1 may be prepared according to Synthesis Method 1, specifically, by a reaction as shown in Scheme 1 below.
[Reaction Formula 1]
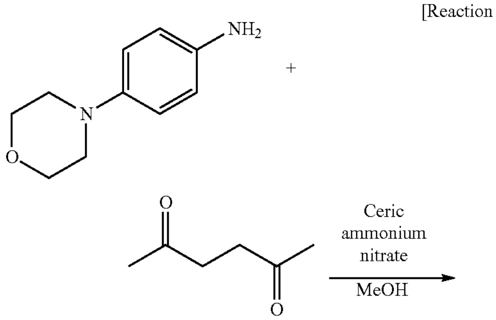
-continued
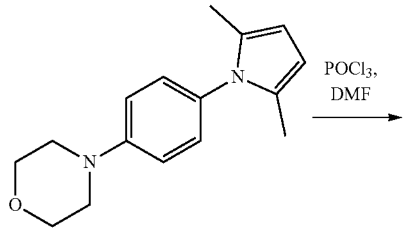
a
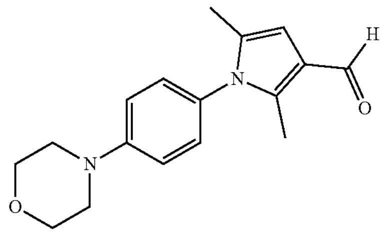
b -continued

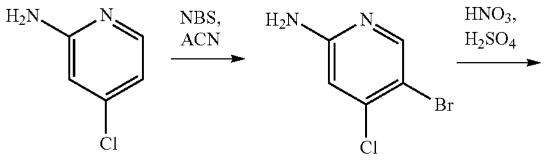

c

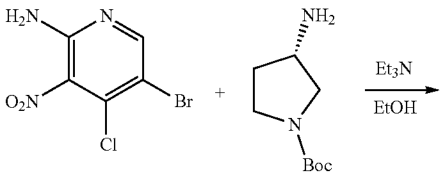

d

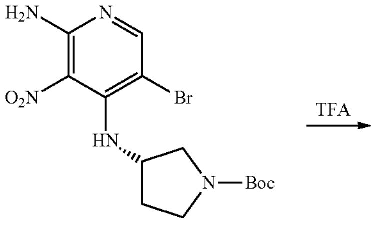

e

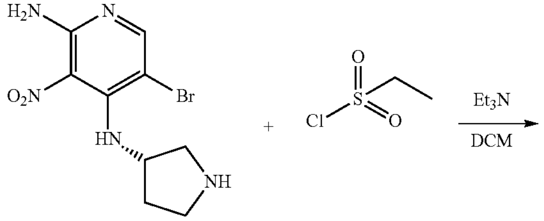

f

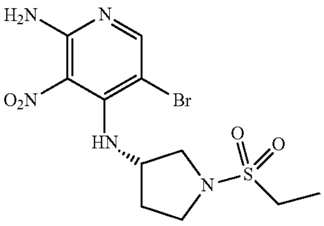

g

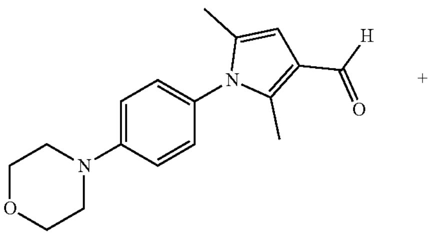

b

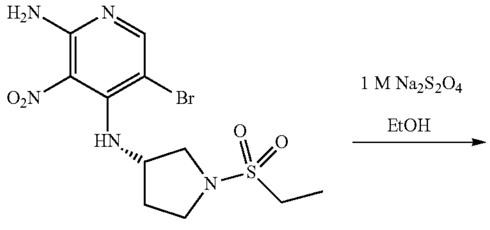

g

-continued

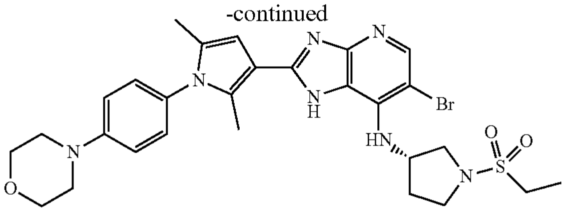

h 1-1. Synthesis of Compound b 4-morpholinoaniline (1 eq), hexane-2,5-dione (1 eq), MeOH, and ceric ammonium nitrate (0.05 eq) were mixed and stirred at room temperature for 3 hours. The reaction mixture was concentrated under reduced pressure. The crude product was purified by column chromatography (silicagel, Hexane/EtOAc) to obtain the target compound a (74%).

Dimethylformamide was put in each of the two containers and the temperature was dropped to 0° C. Compound a (1 eq) and phosphoryl chloride (1.2 eq) were each added and dissolved. Phosphoryl chloride (in DMF) was slowly added to compound a (in DMF) and stirred. After the reaction was completed, the solid obtained after adjusting the pH to 14 using 20% NaOH was filtered, washed with water and dried to obtain the target compound b (86%).

1-2. Synthesis of Compound g 4-chloropyridin-2-amine (1 eq), N-bromosuccinimide (1.05 eq), and acetonitrile were mixed and stirred at room temperature for 12 hours. The reaction mixture was concentrated under reduced pressure, diluted with EtOAc, washed with 1N NaOH, water, and brine, dried over $Na_2SO_4$, and concentrated. The crude product was recrystallized (DCM/Hxane) to obtain the target compound c (70%).

Compound c (1 eq) and $H_2SO_4$ were mixed at 0° C., $HNO_3$ (1.07 eq) was added, and heated to 55° C. and stirred for 1 hour. Ice crush was added to the reaction mixture, and pH was adjusted to 7 using NaOH. The solid was filtered, washed with water and dried to obtain the target compound d (66%).

Compound d (1 eq), (s)-(−)-1-Boc-3-aminopyrrolidine (1.2 eq), trimethylamine (4 eq), and EtOH were mixed, heated to 80° C., and stirred for 2 hours. The temperature of the reaction mixture was dropped to −20° C. The solid was filtered, washed with water and dried to obtain compound e (73%).

Compound e (1 eq), TFA (26.1 eq), and DCM were mixed and stirred at room temperature for 3 hours. After the addition of DCM to the reaction mixture, evaporation was repeated, and then dried to obtain compound f.

Compound f (1 eq), ethanesulfonyl chloride (1.1 eq), trimethylamine (5 eq), and dichloromethane were mixed at −5° C. and stirred for 1 hour. The reaction mixture was concentrated under reduced pressure. The solid was filtered, washed with water and dried to obtain compound g (98%).

1-3. Synthesis of Final Product h

Compound b (1 eq) obtained in the above synthesis example, compound g (1 eq), sodium dithionite (4.09 eq), and EtOH were mixed and stirred for 2 days. The reaction mixture was concentrated under reduced pressure, diluted with EtOAc, washed with water and brine, dried over $Na_2SO_4$, and concentrated. The crude product was purified by column chromatography (silicagel column, Hxane/EtOAc) to obtain a final product h (60%). 1H NMR (300 MHz, DMSO-d6) δ 1.19 (t, J=7.3 Hz, 3H), 1.98 (s, 3H), 2.10 (m, 1H), 2.31 (m, 1H), 2.37 (s, 3H), 3.09 (q, J=7.5 Hz 2H), 3.20 (t, J=4.4 Hz, 4H), 3.30 (m, 1H), 3.35 (m, 1H), 3.50 (m, 1H), 3.68 (m, 1H), 3.75 (d, J=4.4 Hz, 4H), 5.62 (m, 1H), 5.75 (d, J=8.0 Hz, 1H), 6.54 (s, 1H), 7.07 (d, J=9 Hz, 2H), 7.16 (d, J=8.8 Hz, 2H), 7.96 (s, 1H), 12.66 (s, 1H)

Hereinafter, the compounds of Examples 2 to 25 were synthesized according to the representative synthesis method 1.

Example 2: (S)-6-bromo-2-(2,5-dimethyl-1-(3-morpholinophenyl)-1H-pyrrol-3-yl)-N-(1-(ethylsulfonyl) pyrrolidine-3-yl)-3H-imidazo[4,5-b]pyridine-7-amine

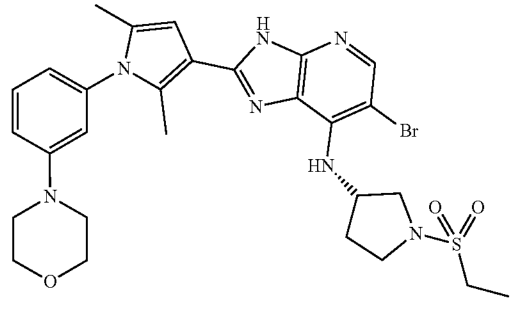

$^1$H NMR (300 MHz, DMSO-$d_6$) δ 1.19 (t, J=7.40 Hz, 3H), 2.02 (m, 3H), 2.12 (m, 1H), 2.31 (m, 1H), 2.41 (s, 3H), 3.09 (q, J=7.11 Hz, 2H), 3.18 (t, J=4.3 Hz, 4H), 3.28 (m, 1H), 3.35 (m, 1H), 3.49 (m, 1H), 3.67 (m, 1H), 3.74 (t, J=4.30 Hz, 4H), 5.63 (m, 1H), 5.76 (d, J=8.0 Hz, 1H), 6.56 (s, 1H), 6.72 (d, J=7.54 Hz, 1H), 6.85 (s, 1H), 7.05 (d, J=8.66 Hz, 1H), 7.39 (t, J=8.01 Hz, 1H), 7.97 (s, 1H), 12.68 (s, 1H).

Example 3: (S)-6-bromo-2-(2,5-dimethyl-1-(3-(2-morpholinoethoxy)phenyl)-1H-pyrrol-3-yl)-N-(1-(ethylsulfonyl) pyrrolidine-3-yl)-1H-imidazo[4,5-b] pyridine-7-amine

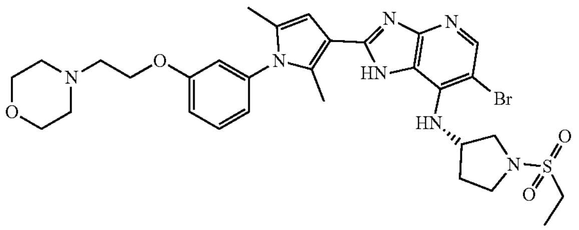

$^1$H NMR (300 MHZ, DMSO-$d_6$) δ 1.19 (t, J=7.5 Hz, 3H), 2.02 (s, 3H), 2.13 (m, 1H), 2.31 (m, 1H), 2.41 (s, 3H), 2.47 (m, 4H), 2.70 (t, J=5.8 Hz, 2H), 3.09 (q, J=7.0 Hz, 2H), 2.28 (m, 1H), 3.36 (m, 1H), 3.5 (m, 1H), 3.57 (t, J=4.7 Hz, 4H), 3.68 (m, 1H), 4.15 (m, 2H), 5.61 (m, 1H), 5.77 (d, J=7.7 Hz, 1H), 6.57 (s, 1H), 6.91 (m, 2H), 7.08 (d, J=7.8, 1H), 7.45 (t, J=8.1, 1H), 7.97 (s, 1H), 12.70 (s, 1H).

Example 4: (S)-6-bromo-2-(2,5-dimethyl-1-(4-(2-morpholinoethoxy)phenyl)-1H-pyrrol-3-yl)-N-(1-(ethylsulfonyl) pyrrolidine-3-yl)-1H-imidazo[4,5-b] pyridine-7-amine

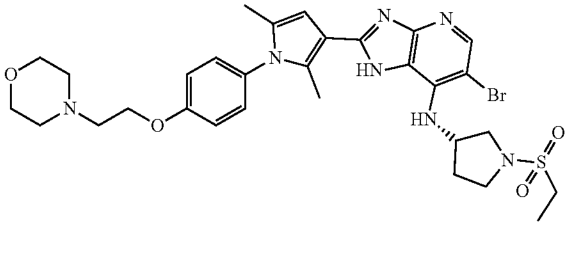

$^1$H NMR (300 MHZ, DMSO-$d_6$) & 1.19 (t, J=7.4 Hz, 3H), 1.98 (s, 3H), 2.11 (m, 1H), 2.32 (m, 4H), 2.48 (m, 4H), 2.72 (t, J=5.5 Hz, 2H), 3.09 (q, J=7.4 Hz, 2H), 3.29 (m, 1H), 3.36 (m, 1H), 3.49 (m, 1H), 3.59 (m, 4H), 3.68 (m, 1H), 4.15 (t, J=5.6 Hz, 2H), 5.63 (m, 1H), 5.76 (m, 1H), 6.56 (s, 1H), 7.09 (d, J=8.9 Hz, 2H), 7.24 (d, J=8.8 Hz, 2H), 7.97 (s, 1H), 12.68 (s, 1H).

Example 5: (S)-(4-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)phenyl) (morpholino) methanone

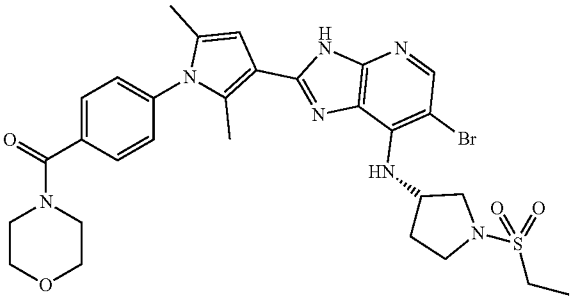

$^1$H NMR (300 MHZ, DMSO-$d_6$) δ 1.19 (t, J=7.3 Hz, 3H), 2.03 (s, 3H), 2.10 (m, 1H), 2.29 (m, 1H), 2.42 (s, 3H), 3.09 (q, J=7.4 Hz, 2H), 3.30 (m, 1H), 3.36 (m, 1H), 3.60 (m, 10H), 5.63 (m, 1H), 5.78 (d, J=7.1 Hz, 1H), 6.60 (s, 1H), 7.44 (d, J=8.5 Hz, 2H), 7.59 (d, J=8.4 Hz, 2H), 7.97 (s, 1H), 12.74 (s, 1H).

Example 6: (S)-(3-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)phenyl) (morpholino) methanone

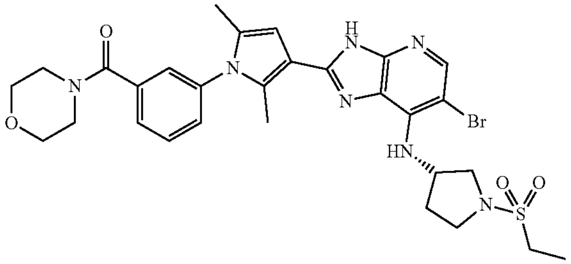

$^1$H NMR (300 MHZ, DMSO-$d_6$) δ 1.19 (t, J=7.3 Hz, 3H), 2.03 (s, 3H), 2.13 (m, 1H), 2.31 (m, 1H), 2.41 (s, 3H), 3.09 (m, 2H), 3.25 (m, 1H), 3.50 (m, 4H), 3.58 (m, 7H), 5.63 (m, 1H), 5.77 (m, 2H), 6.60 (s, 1H), 7.40 (s, 1H), 7.46 (d, J=7.2 Hz, 1H), 7.54 (d, J=8.1, 1H), 7.66 (m, 1H), 7.98 (s, 1H), 12.74 (s, 1H).

Example 7: N-(3-(3-(6-bromo-7-(((S)-1-(ethylsulfonyl) pyrrolidine-3-yl)amino)-3H-imidazo[4,5-b] pyridine-2-yl)-2,5-dimethyl-1H-pyrrol-1-yl)-4-methylphenyl) methanesulfonamide

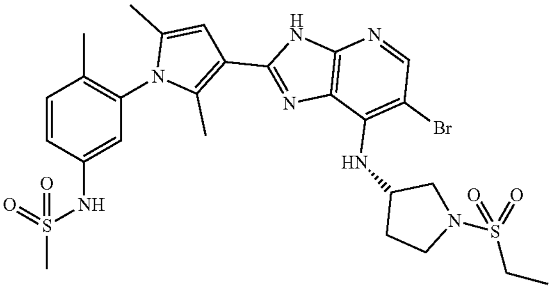

$^1$H NMR (300 MHZ, DMSO-$d_6$) δ 1.19 (t, J=7.3 Hz, 3H), 1.88 (s, 3H), 1.91 (s, 3H), 2.13 (m, 1H), 2.31 (m, 4H), 3.03 (s, 3H), 3.08 (q, J=7.4 Hz, 2H), 3.30 (m, 1H), 3.35 (m, 1H), 3.50 (m, 1H), 3.68 (m, 1H), 5.63 (m, 1H), 5.77 (d, J=7.4 Hz, 1H), 6.62 (s, 1H), 7.03 (d, J=2 Hz, 1H), 7.27 (d, J=8 Hz, 1H), 7.43 (d, J=8.4 Hz, 1H), 7.98 (s, 1H), 9.91 (s, 1H), 12.73 (s, 1H).

Example 8: N-(4-(3-(6-bromo-7-(((S)-1-(ethylsulfonyl) pyrrolidine-3-yl)amino)-3H-imidazo[4,5-b] pyridine-2-yl)-2,5-dimethyl-1H-pyrrol-1-yl)-3-methylphenyl) methanesulfonamide

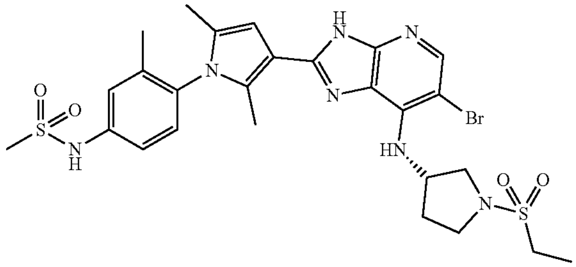

$^1$H NMR (300 MHz, DMSO-$d_6$) δ 1.18 (t, J=7.4 Hz, 3H), 1.89 (s, 6H), 2.11 (m, 1H), 2.28 (m, 4H), 3.08 (m, 5H), 3.29 (m, 1H), 3.35 (m, 1H), 3.50 (m, 1H), 3.68 (m, 1H), 5.63 (m, 1H), 5.76 (d, J=8.1 Hz, 1H), 6.60 (s, 1H), 7.21 (m, 3H), 7.97 (s, 1H), 10.00 (s, 1H), 12.70 (s, 1H).

Example 9: N-(3-(3-(6-bromo-7-(((S)-1-(ethylsulfonyl) pyrrolidine-3-yl)amino)-3H-imidazo[4,5-b] pyridine-2-yl)-2,5-dimethyl-1H-pyrrol-1-yl)-2-methylphenyl) methanesulfonamide

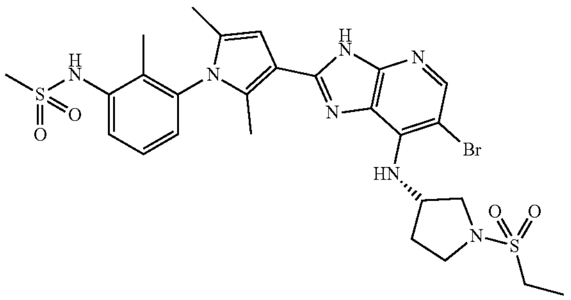

$^1$H NMR (300 MHZ, DMSO-$d_6$) δ 1.18 (t, J=7.3 Hz, 3H), 1.88 (d, J=3.2 Hz, 6H), 2.12 (m, 1H), 2.28 (s, 3H), 2.35 (m, 1H), 3.05 (s, 3H), 3.08 (q, J=7.2 Hz, 2H), 3.27 (m, 1H), 3.44 (m, 1H), 3.51 (m, 1H), 3.68 (m, 1H), 5.65 (m, 1H), 5.76 (d, J=8.0 Hz, 1H), 6.62 (s, 1H), 7.2 (d, J=8.4 Hz, 1H), 7.44 (m, 2H), 7.98 (s, 1H), 9.3 (s, 1H), 12.72 (s, 1H).

Example 10: (S)-6-bromo-2-(2,5-dimethyl-1-(4-(morpholinosulfonyl)phenyl)-1H-pyrrol-3-yl)-N-(1-(ethylsulfonyl) pyrrolidine-3-yl)-3H-imidazo[4,5-b] pyridine-7-amine

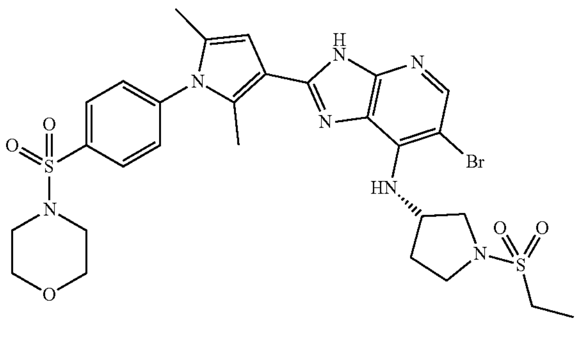

$^1$H NMR (300 MHz, DMSO-$d_6$) δ 1.19 (t, J=7.4 Hz, 3H), 2.05 (s, 3H), 2.12 (m, 1H), 2.32 (m, 1H), 2.44 (s, 3H), 2.95 (t, J=4.2 Hz, 4H), 3.10 (q, J=7.5 Hz, 2H), 3.28 (m, 1H), 3.36 (m, 1H), 3.51 (m, 1H), 3.67 (m, 5H), 5.65 (m, 1H), 5.80 (d, J=7.9 Hz, 1H), 6.64 (s, 1H), 7.69 (d, =8.3 Hz, 2H), 7.91 (d, J=8.3 Hz, 2H), 7.99 (s, 1H), 12.78 (s, 1H).

Example 11: (S)-6-bromo-2-(2,5-dimethyl-1-(3-(morpholinosulfonyl)phenyl)-1H-pyrrol-3-yl)-N-(1-(ethylsulfonyl) pyrrolidine-3-yl)-3H-imidazo[4,5-b] pyridine-7-amine

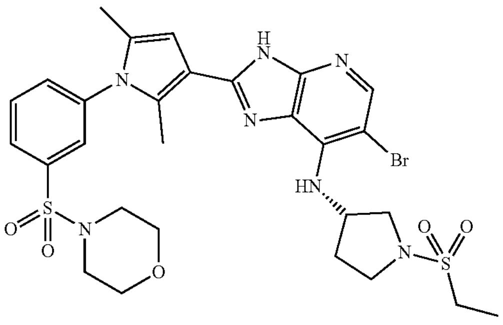

$^1$H NMR (300 MHz, DMSO-$d_6$) δ 1.19 (t, J=7.4 Hz, 3H), 2.04 (s, 3H), 2.14 (m, 1H), 2.32 (m, 1H), 2.43 (s, 3H), 2.95 (m, 4H), 3.09 (q, J=7.2 Hz, 2H), 3.28 (m, 1H), 3.36 (m, 1H), 3.50 (m, 1H), 3.65 (m, 4H), 3.70 (m, 1H), 5.62 (m, 1H), 5.79 (m, 1H), 6.64 (s, 1H), 7.67 (s, 1H), 7.8 (m, 1H), 7.88 (d, J=4.9 Hz, 2H), 7.99 (s, 1H), 12.77 (s, 1H).

Example 12: (S)—N-(3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)phenyl) methanesulfonamide

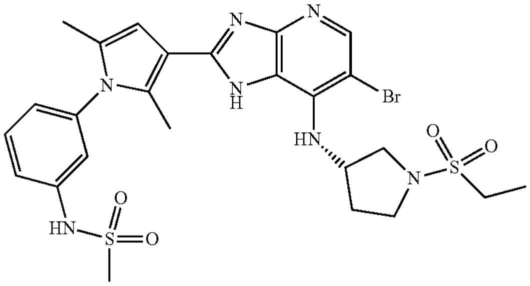

$^1$H NMR (300 MHZ, DMSO-$d_6$) δ 1.19 (t, J=7.3, 3H), 2.02 (s, 3H), 2.12 (m, 1H), 2.32 (m, 1H), 2.41 (s, 3H), 3.09 (m, 5H), 3.28 (m, 1H), 3.34 (m, 1H), 3.48 (m, 1H), 3.68 (m, 1H), 5.63 (m, 1H), 5.77 (d, J=8.4, 1H), 6.59 (s, 1H), 7.08 (m, 2H), 7.31 (d, J=6, 1H), 7.52 (m, 1H), 7.98 (s, 1H), 10.04 (br. s., 1H), 12.71 (s, 1H).

Example 13: (S)-6-bromo-2-(1-(2,6-dichlorophenyl)-2,5-dimethyl-1H-pyrrol-3-yl)-N-(1-(ethylsulfonyl) pyrrolidine-3-yl)-3H-imidazo[4,5-b]pyridine-7-amine

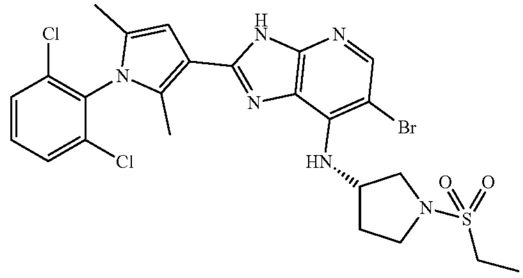

$^1$H NMR (300 MHz, DMSO-$d_6$) δ 1.18 (t, J=7.4, 3H), 1.92 (s, 3H), 2.13 (m, 1H), 2.33 (m, 4H), 3.08 (q, J=7.2 Hz, 2H), 3.30 (m, 1H), 3.36 (m, 1H), 3.50 (m, 1H), 3.70 (m, 1H), 5.63 (m, 1H), 5.79 (d, J=7.7 Hz, 1H), 6.68 (s, 1H), 7.63 (m, 1H), 7.79 (d, J=8.2 Hz, 2H), 7.99 (s, 1H), 12.78 (s, 1H).

Example 14:6-bromo-2-(1-(2,5-dichlorophenyl)-2,5-dimethyl-1H-pyrrol-3-yl)-N—((S)-1-(ethylsulfonyl) pyrrolidine-3-yl)-3H-imidazo[4,5-b]pyridine-7-amine

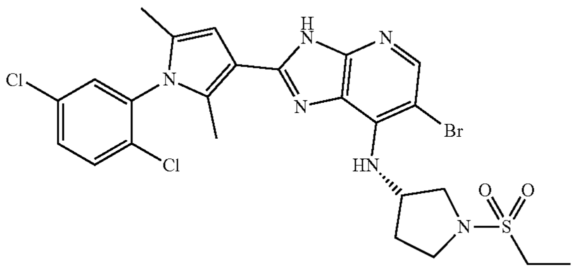

$^1$H NMR (300 MHZ, DMSO-$d_6$) δ 1.19 (t, J=7.3 Hz 3H), 1.95 (s, 3H), 2.12 (m, 1H), 2.29 (m, 1H), 2.34 (s, 3H), 3.09 (q, J=7.2 Hz, 2H), 3.28 (m, 1H), 3.36 (m, 1H), 3.50 (m, 1H), 3.68 (m, 1H), 5.63 (m, 1H), 5.78 (m, 1H), 6.63 (s, 1H), 7.69 (m, 1H), 7.79 (m, 2H), 7.98 (s, 1H), 12.77 (s, 1H).

Example 15: (S)-6-bromo-2-(1-(3,4-dichlorophenyl)-2,5-dimethyl-1H-pyrrol-3-yl)-N-(1-(ethylsulfonyl) pyrrolidine-3-yl)-3H-imidazo[4,5-b]pyridine-7-amine

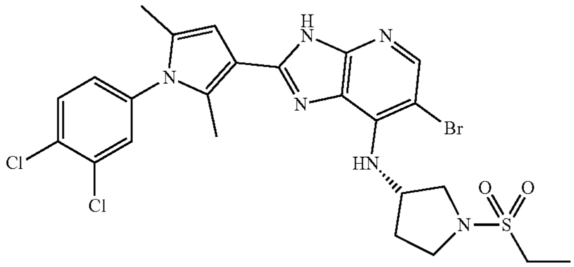

$^1$H NMR (300 MHZ, DMSO-$d_6$) δ 1.20 (t, J=7.4 Hz, 3H), 2.03 (s, 3H), 2.13 (m, 1H), 2.31 (m, 1H), 2.43 (s, 3H), 3.09 (q, J=7.2 Hz, 2H), 3.28 (s, 1H), 3.35 (m, 1H), 3.51 (m, 1H), 3.67 (m, 1H), 5.62 (m, 1H), 5.79 (d, J=7.5 Hz, 1H), 6.60 (s, 1H), 7.42 (d, J=8.5 Hz, 1H), 7.83 (m, 2H), 7.98 (d, J=1.5, 1H), 12.75 (s, 1H).

Example 16:6-bromo-2-(1-(2-chlorophenyl)-2,5-dimethyl-1H-pyrrol-3-yl)-N—((S)-1-(ethylsulfonyl) pyrrolidine-3-yl)-3H-imidazo[4,5-b]pyridine-7-amine

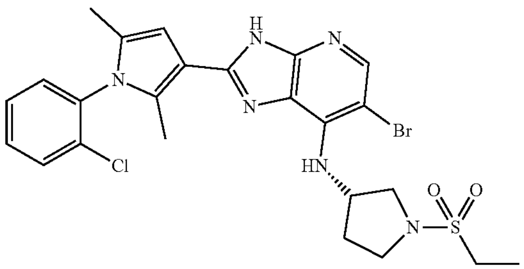

$^1$H NMR (300 MHZ, DMSO-$d_6$) δ 1.18 (t, J=7.3 Hz, 3H), 1.93 (s, 3H), 2.13 (m, 1H), 2.31 (m, 4H), 3.08 (q, J=7.1 Hz, 2H), 3.30 (m, 1H), 3.35 (m, 1H), 3.50 (m, 1H), 3.68 (m, 1H), 5.63 (m, 1H), 5.77 (d, J=7.5 Hz, 1H), 6.62 (s, 1H), 7.58 (m, 3H), 7.76 (m, 1H), 7.98 (s, 1H), 12.74 (s, 1H).

Example 17:3-(3-(6-bromo-7-(((S)-1-(ethylsulfonyl) pyrrolidine-3-yl)amino)-3H-imidazo[4,5-b]pyridine-2-yl)-2,5-dimethyl-1H-pyrrol-1-yl)-4-chlorobenzenesulfonamide

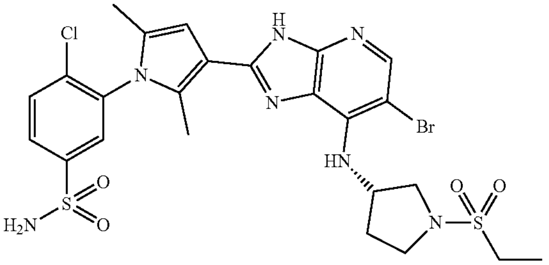

$^1$H NMR (300 MHZ, DMSO-$d_6$) δ 1.19 (t, J=7.1 Hz, 3H), 1.98 (s, 3H), 2.13 (m, 1H), 2.35 (m, 4H), 3.09 (q, J=7.5 Hz, 2H), 3.29 (m, 1H), 3.36 (m, 1H), 3.49 (m, 1H), 3.69 (m, 1H), 5.63 (m, 1H), 5.80 (d, J=7 Hz, 1H), 6.67 (s, 1H), 7.60 (s, 2H), 7.88 (m, 1H), 8.00 (s, 3H), 12.80 (s, 1H).

Example 18: (S)-3-(3-(6-bromo-7-((1-(ethylsulfonyl) pyrrolidine-3-yl)amino)-1H-imidazo[4,5-b] pyridine-2-yl)-2,5-dimethyl-1H-pyrrol-1-yl)-N-methylbenzenesulfonamide

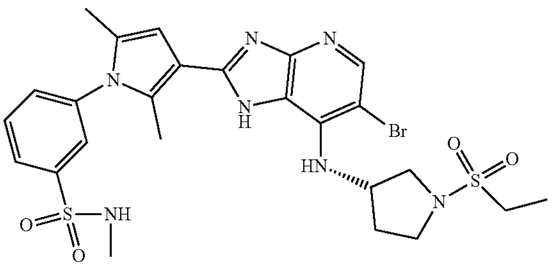

$^1$H NMR (300 MHZ, DMSO-$d_6$) δ 1.19 (t, J=7.30 Hz, 3H), 2.03 (s, 3H), 2.13 (m, 1H), 2.31 (m, 1H), 2.42 (s, 3H), 2.47 (s, 3H), 3.08 (q, J=7.26 Hz, 2H), 3.29 (m, 1H), 3.36 (m, 1H,) 3.51 (m, 1H), 3.68 (m, 1H), 5.62 (m, 1H), 5.78 (d, J=7.92 Hz, 1H), 6.64 (s, 1H), 7.59 (br. s., 1H), 7.70 (m, 2H), 7.82 (t, J=7.68 Hz, 1H), 7.91 (m, 1H), 7.99 (s, 1H), 12.76 (br. s., 1H).

Example 19: (S)-3-(3-(6-bromo-7-((1-(ethylsulfonyl) pyrrolidine-3-yl)amino)-1H-imidazo[4,5-b] pyridine-2-yl)-2,5-dimethyl-1H-pyrrol-1-yl)-N-ethylbenzenesulfonamide

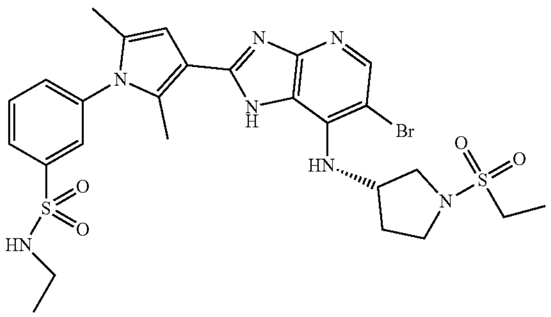

$^1H$ NMR (300 MHZ, DMSO-$d_6$) δ 0.97 (t, J=7.2, 3H), 1.18 (m, 3H), 2.03 (s, 3H), 2.13 (m, 1H), 2.31 (m, 1H), 2.42 (s, 3H), 2.85 (m, 2H), 3.08 (q, J=7.4 Hz, 2H), 3.28 (m, 1H), 3.36 (m, 1H), 3.51 (m, 1H), 3.68 (m, 1H), 5.62 (m, 1H), 5.77 (m, 1H), 6.64 (s, 1H), 7.69 (m, 3H), 7.81 (t, J=7.8, 1H), 7.92 (d, J=7.7 Hz, 1H), 7.99 (s, 1H), 12.77 (br. s., 1H).

Example 20: (S)-3-(3-(6-bromo-7-((1-(ethylsulfonyl) pyrrolidine-3-yl)amino)-1H-imidazo[4,5-b] pyridine-2-yl)-2,5-dimethyl-1H-pyrrol-1-yl)benzamide

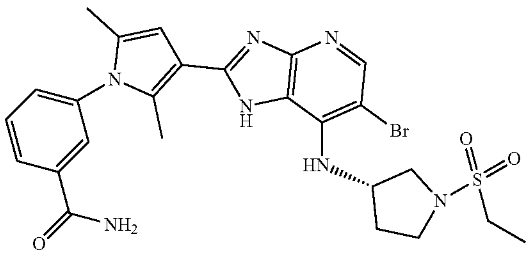 [SMILES: CCS(=O)(=O)N1CC[C@H](Nc2c(Br)cnc3nc(-c4cc(C)n(-c5cccc(C(N)=O)c5)c4C)[nH]c23)C1]

$^1H$ NMR (300 MHZ, DMSO-$d_6$) δ 1.19 (t, J=6.5 Hz, 3H), 2.01 (s, 3H), 2.12 (m, 1H), 2.32 (m, 1H), 2.41 (s, 3H), 3.08 (q, J=7.4 Hz, 2H), 3.22 (m, 1H), 3.49 (m, 2H), 3.67 (m, 1H), 5.63 (d, J=5.3 Hz, 1H), 5.76 (d, J=7.2 Hz, 1H), 6.61 (s, 1H), 7.53 (m, 2H), 7.66 (t, 7.4 Hz, 1H), 7.83 (s, 1H), 8.01 (m, 2H), 8.11 (s, 1H), 12.77 (s, 1H).

Example 21: (S)-6-bromo-N-(1-(ethylsulfonyl) pyrrolidine-3-yl)-2-(1-(3-(2-methoxyethoxy)phenyl)-2,5-dimethyl-1H-pyrrol-3-yl)-1H-imidazo[4,5-b]pyridine-7-amine

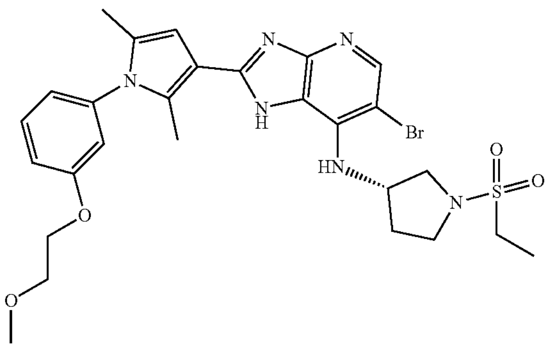 [SMILES: CCS(=O)(=O)N1CC[C@H](Nc2c(Br)cnc3nc(-c4cc(C)n(-c5cccc(OCCOC)c5)c4C)[nH]c23)C1]

$^1H$ NMR (300 MHZ, DMSO-$d_6$) δ 1.19 (t, J=7.4 Hz, 3H), 2.02 (s, 3H), 2.13 (m, 1H), 2.31 (m, 1H), 2.41 (s, 3H), 3.09 (q, J=7.4 Hz, 2H), 3.28 (m, 1H), 3.36 (m, 1H), 3.50 (m, 1H), 3.68 (m, 3H), 4.16 (m, 2H), 5.62 (m, 1H), 5.76 (m, 1H), 6.57 (s, 1H), 6.9 (m, 2H), 7.08 (d, J=8.6 Hz, 1H), 7.46 (m, 1H), 7.97 (s, 1H), 12.69 (s, 1H).

Example 22: (S)-6-bromo-N-(1-(ethylsulfonyl) pyrrolidine-3-yl)-2-(1-(4-(2-methoxyethoxy)phenyl)-2,5-dimethyl-1H-pyrrol-3-yl)-1H-imidazo[4,5-b]pyridine-7-amine

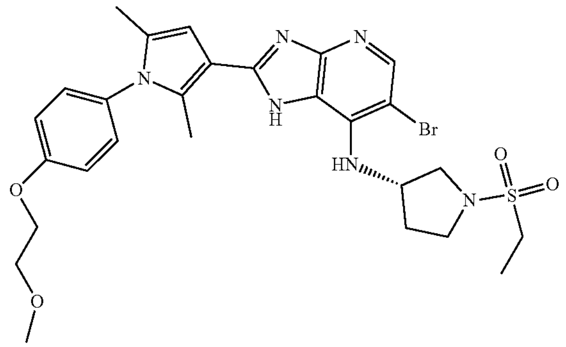 [SMILES: CCS(=O)(=O)N1CC[C@H](Nc2c(Br)cnc3nc(-c4cc(C)n(-c5ccc(OCCOC)cc5)c4C)[nH]c23)C1]

$^1H$ NMR (300 MHZ, $CDCl_3$) δ 1.38 (t, J=7.4 Hz, 3H), 2.10 (m, 4H), 2.48 (m, 4H), 3.02 (m, 2H), 3.50 (s, 4H), 3.57 (m, 1H), 3.65 (m, 1H), 3.84 (m, 3H), 4.21 (m, 2H), 5.02 (d, J=8 Hz, 1H), 5.75 (m, 1H), 6.42 (s, 1H), 7.06 (d, J=8.4, 2H), 7.18 (d, J=8.2 Hz, 2H), 8.18 (s, 1H), 12.26 (s, 1H).

Example 23: (S)-3-(3-(6-bromo-7-((1-(ethylsulfonyl) pyrrolidine-3-yl)amino)-1H-imidazo[4,5-b] pyridine-2-yl)-2,5-dimethyl-1H-pyrrol-1-yl)benzenesulfonamide

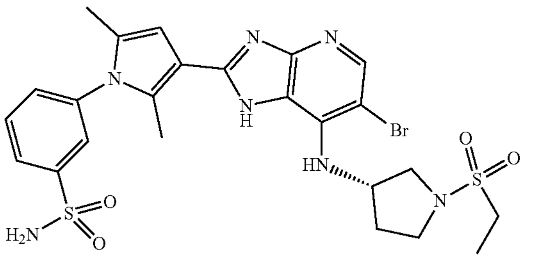 [SMILES: CCS(=O)(=O)N1CC[C@H](Nc2c(Br)cnc3nc(-c4cc(C)n(-c5cccc(S(N)(=O)=O)c5)c4C)[nH]c23)C1]

$^1$H NMR (300 MHZ, DMSO-$d_6$) δ 1.19 (t, J=7.1 Hz, 3H), 2.03 (s, 3H), 2.13 (m, 1H), 2.31 (m, 1H), 2.42 (s, 3H), 3.09 (q, J=7.2 Hz, 2H), 3.28 (m, 1H), 3.36 (m, 1H), 3.51 (m, 1H), 3.67 (m, 1H), 5.63 (m, 1H), 5.78 (d, J=7.6 Hz, 1H), 6.63 (s, 1H), 7.50 (br. s., 2H), 7.64 (d, J=8.7 Hz, 1H), 7.77 (m, 2H), 7.96 (m, 2H), 12.74 (s, 1H).

Example 24: (S)-4-(3-(6-bromo-7-((1-(ethylsulfonyl) pyrrolidine-3-yl)amino)-1H-imidazo[4,5-b] pyridine-2-yl)-2,5-dimethyl-1H-pyrrol-1-yl)benzenesulfonamide

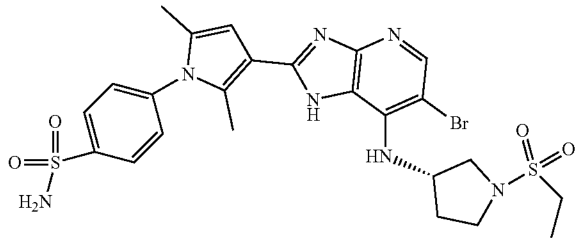 [SMILES: CCS(=O)(=O)N1CC[C@H](Nc2c(Br)cnc3nc(-c4cc(C)n(-c5ccc(S(N)(=O)=O)cc5)c4C)[nH]c23)C1]

$^1$H NMR (300 MHz, DMSO-$d_6$) δ 1.19 (t, J=7.3 Hz, 3H), 2.04 (s, 3H), 2.11 (m, 1H), 2.34 (m, 1H), 2.43 (s, 3H), 3.09 (m, 2H), 3.28 (m, 1H), 3.39 (m, 1H), 3.49 (m, 1H), 3.69 (m, 1H), 5.62 (m, 1H), 5.79 (d, J=7.9 Hz, 1H), 6.63 (s, 1H), 7.47 (br. s., 2H), 7.6 (d, J=8.5 Hz, 2H), 8.00 (m, 3H), 12.43 (br. s., 1H).

Example 25 (S)-6-bromo-2-(2,5-dimethyl-1-phenyl-1H-pyrrol-3-yl)-N-(1-(ethylsulfonyl) pyrrolidine-3-yl)-3H-imidazo[4,5-b]pyridine-7-amine

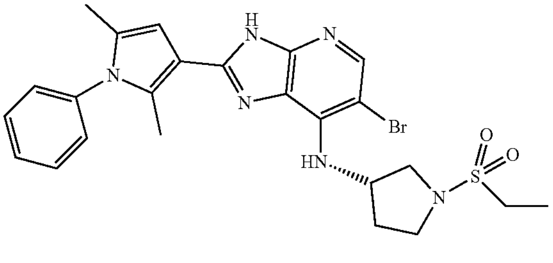

$^1$H NMR (300 MHZ, DMSO-$d_6$) δ 1.19 (t, J=7.3 Hz, 3H), 2.00 (s, 3H), 2.15 (m, 1H), 2.32 (m, 1H), 2.39 (s, 3H), 3.08 (q, J=7.5 Hz, 2H), 3.28 (m, 1H), 3.38 (m, 1H), 3.51 (m, 1H), 3.68 (m, 1H), 5.64 (m, 1H), 5.77 (d, J=7.6 Hz, 1H), 6.59 (s, 1H), 7.35 (d, J=7 Hz, 2H), 7.53 (m, 3H), 7.98 (s, 1H), 12.70 (s, 1H).

Hereinafter, the compounds of Examples 26 to 48 were synthesized according to the representative synthesis method 3.

Example 26:3-((6-bromo-2-(1-(2,6-dichlorophenyl)-2,5-dimethyl-1H-pyrrol-3-yl)-3H-imidazo[4,5-b] pyridine-7-yl)amino)benzenesulfonamide

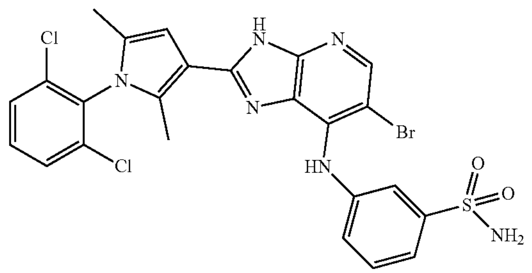 [SMILES: Cc1cc(-c2nc3c(Nc4cccc(S(N)(=O)=O)c4)c(Br)cnc3[nH]2)c(C)n1-c1c(Cl)cccc1Cl]

$^1$H NMR (300 MHZ, DMSO-$d_6$) δ 1.89 (s, 3H), 1.97 (s, 3H), 6.64 (s, 1H), 7.21 (m, 3H), 7.33 (m, 2H), 7.6 (m, 2H), 7.75 (m, 2H), 8.21 (s, 1H), 8.54 (s, 1H), 12.91 (s, 1H).

Example 27:3-((6-bromo-2-(2,5-dimethyl-1-(4-(morpholine-4-carbonyl)phenyl)-1H-pyrrol-3-yl)-3H-imidazo[4,5-b]pyridine-7-yl)amino)benzenesulfonamide

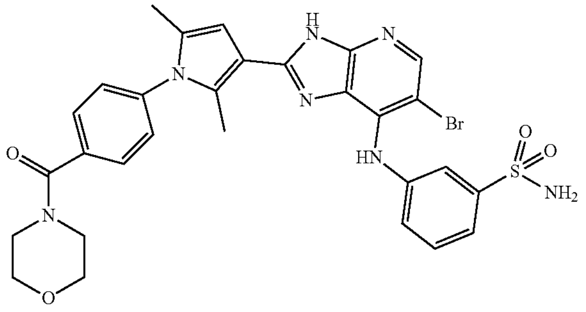 [SMILES: Cc1cc(-c2nc3c(Nc4cccc(S(N)(=O)=O)c4)c(Br)cnc3[nH]2)c(C)n1-c1ccc(C(=O)N2CCOCC2)cc1]

$^1$H NMR (300 MHZ, DMSO-$d_6$) δ 2.00 (s, 3H), 2.09 (s, 3H), 3.44 (m, 2H), 3.63 (s, 6H), 6.60 (s, 1H), 7.19 (s, 3H), 7.34 (m, 4H), 7.57 (m, 3H), 8.20 (s, 1H), 8.52 (s, 1H), 12.85 (s, 1H).

Example 28:3-((6-bromo-2-(2,5-dimethyl-1-(3-(morpholine-4-carbonyl)phenyl)-1H-pyrrol-3-yl)-3H-imidazo[4,5-b]pyridine-7-yl)amino)benzenesulfonamide

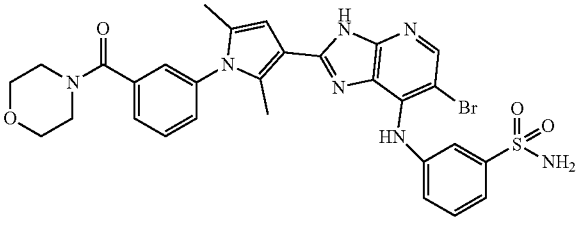 [SMILES: Cc1cc(-c2nc3c(Nc4cccc(S(N)(=O)=O)c4)c(Br)cnc3[nH]2)c(C)n1-c1cccc(C(=O)N2CCOCC2)c1]

$^1$H NMR (300 MHZ, DMSO-$d_6$) δ 2.00 (s, 3H), 2.15 (s, 3H), 3.62 (br. s., 8H), 6.58 (s, 1H), 7.16 (m, 2H), 7.33 (m, 5H), 7.58 (m, 4H), 8.19 (s, 1H) 12.85 (br. s., 1H).

Example 29:3-((6-bromo-2-(2,5-dimethyl-1-(4-(morpholinosulfonyl)phenyl)-1H-pyrrol-3-yl)-3H-imidazo[4,5-b]pyridine-7-yl)amino)benzenesulfonamide

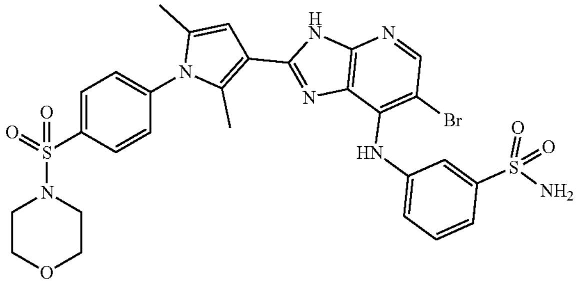 [SMILES: Cc1cc(-c2nc3c(Nc4cccc(S(N)(=O)=O)c4)c(Br)cnc3[nH]2)c(C)n1-c1ccc(S(=O)(=O)N2CCOCC2)cc1]

$^1$H NMR (300 MHZ, DMSO-$d_6$) δ 2.02 (s, 3H), 2.13 (s, 3H), 2.95 (t, J=4.2 Hz 4H), 3.67 (t, J=4.2 Hz, 4H), 6.64 (s, 1H), 7.20 (s, 3H), 7.32 (m, 2H), 7.55 (s, 1H), 7.62 (d, J=8.5 Hz, 2H), 7.89 (d, J=8.5 Hz, 2H), 8.22 (s, 1H), 8.53 (s, 1H), 12.86 (s, 1H).

Example 30:3-((6-bromo-2-(2,5-dimethyl-1-(3-(morpholinosulfonyl)phenyl)-1H-pyrrol-3-yl)-3H-imidazo[4,5-b]pyridine-7-yl)amino)benzenesulfonamide

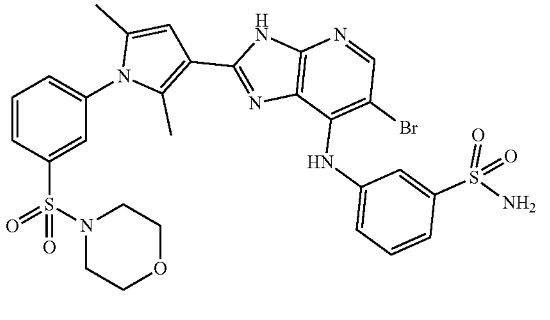 [SMILES: Cc1cc(-c2nc3c(Nc4cccc(S(N)(=O)=O)c4)c(Br)cnc3[nH]2)c(C)n1-c1cccc(S(=O)(=O)N2CCOCC2)c1]

$^1$H NMR (300 MHz, DMSO-$d_6$) δ 2.01 (s, 3H), 2.09 (s, 3H), 2.93 (m, 4H), 3.65 (m, 4H), 6.63 (s, 1H), 7.19 (m, 3H), 7.32 (m, 2H), 7.54 (s, 2H), 7.73 (m, 1H), 7.86 (m, 2H), 8.21 (s, 1H), 8.51 (s, 1H), 12.90 (s, 1H).

Example 31:3-((6-bromo-2-(1-(2-chlorophenyl)-2,5-dimethyl-1H-pyrrol-3-yl)-3H-imidazo[4,5-b]pyridine-7-yl)amino)benzenesulfonamide

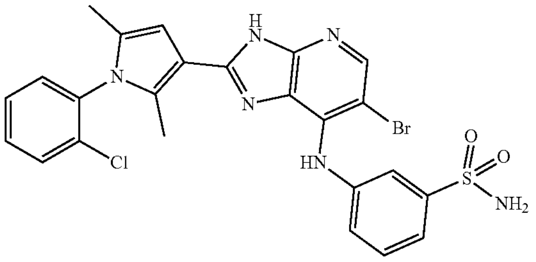 [SMILES: Cc1cc(-c2nc3c(Nc4cccc(S(N)(=O)=O)c4)c(Br)cnc3[nH]2)c(C)n1-c1ccccc1Cl]

$^1$H NMR (300 MHZ, DMSO-$d_6$) δ 1.9 (s, 3H), 1.98 (s, 3H), 6.6 (s, 1H), 7.19 (s, 3H), 7.32 (m, 2H), 7.46 (d, J=6.1 Hz, 1H), 7.56 (m, 3H), 7.72 (m, 1H), 8.2 (s, 1H), 8.52 (s, 1H), 12.87 (s, 1H).

Example 32:3-((6-bromo-2-(2,5-dimethyl-1-(2-methyl-4-(methylsulfonamido)phenyl)-1H-pyrrol-3-yl)-3H-imidazo[4,5-b]pyridine-7-yl)amino)benzenesulfonamide

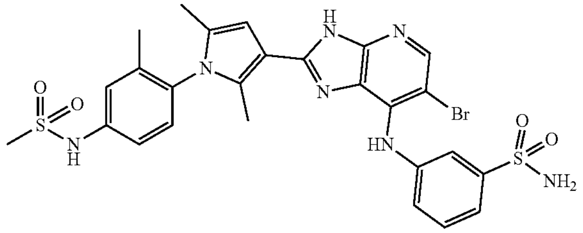 [SMILES: Cc1cc(NS(C)(=O)=O)ccc1-n1c(C)cc(-c2nc3c(Nc4cccc(S(N)(=O)=O)c4)c(Br)cnc3[nH]2)c1C]

$^1$H NMR (300 MHz, DMSO-$d_6$) δ 1.84 (s, 3H), 1.87 (s, 3H), 1.96 (s, 3H), 3.01 (s, 3H), 6.59 (s, 1H), 6.96 (d, J=2.1 Hz, 1H), 7.18 (s, 2H), 7.23 (s, 1H), 7.33 (m, 4H), 7.54 (s, 1H), 8.2 (s, 1H), 8.51 (s, 1H), 9.89 (s, 1H), 12.85 (s, 1H).

Example 33:3-((6-bromo-2-(2,5-dimethyl-1-(2-methyl-5-(methylsulfonamido)phenyl)-1H-pyrrol-3-yl)-3H-imidazo[4,5-b]pyridine-7-yl)amino)benzenesulfonamide

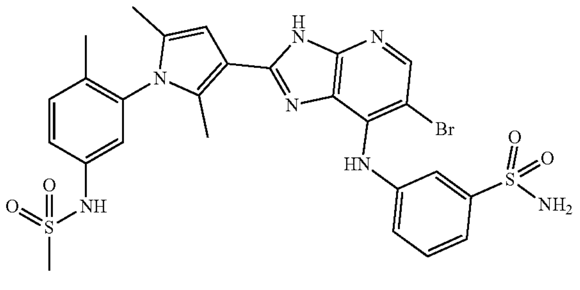 [SMILES: Cc1ccc(NS(C)(=O)=O)cc1-n1c(C)cc(-c2nc3c(Nc4cccc(S(N)(=O)=O)c4)c(Br)cnc3[nH]2)c1C]

$^1$H NMR (300 MHZ, DMSO-$d_6$) δ 1.82 (s, 3H), 1.88 (s, 3H), 1.96 (s, 3H), 3.01 (s, 3H), 6.59 (s, 1H), 6.96 (d, J=2.1 Hz, 1H), 7.18 (s, 2H), 7.23 (s, 1H), 7.33 (m, 4H), 7.54 (s, 1H), 8.2 (s, 1H), 8.51 (s, 1H), 9.89 (s, 1H), 12.85 (s, 1H).

Example 34:3-((6-bromo-2-(2,5-dimethyl-1-(2-methyl-3-(methylsulfonamido)phenyl)-1H-pyrrol-3-yl)-3H-imidazo[4,5-b]pyridine-7-yl)amino)benzene-sulfonamide

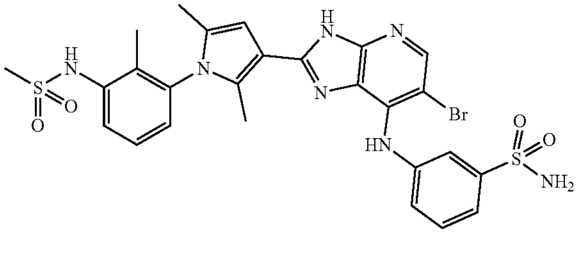 [SMILES: Cc1c(NS(C)(=O)=O)cccc1-n1c(C)cc(-c2nc3c(Nc4cccc(S(N)(=O)=O)c4)c(Br)cnc3[nH]2)c1C]

$^1$H NMR (300 MHZ, DMSO-$d_6$) δ 1.82 (s, 3H), 1.86 (s, 3H), 1.95 (s, 3H), 3.04 (s, 3H), 6.60 (s, 1H), 7.16 (m, 4H), 7.38 (m, 4H), 7.54 (s, 1H), 8.2 (s, 1H), 8.51 (s, 1H), 9.28 (s, 1H), 12.85 (s, 1H).

Example 35:3-((6-bromo-2-(1-(2,5-dichlorophenyl)-2,5-dimethyl-1H-pyrrol-3-yl)-3H-imidazo[4,5-b]pyridine-7-yl)amino)benzenesulfonamide

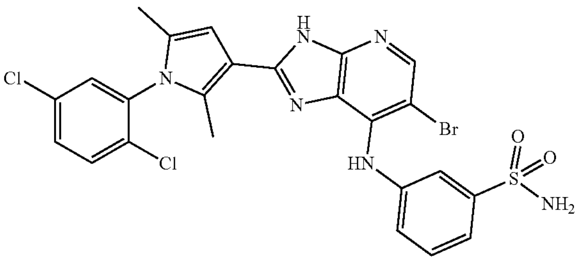 [SMILES: Cc1cc(-c2nc3c(Nc4cccc(S(N)(=O)=O)c4)c(Br)cnc3[nH]2)c(C)n1-c1cc(Cl)ccc1Cl]

$^1$H NMR (300 MHZ, DMSO-$d_6$) δ 1.92 (s, 3H), 2.00 (s, 3H), 6.60 (s, 1H), 7.2 (m, 3H), 7.32 (m, 2H), 7.57 (s, 1H), 7.68 (m, 2H), 7.77 (m, 1H), 8.21 (s, 1H), 8.53 (s, 1H), 12.88 (s, 1H).

Example 36:3-(3-(6-bromo-7-((3-sulfamoylphenyl)amino)-3H-imidazo[4,5-b]pyridine-2-yl)-2,5-dimethyl-1H-pyrrole-1-yl)-4-chlorobenzenesulfonamide

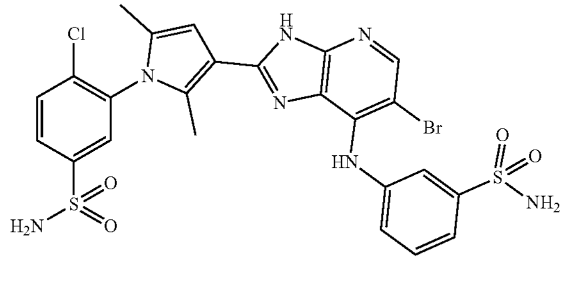 [SMILES: Cc1cc(-c2nc3c(Nc4cccc(S(N)(=O)=O)c4)c(Br)cnc3[nH]2)c(C)n1-c1cc(S(N)(=O)=O)ccc1Cl]

$^1$H NMR (300 MHz, DMSO-$d_6$) δ 1.93 (s, 3H), 2.01 (s, 3H), 6.64 (s, 1H), 7.20 (s, 3H), 7.32 (m, 3H), 7.56 (s, 2H), 7.81 (s, 1H), 7.97 (s, 2H), 8.22 (s., 1H), 8.53 (s, 1H) 12.86 (br. s., 1H).

Example 37:3-((6-bromo-2-(2,5-dimethyl-1-(3-morpholinophenyl)-1H-pyrrol-3-yl)-3H-imidazo[4,5-b]pyridine-7-yl)amino)benzenesulfonamide

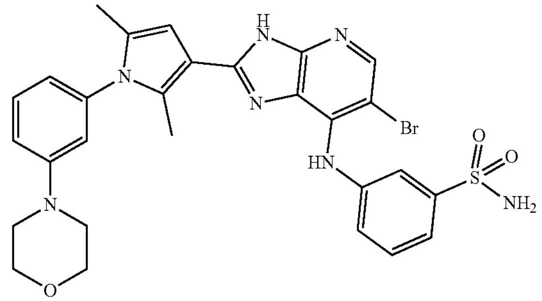 [SMILES: Cc1cc(-c2nc3c(Nc4cccc(S(N)(=O)=O)c4)c(Br)cnc3[nH]2)c(C)n1-c1cccc(N2CCOCC2)c1]

$^1$H NMR (300 MHz, DMSO-$d_6$) 1.99 (s, 3H), 2.07 (s, 3H), 3.16 (m, 4H), 3.73 (m, 4H), 6.54 (s, 1H), 6.65 (d, J=7.1 Hz, 1H), 6.77 (s, 1H), 7.03 (m, 1H), 7.20 (m, 3H), 7.35 (m, 3H), 7.55 (s, 1H), 8.19 (s, 1H), 8.49 (s, 1H), 12.80 (s., 1H).

Example 38:3-((6-bromo-2-(2,5-dimethyl-1-(3-(2-morpholinoethoxy)phenyl)-1H-pyrrol-3-yl)-1H-imidazo[4,5-b]pyridine-7-yl)amino)benzenesulfonamide

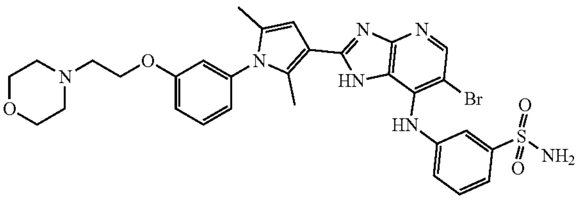 [SMILES: Cc1cc(-c2nc3ncc(Br)c(Nc4cccc(S(N)(=O)=O)c4)c3[nH]2)c(C)n1-c1cccc(OCCN2CCOCC2)c1]

$^1$H NMR (300 MHZ, DMSO-$d_6$) δ 1.99 (s, 3H), 2.07 (s, 3H), 2.46 (m, 4H), 2.69 (t, J=5.7 Hz, 2H), 3.57 ((t, J=4.7 Hz, 4H), 4.12 (t, J=5.9 Hz, 2H), 6.55 (s, 1H), 6.83 (m, 2H), 7.06 (d, J=7.5 Hz, 1H), 7.20 (m, 3H), 7.32 (m, 2H), 7.43 (t, J=8.1, 1H), 7.55 (s, 1H), 8.19 (s, 1H), 8.5 (s, 1H), 12.81 (s, 1H).

Example 39:3-((6-bromo-2-(2,5-dimethyl-1-(4-(2-morpholinoethoxy)phenyl)-1H-pyrrol-3-yl)-1H-imidazo[4,5-b]pyridine-7-yl)amino)benzenesulfonamide

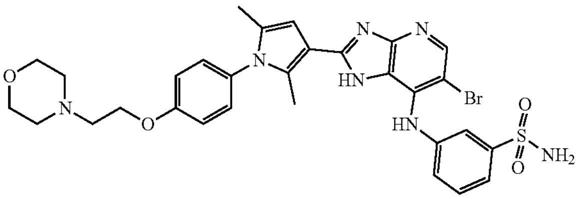 [SMILES: Cc1cc(-c2nc3ncc(Br)c(Nc4cccc(S(N)(=O)=O)c4)c3[nH]2)c(C)n1-c1ccc(OCCN2CCOCC2)cc1]

$^1$H NMR (300 MHZ, DMSO-$d_6$) δ 1.95 (s, 3H), 2.04 (s, 3H), 2.47 (m, 4H), 2.72 (t, J=5.5 Hz, 2H), 3.59 (t, J=5.8 Hz, 4H), 4.14 (t, J=5.8 Hz, 2H), 6.54 (s, 1H), 7.07 (m, 2H), 7.18 (m, 5H), 7.3 (m, 2H), 7.54 (s, 1H), 8.19 (s, 1H), 8.5 (s, 1H), 12.8 (s, 1H).

Example 40:3-((6-bromo-2-(2,5-dimethyl-1-(4-morpholinophenyl)-1H-pyrrol-3-yl)-3H-imidazo[4,5-b]pyridine-7-yl)amino)benzenesulfonamide

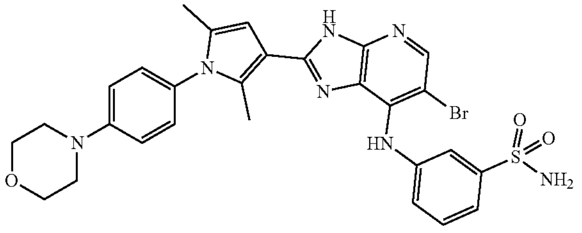 [SMILES: Cc1cc(-c2nc3c(Nc4cccc(S(N)(=O)=O)c4)c(Br)cnc3[nH]2)c(C)n1-c1ccc(N2CCOCC2)cc1]

$^1$H NMR (300 MHZ, DMSO-$d_6$) δ 1.96 (s, 3H), 2.04 (s, 3H), 3.19 (t, J=3.8 Hz, 4H), 3.76 (t, J=3.8 Hz, 4H), 6.53 (s, 1H), 7.07 (q, J=8.5 Hz, 4H), 7.19 (s, 3H), 7.3 (m, 2H), 7.54 (s, 1H), 8.19 (s, 1H), 8.5 (s, 1H), 12.78 (s, 1H).

Example 41:3-((2-(1-(benzo[d][1,3]dioxole-5-yl)-2,5-dimethyl-1H-pyrrol-3-yl)-6-bromo-3H-imidazo[4,5-b]pyridine-7-yl)amino)benzenesulfonamide

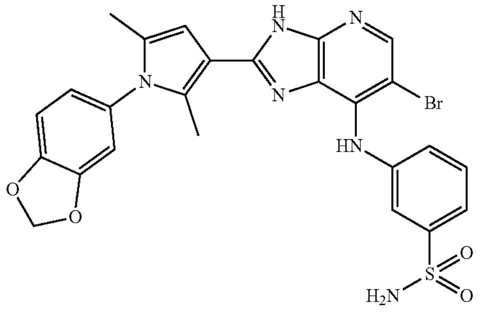 [SMILES: Cc1cc(-c2nc3c(Nc4cccc(S(N)(=O)=O)c4)c(Br)cnc3[nH]2)c(C)n1-c1ccc2c(c1)OCO2]

$^1$H NMR (300 MHz, DMSO-$d_6$) δ 1.98 (s, 3H), 2.07 (s, 3H), 6.14 (s, 2H), 6.53 (s, 1H), 6.72 (d, J=8.4 Hz, 1H), 6.91 (s, 1H), 7.04 (d, J=8.1 Hz, 1H), 7.19 (s, 3H), 7.32 (m, 2H), 7.54 (s, 1H), 8.19 (s, 1H), 8.50 (s, 1H), 12.81 (s, 1H).

Example 42:3-((6-bromo-2-(1-(3-(2-methoxyethoxy)phenyl)-2,5-dimethyl-1H-pyrrol-3-yl)-1H-imidazo[4,5-b]pyridine-7-yl)amino)benzenesulfonamide

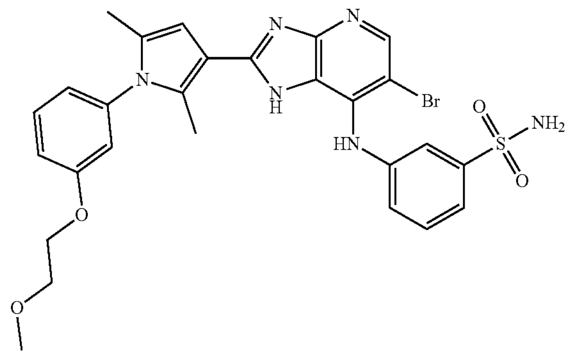 [SMILES: COCCOc1cccc(-n2c(C)cc(-c3nc4ncc(Br)c(Nc5cccc(S(N)(=O)=O)c5)c4[nH]3)c2C)c1]

$^1$H NMR (300 MHZ, DMSO-$d_6$) δ 1.99 (s, 3H), 2.08 (s, 3H), 3.31 (s, 3H), 3.66 (m, 2H), 4.14 (m, 2H), 6.55 (s, 1H), 6.83 (m, 2H), 7.06 (m, 1H), 7.26 (m, 5H), 7.44 (m, 1H), 7.55 (m 1H), 8.19 (s, 1H), 8.5 (s, 1H), 12.82 (s, 1H).

Example 43:3-((6-bromo-2-(2,5-dimethyl-1-phenyl-1H-pyrrol-3-yl)-1H-imidazo[4,5-b]pyridine-7-yl)amino)benzenesulfonamide

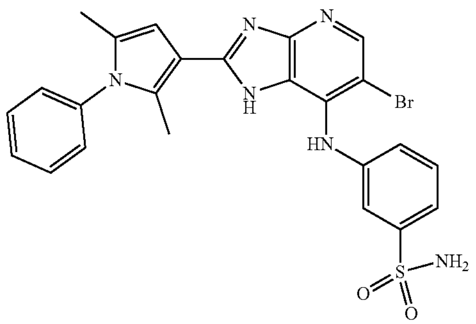 [SMILES: Cc1cc(-c2nc3ncc(Br)c(Nc4cccc(S(N)(=O)=O)c4)c3[nH]2)c(C)n1-c1ccccc1]

$^1$H NMR (300 MHZ, DMSO-$d_6$) δ 1.97 (s, 3H), 2.06 (s, 3H), 6.57 (s, 1H), 7.18 (m, 3H), 7.30 (m, 4H), 7.55 (m, 4H), 8.20 (s, 1H), 8.49 (s, 1H), 12.82 (br. s., 1H).

Example 44:3-(3-(7-(benzo[d][1,3]dioxole-5-ylamino)-6-bromo-3H-imidazo[4,5-b]pyridine-2-yl)-2,5-dimethyl-1H-pyrrol-1-yl)benzenesulfonamide

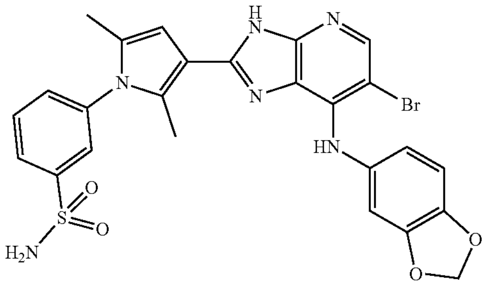 [SMILES: Cc1cc(-c2nc3c(Nc4ccc5c(c4)OCO5)c(Br)cnc3[nH]2)c(C)n1-c1cccc(S(N)(=O)=O)c1]

$^1$H NMR (300 MHZ, DMSO-$d_6$) δ 2.00 (s, 3H), 2.11 (s, 3H), 5.88 (s, 2H), 6.59 (s, 1H), 6.67 (m, 1H), 6.76 (m, 2H), 7.52 (br. s., 2H), 7.60 (m, 1H), 7.68 (s, 1H), 7.76 (m, 1H), 7.92 (m, 2H), 8.10 (s, 1H) 12.72 (br. s., 1H).

Example 45:2-(1-(benzo[d][1,3]dioxole-5-yl)-2,5-dimethyl-1H-pyrrol-3-yl)-6-bromo-N-(4-(2-methoxyethoxy)phenyl)-3H-imidazo[4,5-b]pyridine-7-amine

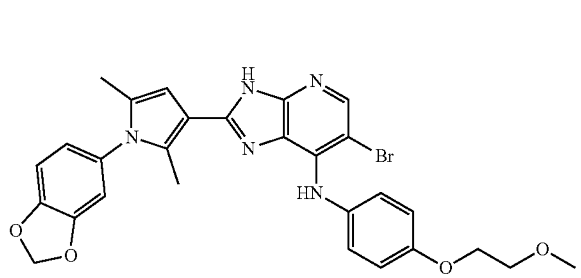 [SMILES: COCCOc1ccc(Nc2c(Br)cnc3[nH]c(-c4cc(C)n(-c5ccc6c(c5)OCO6)c4C)nc23)cc1]

$^1$H NMR (300 MHZ, DMSO-$d_6$) δ 1.97 (s, 3H), 2.02 (s, 3H), 3.23 (s, 3H), 3.59 (m, 2H), 4.00 (m, 2H), 6.14 (s, 2H), 6.49 (s, 1H), 6.71 (d, J=7.8 Hz, 1H), 6.81 (m, J=8.6 Hz, 2H), 6.91 (s, 1H), 7.04 (d, J=8.3 Hz, 1H), 7.11 (m, J=9 Hz, 2H), 7.8 (s, 1H), 8.07 (s, 1H), 12.60 (s, 1H).

Example 46:3-(3-(6-bromo-7-((4-(2-methoxyethoxy) phenyl)amino)-3H-imidazo[4,5-b]pyridine-2-yl)-2,5-dimethyl-1H-pyrrol-1-yl)benzenesulfonamide

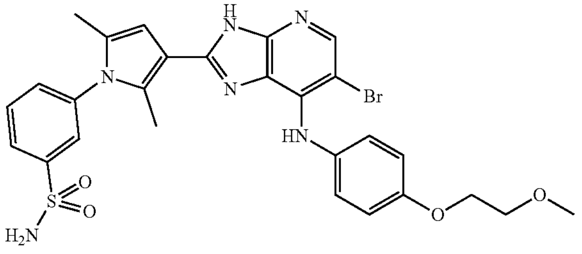 [SMILES: COCCOc1ccc(Nc2c(Br)cnc3[nH]c(-c4cc(C)n(-c5cccc(S(N)(=O)=O)c5)c4C)nc23)cc1]

$^1$H NMR (300 MHz, DMSO-$d_6$) δ 1.99 (s, 3H), 2.04 (s, 3H), 3.19 (s, 3H), 3.57 (t, J=4.5 Hz, 2H), 3.98 (m, 2H), 6.58 (s, 1H), 6.80 (d, J=9 Hz, 2H), 7.11 (d, J=8.8 Hz, 2H), 7.52 (s, 2H), 7.57 (m, 1H), 7.66 (s, 1H), 7.75 (m, 1H), 7.83 (s, 1H), 7.91 (m, 1H), 8.08 (s, 1H), 12.68 (s, 1H).

Example 47:3-((6-bromo-2-(2,5-dimethyl-1-(pyridine-3-yl)-1H-pyrrol-3-yl)-1H-imidazo[4,5-b]pyridine-7-yl)amino)benzenesulfonamide

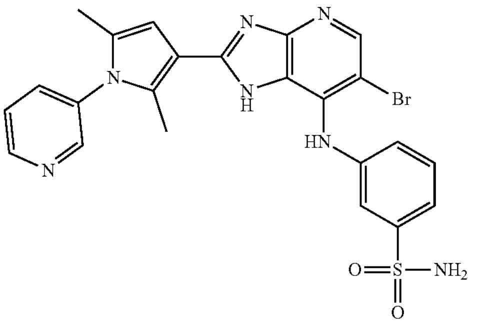 [SMILES: Cc1cc(-c2nc3ncc(Br)c(Nc4cccc(S(N)(=O)=O)c4)c3[nH]2)c(C)n1-c1cccnc1]

$^1$H NMR (300 MHz, DMSO-$d_6$) δ 1.99 (s, 3H), 2.08 (s, 3H), 6.62 (s, 1H), 7.2 (m, 4H), 7.32 (m, 2H), 7.58 (m, 2H), 7.81 (m, 1H), 8.21 (s, 1H), 8.53 (d, J=7.3, 2H), 8.69 (d, J=3.9, 1H), 12.87 (s, 1H).

Example 48:3-((6-bromo-2-(2,5-dimethyl-1-(pyridine-4-ylmethyl)-1H-pyrrol-3-yl)-1H-imidazo[4,5-b] pyridine-7-yl)amino)benzenesulfonamide

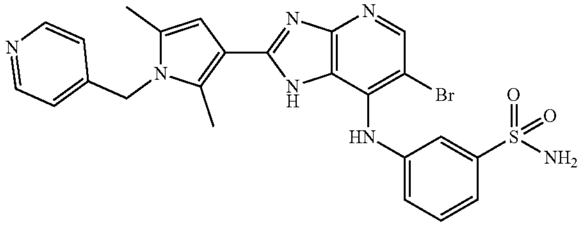 [SMILES: Cc1cc(-c2nc3ncc(Br)c(Nc4cccc(S(N)(=O)=O)c4)c3[nH]2)c(C)n1Cc1ccncc1]

$^1$H NMR (300 MHZ, DMSO-$d_6$) δ 2.09 (s, 3H), 2.22 (s, 3H), 5.16 (s, 2H), 6.53 (s, 1H), 6.87 (d, J=4.7, 2H), 7.19 (s, 3H), 7.31 (m, 2H), 7.54 (s, 1H), 8.19 (s, 1H), 8.49 (d, J=5.9, 3H), 12.8 (s, 1H).

Hereinafter, the compounds of Examples 49 to 54 were synthesized according to the representative synthesis method 1.

Example 49: (S)-2-(1-(benzo[d][1,3]dioxole-5-yl)-2,5-dimethyl-1H-pyrrol-3-yl)-6-bromo-N-(1-(ethylsulfonyl) pyrrolidine-3-yl)-3H-imidazo[4,5-b]pyridine-7-amine

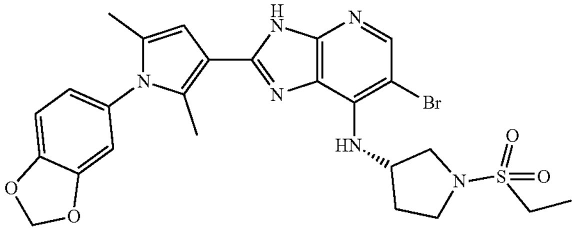

$^1$H NMR (300 MHZ, CHLOROFORM-d) δ 1.37 (t, J=7.36, 3H), 2.11 (s, 4H), 2.45 (s, 4H), 3.03 (br. s., 2H), 3.55 (m, 3H), 3.85 (m, 1H), 5.01 (d, J=8.47, 1H), 5.74 (br. s., 1H), 6.09 (s, 2H), 6.36 (s, 1H), 6.73 (m, 2H), 6.92 (d, J=8.01, 1H), 8.15 (s, 1H), 11.56 (br. s., 1H).

Example 50: N-(3-(3-(7-(((S)-1-(ethylsulfonyl) pyrrolidine-3-yl)amino)-3H-imidazo[4,5-b]pyridine-2-yl)-2,5-dimethyl-1H-pyrrol-1-yl)-4-methylphenyl) methanesulfonamide

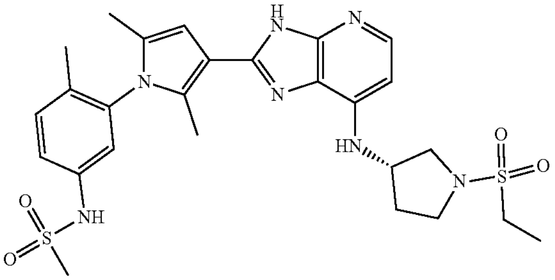 [SMILES: CCS(=O)(=O)N1CC[C@H](Nc2ccnc3[nH]c(-c4cc(C)n(-c5cc(NS(C)(=O)=O)ccc5C)c4C)nc23)C1]

$^1$H NMR (300 MHZ, DMSO-$d_6$) δ 1.19 (t, J=7.26, 3H), 1.96 (m, 8H), 2.28 (br. s., 1H), 2.33 (s, 3H), 3.03 (s, 3H), 3.11 (m, 1H), 3.25 (m, 1H), 3.49 (m, 1H), 3.67 (m, 3H), 4.83 (br. s., 1H), 6.34 (d, J=5.4, 1H), 6.49 (d, J=6.98, 1H), 6.59 (s, 1H), 7.03 (s, 1H), 7.27 (d, J=8.29, 1H), 7.43 (d, J=8.38, 1H), 7.77 (d, J=5.22 Hz, 1H), 9.92 (br. s., 1H), 12.46 (br. s., 1H).

Example 51: N-(3-(3-(6-chloro-7-(((S)-1-(ethylsulfonyl) pyrrolidine-3-yl)amino)-3H-imidazo[4,5-b]pyridine-2-yl)-2,5-dimethyl-1H-pyrrol-1-yl)-4-methylphenyl) methanesulfonamide

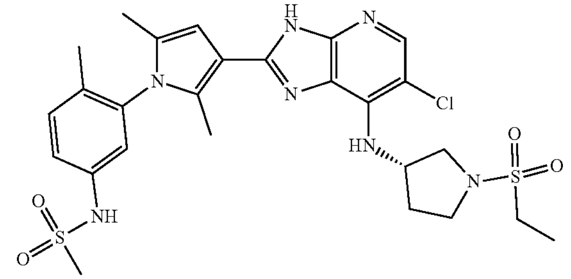 [SMILES: CCS(=O)(=O)N1CC[C@H](Nc2c(Cl)cnc3[nH]c(-c4cc(C)n(-c5cc(NS(C)(=O)=O)ccc5C)c4C)nc23)C1]

$^1$H NMR (300 MHZ, DMSO-$d_6$) δ 1.88 (s, 3H), 1.9 (s, 3H), 2.3 (s, 3H), 3.02 (s, 3H), 5.62 (m, 1H), 6.04 (d, J=7.40, 1H), 6.61 (s, 1H), 7.02 (s, 1H), 7.26 (d, J=8.60, 1H), 7.42 (d, J=8.80 1H), 7.88 (s, 1H), 9.91 (s, 1H), 12.70 (s, 1H).

Example 52: (S)-6-chloro-2-(2,5-dimethyl-1-(4-(2-morpholinoethoxy)phenyl)-1H-pyrrol-3-yl)-N-(1-(ethylsulfonyl) pyrrolidine-3-yl)-1H-imidazo[4,5-b] pyridine-7-amine

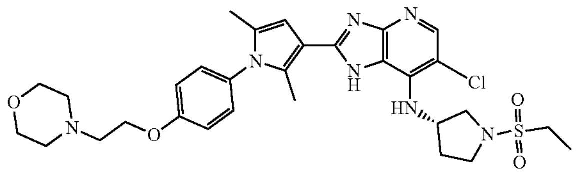 [SMILES: CCS(=O)(=O)N1CC[C@H](Nc2c(Cl)cnc3nc(-c4cc(C)n(-c5ccc(OCCN6CCOCC6)cc5)c4C)[nH]c23)C1]

$^1$H NMR (300 MHZ, DMSO-$d_6$) δ 1.19 (t, J=7.36, 3H), 1.98 (s, 3H), 2.14 (m, 1H), 2.31 (m, 1H), 2.38 (s, 3H), 2.73 (t, J=5.70, 2H), 3.09 (q, J=7.50, 2H), 3.30 (m, 1H), 3.33 (m, 4H), 3.36 (m, 1H), 3.54 (m, 5H), 3.69 (m, 1H), 4.16 (t, J=5.70, 2H), 5.62 (m, 1H), 6.05 (d, J=8.30, 1H), 6.55 (s, 1H), 7.10 (d, J=9.03, 2H), 7.25 (d, J=8.94, 2H), 7.88 (s, 1H), 12.67 (s, 1H).

Example 53: (S)-2-(2,5-dimethyl-1-(4-(2-morpholinoethoxy)phenyl)-1H-pyrrol-3-yl)-N-(1-(ethylsulfonyl) pyrrolidine-3-yl)-1H-imidazo[4,5-b]pyridine-7-amine

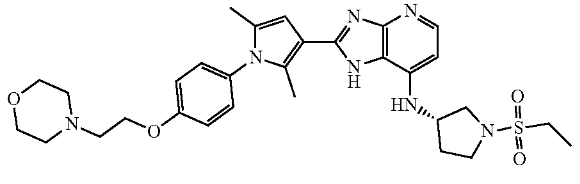 [SMILES: CCS(=O)(=O)N1CC[C@H](Nc2ccnc3nc(-c4cc(C)n(-c5ccc(OCCN6CCOCC6)cc5)c4C)[nH]c23)C1]

$^1$H NMR (300 MHz, DMSO-$d_6$) δ 1.19 (t, J=7.40, 3H), 1.98 (s, 4H), 2.28 (br. s, 1H), 2.41 (s, 3H), 2.73 (t, J=5.80, 2H), 3.08 (m, 2H), 3.59 (m, 6H), 4.15 (m, 2H), 4.84 (s, 1H), 6.33 (d, J=5.8 Hz, 1H), 6.49 (m, 2H), 7.09 (d, J=8.5 Hz, 2H), 7.24 (d, J=9 Hz, 2H), 7.76 (d, J=5.3 Hz, 1H), 12.39 (s, 1H).

Example 54: (S)-(3-(3-(6-chloro-7-((1-(ethylsulfonyl) pyrrolidine-3-yl)amino)-1H-imidazo[4,5-b] pyridine-2-yl)-2,5-dimethyl-1H-pyrrol-1-yl)phenyl) (morpholino) methanone

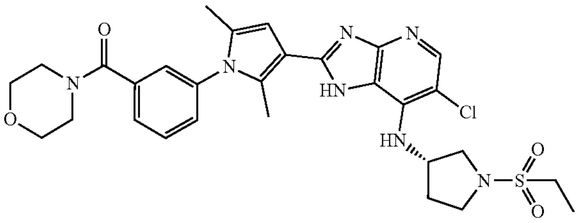 [SMILES: CCS(=O)(=O)N1CC[C@H](Nc2c(Cl)cnc3nc(-c4cc(C)n(-c5cccc(C(=O)N6CCOCC6)c5)c4C)[nH]c23)C1]

$^1$H NMR (300 MHZ, DMSO-$d_6$) δ 1.19 (t, J=7.5, 3H), 2.03 (s, 3H), 2.15 (m, 1H), 2.5 (m, 4H), 3.33 (m, 1H), 2.42 (s, 3H), 3.08 (m, 2H), 3.68 (m, 8H), 6.06 (d, J=8.0, 1H), 6.61 (s, 1H), 7.41 (s, 1H), 7.46 (d, J=8.5, 1H), 7.54 (d, J=8.4, 1H), 7.65 (m, 1H), 7.89 (s, 1H), 12.72 (s, 1H).

Hereinafter, the compound of Example 55 was synthesized according to the representative synthesis method 2.

Example 55: (S)-(3-(3-(7-((1-(ethylsulfonyl) pyrrolidine-3-yl)amino)-3H-imidazo[4,5-b]pyridine-2-yl)-2,5-dimethyl-1H-pyrrol-1-yl)phenyl) (morpholino) methanone

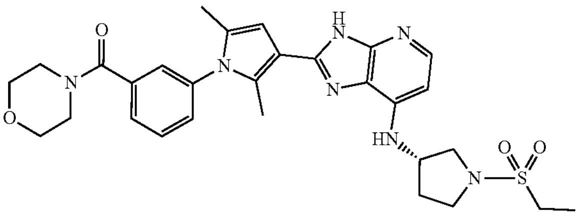 [SMILES: CCS(=O)(=O)N1CC[C@H](Nc2ccnc3[nH]c(-c4cc(C)n(-c5cccc(C(=O)N6CCOCC6)c5)c4C)nc23)C1]

$^1$H NMR (300 MHZ, DMSO-$d_6$) δ 1.19 (t, J=7.5, 3H), 2.03 (m, 4H), 2.29 (m, 1H), 2.46 (s, 3H), 3.09 (m, 2H), 2.5 (m, 4H), 3.68 (m, 8H), 4.85 (br. s, 1H), 6.35 (s, 1H), 6.52 (s, 1H), 6.58 (s, 1H), 7.48 (m, 3H), 7.66 (m, 1H), 7.18 (br. s, 1H), 12.43 (br. s, 1H).

Hereinafter, the compounds of Examples 56 to 87 were synthesized according to the representative synthesis method 1.

Example 56: (S)-3-(3-(6-bromo-7-((1-(ethylsulfonyl) pyrrolidine-3-yl)amino)-1H-imidazo[4,5-b] pyridine-2-yl)-2,5-dimethyl-1H-pyrrol-1-yl)-N-(2-(diethylamino)ethyl)benzamide

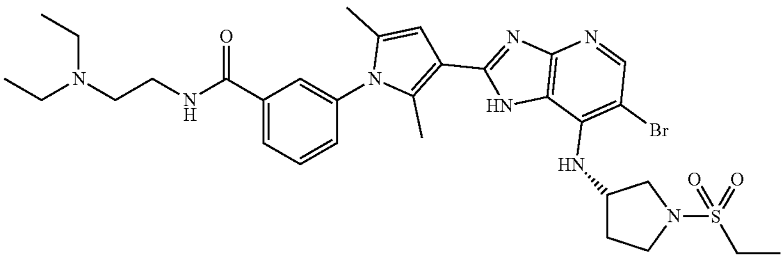

$^1$H NMR (300 MHZ, CHLOROFORM-d) δ 1.27 (d, J=7.2, 6H), 1.38 (t, J=7.4, 7.4, 4H), 2.09 (m, 4H), 2.49 (m, 4H), 3.03 (m, 7H), 3.56 (m, 3H), 3.83 (m, 3H), 5.02 (d, J=7.9, 1H), 5.74 (br. s, 1H), 6.42 (s, 1H), 7.26 (m, 1H), 7.4 (d, J=7.5, 1H), 7.63 (t, J=7.8, 7.8, 1H), 7.92 (br. s, 1H), 8.13 (s, 2H), 11.39 (s, 1H).

Example 57: (S)-4-(3-(6-bromo-7-((1-(ethylsulfonyl) pyrrolidine-3-yl)amino)-1H-imidazo[4,5-b] pyridine-2-yl)-2,5-dimethyl-1H-pyrrol-1-yl)-N-(2-(diethylamino)ethyl)benzamide

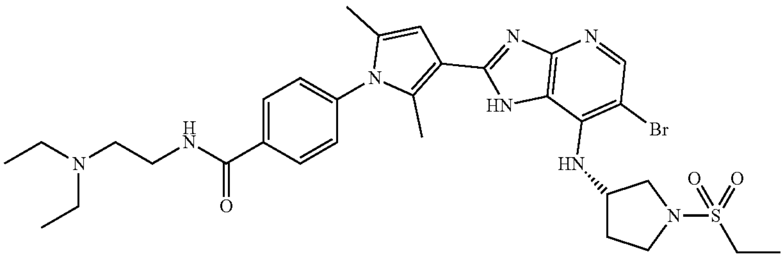

$^1$H NMR (300 MHz, CHLOROFORM-d) δ 1.37 (m, 10H), 2.1 (s, 4H), 2.43 (m, 4H), 3.02 (m, 5H), 3.1 (br. s, 2H), 3.51 (m, 2H), 3.65 (m, 1H), 3.81 (m, 3H), 5.03 (d, J=8.2, 1H), 5.74 (br. s, 1H), 6.43 (s, 1H), 7.34 (d, J=8.2, 2H), 8.16 (m, 3H), 8.53 (br. s, 1H), 11.69 (br. s, 1H).

Example 58: (S)-3-(3-(6-bromo-7-((1-(ethylsulfonyl) pyrrolidine-3-yl)amino)-3H-imidazo[4,5-b] pyridine-2-yl)-2,5-dimethyl-1H-pyrrol-1-yl)benzoic acid

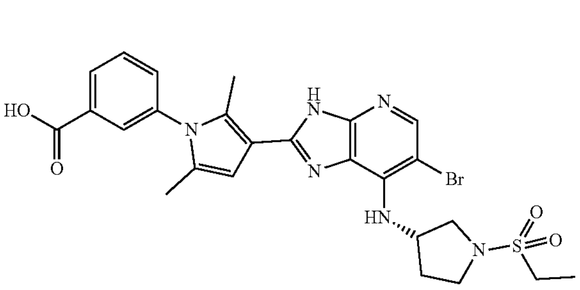

$^1$H NMR (300 MHZ, DMSO-$d_6$) δ 1.18 (t, J=7.5, 7.5, 3H), 2 (br. s, 3H), 2.11 (br. s, 1H), 2.31 (br. s, 1H), 2.39 (br. s, 3H), 3.1 (m, 3H), 3.3 (m, 2H), 3.5 (m, 1H), 3.67 (m, 1H), 5.63 (m, 1H), 5.78 (d, J=7.6, 1H), 6.61 (s, 1H), 7.57 (br. s, 1H), 7.65 (m, 1H), 7.77 (s, 1H), 7.98 (s, 1H), 8.05 (d, J=8.6, 1H), 12.75 (br. s, 1H).

Example 59: (S)-4-(3-(6-bromo-7-((1-(ethylsulfonyl) pyrrolidine-3-yl)amino)-3H-imidazo[4,5-b] pyridine-2-yl)-2,5-dimethyl-1H-pyrrol-1-yl)benzoic acid

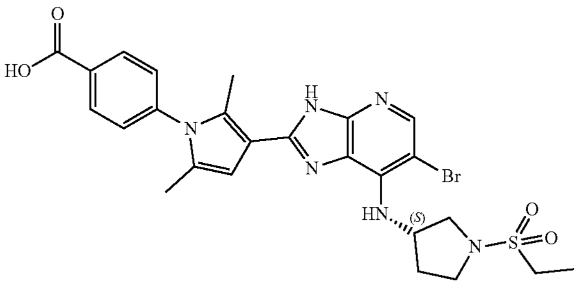

$^1$H NMR (300 MHZ, DMSO-$d_6$) δ 1.19 (t, J=7.3, 7.3, 3H), 2.03 (s, 3H), 2.13 (m, 1H), 2.32 (m, 1H), 2.42 (s, 3H), 3.1 (m, 3H), 3.48 (m, 2H), 3.52 (m, 1H), 3.69 (m, 1H), 5.64 (m,

1H), 5.78 (d, J=8.4, 1H), 6.62 (s, 1H), 7.47 (d, J=8.3, 2H), 7.98 (s, 1H), 8.1 (d, J=8.4, 2H), 12.75 (s, 1H).

Example 60: (S)-3-(3-(6-bromo-7-((1-(ethylsulfonyl) pyrrolidine-3-yl)amino)-3H-imidazo[4,5-b] pyridine-2-yl)-2,5-dimethyl-1H-pyrrol-1-yl)-N-((dimethylamino)methyl)benzamide

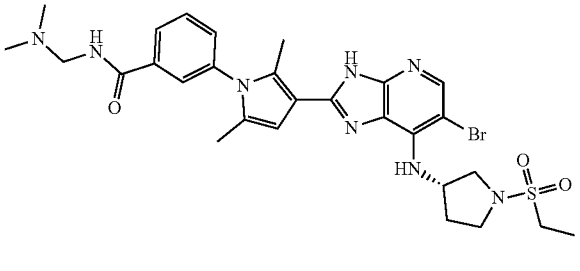 [SMILES: CCS(=O)(=O)N1CC[C@H](Nc2c(Br)cnc3[nH]c(-c4cc(C)n(-c5cccc(C(=O)NCN(C)C)c5)c4C)nc23)C1]

$^1$H NMR (300 MHZ, CHLOROFORM-d) δ 1.37 (t, J=7.4, 7.4; 3H), 2.09 (s, 4H), 2.38 (m, 6H), 2.44 (s, 3H), 2.49 (m, 1H), 2.68 (d, J=4.8; 2H), 3.03 (dt, J=11.5, 7.3, 7.3, 2H), 3.56 (m, 5H), 3.84 (dd, J=10.7,5.7; 1H), 5.02 (d, J=8.1; 1H), 5.73 (m, 1H), 6.41 (s, 1H), 7.26 (m, 1H), 7.39 (d, J=7.5; 1H), 7.6 (t, J=7.8, 7.8; 1H), 7.77 (s, 1H), 7.93 (d, J=7.5; 1H), 8.14 (s, 1H), 11.65 (br. s, 1H).

Example 61: (S)-3-(3-(6-bromo-7-((1-(ethylsulfonyl) pyrrolidine-3-yl)amino)-3H-imidazo[4,5-b] pyridine-2-yl)-2,5-dimethyl-1H-pyrrol-1-yl)-N-(2-(dimethylamino)ethyl)-N-methylbenzamide

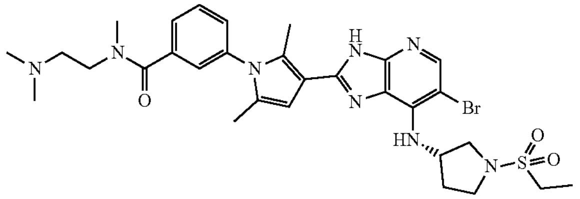

$^1$H NMR (300 MHZ, CHLOROFORM-d) δ 1.37 (t, J=7.4, 7.4, 3H), 1.47 (br. s, 2H), 1.55 (m, 3H), 2.12 (s, 4H), 2.47 (m, 4H), 2.51 (br. s, 3H), 3.03 (m, 2H), 3.11 (s, 3H), 3.56 (m, 4H), 3.84 (m, 2H), 5.03 (d, J=8.2, 1H), 5.74 (s, 1H), 6.42 (s, 1H), 7.33 (m, 2H), 7.59 (br. s, 2H), 8.15 (s, 1H), 11.82 (s, 1H).

Example 62: (S)-4-(3-(6-bromo-7-((1-(ethylsulfonyl) pyrrolidine-3-yl)amino)-3H-imidazo[4,5-b] pyridine-2-yl)-2,5-dimethyl-1H-pyrrol-1-yl)-N-(2-(dimethylamino)ethyl)benzamide

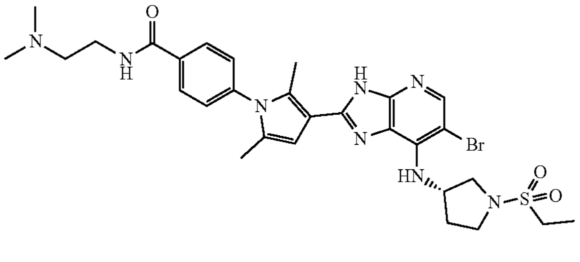 [SMILES: CCS(=O)(=O)N1CC[C@H](Nc2c(Br)cnc3[nH]c(-c4cc(C)n(-c5ccc(C(=O)NCCN(C)C)cc5)c4C)nc23)C1]

$^1$H NMR (300 MHZ, CHLOROFORM-d) δ 1.37 (t, J=7.5, 7.5, 3H), 2.11 (m, 4H), 2.34 (s, 6H), 2.48 (m, 4H), 2.61 (t, J=5.7, 5.7, 2H), 3.03 (m, 2H), 3.55 (m, 5H), 3.85 (dd, J=10.5, 5.6, 1H), 5.04 (d, J=7.7, 1H), 5.73 (br. s, 1H), 6.46 (s, 1H), 7.1 (br. s, 1H), 7.34 (d, J=8.2, 2H), 7.98 (d, J=8.2, 2H), 8.17 (s, 1H), 12.37 (br. s, 1H).

Example 63: (S)-4-(3-(6-bromo-7-((1-(ethylsulfonyl) pyrrolidine-3-yl)amino)-3H-imidazo[4,5-b] pyridine-2-yl)-2,5-dimethyl-1H-pyrrol-1-yl)-N-(2-(dimethylamino)ethyl)-N-methylbenzamide

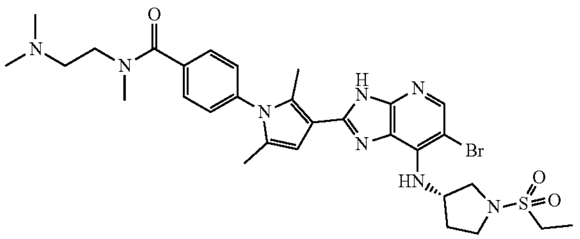 [SMILES: CCS(=O)(=O)N1CC[C@H](Nc2c(Br)cnc3[nH]c(-c4cc(C)n(-c5ccc(C(=O)N(C)CCN(C)C)cc5)c4C)nc23)C1]

$^1$H NMR (300 MHZ, CHLOROFORM-d) δ 1.37 (t, J=7.4, 7.4; 3H), 2.12 (s, 7H), 2.46 (m, 8H), 2.67 (br. s; 1H), 3.03 (m, 5H), 3.57 (m, 5H), 3.85 (dd, J=10.6, 5.7, 1H), 5.05 (d, J=7.9, 1H), 5.74 (m, 1H), 6.48 (s, 1H), 7.32 (m, J=8.0, 2H), 7.6 (m, J=7.9, 2H), 8.17 (s, 1H), 12.76 (br. s, 1H).

Example 64: (S)—N-(3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)phenyl)-2-(dimethylamino) acetamide

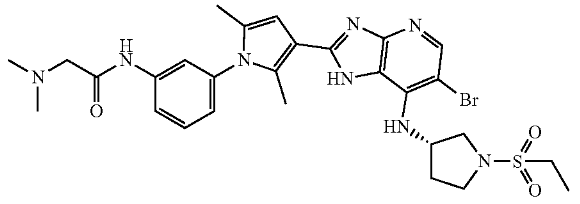 [SMILES: CCS(=O)(=O)N1CC[C@H](Nc2c(Br)cnc3nc(-c4cc(C)n(-c5cccc(NC(=O)CN(C)C)c5)c4C)[nH]c23)C1]

$^1$H NMR (300 MHZ, CHLOROFORM-d) & 1.37 (t, J=7.5, 3H), 2.10 (m, 1H), 2.46 (m, 12H), 3.03 (m, 2H), 3.11 (s, 2H), 3.54 (m, 4H), 3.85 (m, 1H), 5.02 (d, J=7.7, 1H), 5.75 (m, 1H), 6.41 (s, 1H), 7.01 (d, J=8.0, 1H), 7.47 (t, J=7.9, 1H), 7.64 (m, 2H), 8.16 (s, 1H), 9.30 (s, 1H), 12.11 (br. s., 1H).

Example 65: (S)—N-(3-(3-(6-bromo-7-(1-(ethylsulfonyl) pyrolidine-3-yl)amino)-1H-imidazo[4,5-b] pyridine-2-yl)-2,5-dimethyl-1H-pyrrol-1-yl)phenyl)-2-(4-methylpiperazine-1-yl) acetamide

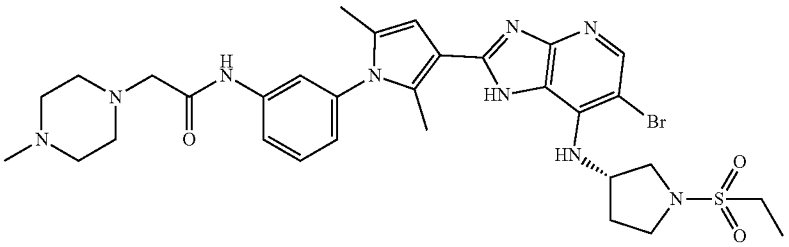 [SMILES: CCS(=O)(=O)N1CC[C@H](Nc2c(Br)cnc3nc(-c4cc(C)n(-c5cccc(NC(=O)CN6CCN(C)CC6)c5)c4C)[nH]c23)C1]

$^1$H NMR (300 MHz, DMSO-$d_6$) δ 1.19 (t, J=7.5, 3H), 2.02 (s, 3H), 2.13 (m, 1H), 2.31 (m, 1H), 2.40 (m, 6H), 2.64 (m, 8H), 3.09 (q, J=8.0, 2H), 3.20 (s, 2H), 3.27 (m, 1H), 3.36 (m, 1H), 3.51 (m, 1H), 3.67 (m, 1H), 5.64 (m, 1H), 5.78 (d, J=8.0, 1H), 6.59 (s, 1H), 7.06 (d, J=8.0, 1H), 7.50 (t, J=8.1, 1H), 7.71 (m, 2H), 7.98 (s, 1H), 9.95 (s, 1H), 12.72 (br. s., 1H).

Example 66: (S)—N-(3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)phenyl)-2-morpholinoacetamide

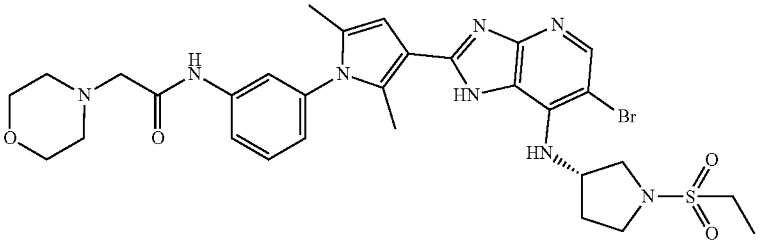 [SMILES: CCS(=O)(=O)N1CC[C@H](Nc2c(Br)cnc3nc(-c4cc(C)n(-c5cccc(NC(=O)CN6CCOCC6)c5)c4C)[nH]c23)C1]

$^1$H NMR (300 MHZ, CHLOROFORM-d) δ 1.38 (t, J=7.5, 3H), 2.09 (m, 1H), 2.16 (s, 3H), 2.48 (m, 4H), 2.67 (m, 4H), 3.04 (m, 2H), 3.20 (s, 2H), 3.58 (m, 3H), 3.81 (m, 4H), 3.89 (m, 1H), 5.04 (d, J=7.4, 1H), 5.76 (m, 1H), 6.45 (s, 1H), 7.05 (d, J=7.5, 1H), 7.50 (t, J=7.8, 1 H), 7.64 (m, 2H), 8.19 (m, 1H), 9.24 (m, 1H), 12.38 (m, 1H).

Example 67: (S)-(4-(3-(6-bromo-7-((1-(ethylsulfonyl) pyrrolidine-3-yl)amino)-1H-imidazo[4,5-b] pyridine-2-yl)-2,5-dimethyl-1H-pyrrol-1-yl)phenyl) (4-methylpiperazine-1-yl) methanone

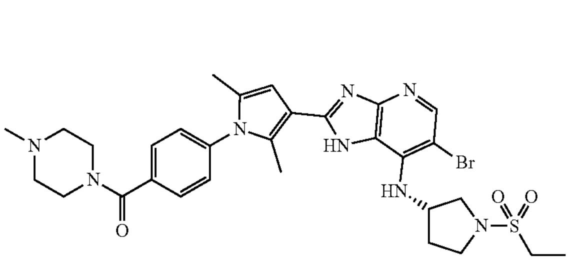

$^1$H NMR (300 MHz, CHLOROFORM-d) δ 1.39 (t, J=7.3, 7.3, 2.14 (s, 4H), 2.37 (s, 3H), 2.48 (br. s, 8H), 3.05 (m, 2H), 3.58 (m, 5H), 3.89 (m, 3H), 5.07 (m, 1H), 5.74 (br. s, 1H), 6.46 (s, 1H), 7.34 (m, 2H), 7.6 (d, J=7.5, 2H), 8.18 (s, 1H), 12.14 (m, 1H).

Example 68: (S)-(3-(3-(6-bromo-7-(1-(ethylsulfonyl) pyrolidine-3-yl)amino)-1H-imidazo[4,5-b]pyridine-2-yl)-2,5-dimethyl-1H-pyrrol-1-yl)phenyl) (4-methylpiperazine-1-yl) methanone

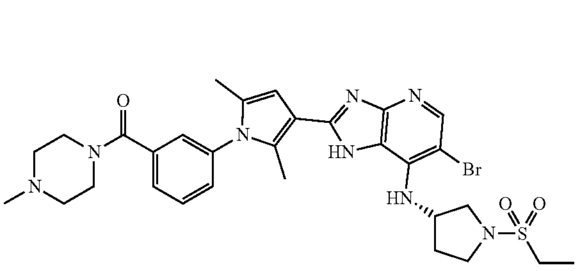

$^1$H NMR (300 MHZ, CHLOROFORM-d) δ 1.38 (t, J=7.4, 7.4, 3H), 2.14 (s, 4H), 2.35 (s, 3H), 2.48 (m, 8H), 3.05 (m, 2H), 3.57 (m, 5H), 3.88 (m, 3H), 5.06 (d, J=7.5, 1H), 5.75 (br. s, 1H), 6.45 (s, 1H), 7.35 (m, 2H), 7.59 (m, 2H), 8.16 (s, 1H), 12.12 (br. s, 1H).

Example 69: (S)-3-(3-(6-bromo-7-((1-(ethylsulfonyl) pyrrolidine-3-yl)amino)-3H-imidazo[4,5-b] pyridine-2-yl)-2,5-dimethyl-1H-pyrrol-1-yl)-N-(2-morpholinoethyl)benzamide

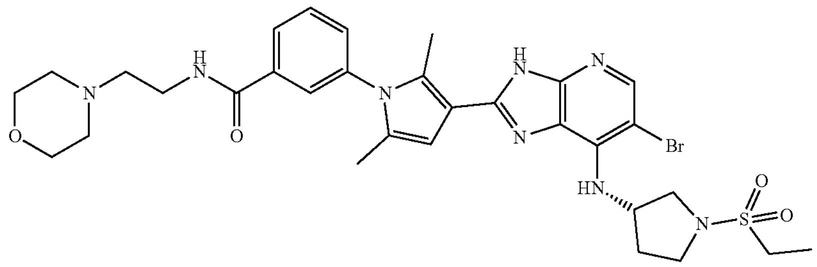

$^1$H NMR (300 MHZ, CHLOROFORM-d) δ 1.37 (t, J=7.0, 7.0, 3H), 2.11 (m, 4H), 2.45 (m, 4H), 2.53 (br. s, 4H), 2.64 (t, J=6.0, 6.0, 2H), 3.02 (m, 2H), 3.47 (dd, J=10.3, 4.1, 1H), 3.63 (m, 4H), 3.74 (t, J=4.3, 4.3, 4H), 3.86 (dd, J=10.6, 5.9, 1H), 5.04 (d, J=8, 1H), 5.73 (br. s, 1H), 6.46 (s, 1H), 6.84 (br. s, 1H), 7.43 (d, J=7.8, 1H), 7.63 (t, J=7.8, 7.8, 1H), 7.74 (s, 1H), 7.86 (d, J=7.7, 1H), 8.17 (s, 1H), 12.18 (br. s, 1H).

Example 70: (S)-4-(3-(6-bromo-7-((1-(ethylsulfonyl) pyrrolidine-3-yl)amino)-3H-imidazo[4,5-b] pyridine-2-yl)-2,5-dimethyl-1H-pyrrol-1-yl)-N-(2-morpholinoethyl)benzamide

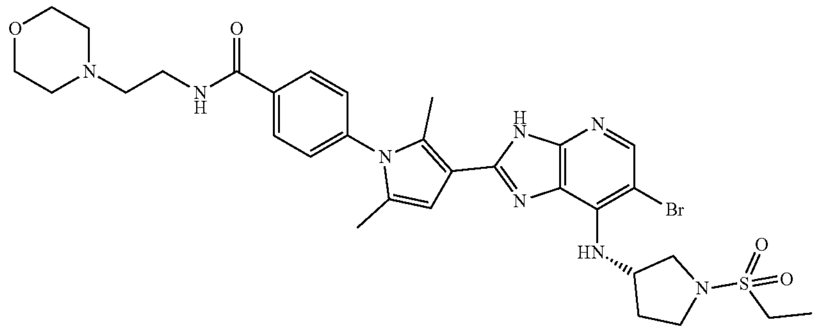

$^1$H NMR (300 MHZ, CHLOROFORM-d) δ 1.37 (t, J=7.5, 7.5, 3H), 2.09 (m, 4H), 2.47 (m, 4H), 2.56 (br. s, 4H), 2.68 (m, 2H), 3.03 (m, 2H), 3.48 (m, 1H), 3.61 (m, 4H), 3.77 (m, 4H), 3.87 (dd, J=10.4, 5.6, 1H), 5.04 (d, J=7.5, 1H), 5.72 (br. s, 1H), 6.46 (s, 1H), 6.9 (br. s, 1H), 7.36 (d, J=7.8, 2H), 7.95 (d, J=7.8, 2H), 8.17 (s, 1H), 12.22 (br. s, 1H).

Example 71: (S)-3-(3-(6-bromo-7-((1-(ethylsulfonyl) pyrrolidine-3-yl)amino)-3H-imidazo[4,5-b] pyridine-2-yl)-2,5-dimethyl-1H-pyrrol-1-yl)-N-(2-(4-methylpiperazine-1-yl)ethyl)benzamide

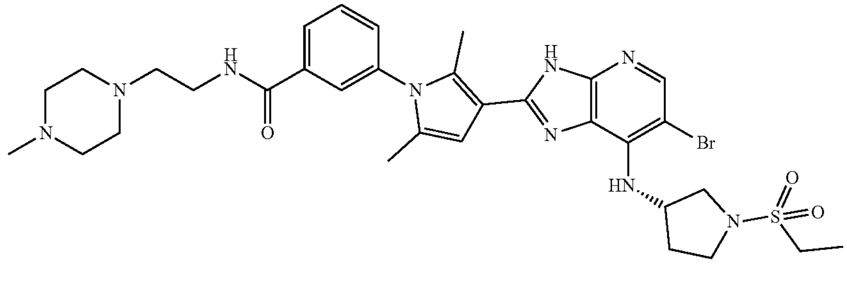

$^1$H NMR (300 MHz, CHLOROFORM-d) δ 1.37 (t, J=7.4, 7.4, 3H), 2.1 (m, 4H), 2.36 (s, 3H), 2.46 (s, 4H), 2.6 (br. s, 4H), 2.72 (m, 6H), 3.02 (m, 2H), 3.48 (m, 1H), 3.6 (m, 4H), 3.86 (dd, J=10.8, 6.1, 1H), 5.03 (d, J=7.4, 1H) 5.74 (br. s, 1H), 6.44 (s, 1H), 7.13 (br. s, 1H), 7.41 (d, J=7.8, 1H), 7.62 (t, J=7.7, 7.7, 1H), 7.77 (s, 1H), 7.91 (d, J=7.2, 1H), 8.16 (s, 1H), 11.92 (s, 1H).

Example 72: (S)-4-(3-(6-bromo-7-((1-(ethylsulfonyl) pyrrolidine-3-yl)amino)-3H-imidazo[4,5-b] pyridine-2-yl)-2,5-dimethyl-1H-pyrrol-1-yl)-N-(2-(4-methylpiperazine-1-yl)ethyl)benzamide

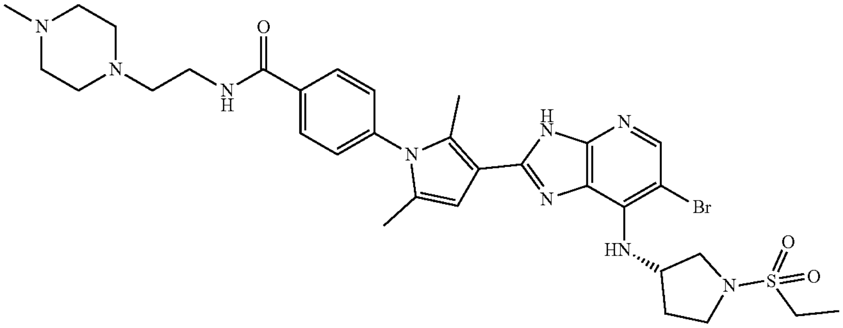

$^1$H NMR (300 MHZ, CHLOROFORM-d) δ 1.37 (t, J=7.3, 7.3, 3H), 2.14 (s, 4H), 2.33 (s, 3H), 2.48 (m, 8H), 2.63 (m, 6H), 3.04 (m, 2H), 3.5 (m, 1H), 3.61 (m, 4H), 3.87 (m, 1H), 5.07 (d, J=7.4, 1H) 5.74 (br. s, 1H), 6.48 (s, 1H), 6.96 (br. s, 1H), 7.37 (d, J=7.8, 2H), 7.96 (d, J=7.7, 2H), 8.18 (s, 1H), 12.39 (br. s, 1H).

Example 73: N-(4-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-3-methylphenyl)-2-(dimethylamino) acetamide

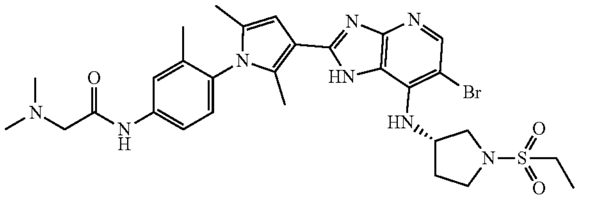 [SMILES: CCS(=O)(=O)N1CC[C@H](Nc2c(Br)cnc3nc(-c4cc(C)n(-c5ccc(NC(=O)CN(C)C)cc5C)c4C)[nH]c23)C1]

$^1$H NMR (300 MHz, CHLOROFORM-d) δ 1.36 (t, J=7.4, 3H), 2.02 (s, 6H), 2.10 (m, 1H), 2.36 (s, 3H), 2.42 (s, 6H), 2.48 (m, 1H), 3.02 (m, 2H), 3.13 (s, 2H), 3.55 (m, 3H), 3.84 (m, 1H), 5.01 (d, J=7.7, 1H), 5.76 (m, 1H), 6.44 (s, 1H), 7.16 (d, J=8.4, 1H), 7.52 (m, 2H), 8.16 (s, 1H), 9.25 (s, 1H), 12.05 (br. s, 1H).

Example 74: N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-4-methylphenyl)-2-(dimethylamino) acetamide

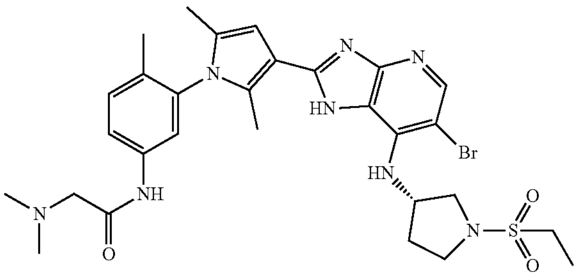 [SMILES: CCS(=O)(=O)N1CC[C@H](Nc2c(Br)cnc3nc(-c4cc(C)n(-c5cc(NC(=O)CN(C)C)ccc5C)c4C)[nH]c23)C1]

$^1$H NMR (300 MHz, DMSO-$d_6$) δ 1.18 (t, J=7.3, 3H), 1.88 (s, 3H), 1.91 (s, 3H), 2.10 (m, 1H), 2.27 (s, 6H), 2.29 (s, 3H), 2.33 (m, 1H), 3.08 (m, 4H), 3.29 (m, 1H), 3.35 (m, 1H), 3.48 (m, 1H), 3.68 (m, 1H), 5.63 (m, 1H), 5.75 (m, 1H), 6.61 (s, 1H), 7.37 (d, J=8.1, 1H), 7.65 (m, 2H), 7.97 (s, 1H), 9.88 (s, 1H), 12.71 (s, 1H).

Example 75: N-(4-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-3-methylphenyl)-2-(4-methylpiperazine-1-yl) acetamide

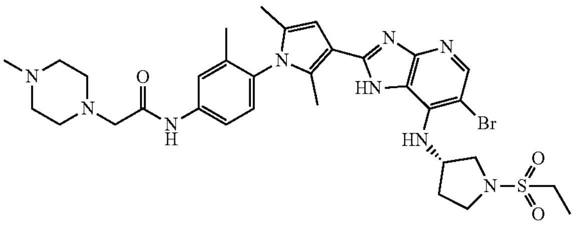 [SMILES: CCS(=O)(=O)N1CC[C@H](Nc2c(Br)cnc3nc(-c4cc(C)n(-c5ccc(NC(=O)CN6CCN(C)CC6)cc5C)c4C)[nH]c23)C1]

$^1$H NMR (300 MHz, DMSO-$d_6$) δ 1.18 (t, J=7.3, 3H), 1.89 (m, 6H), 2.10 (m, 1H), 2.18 (s, 3H), 2.29 (s, 3H), 2.38 (m, 5H), 2.53 (m, 4H), 3.08 (q, J=7.2, 2H), 3.14 (s, 2H), 3.28 (m, 1H), 3.30 (m, 1H), 3.49 (m, 1H), 3.68 (m, 1H), 5.65 (m, 1H), 5.76 (d, J=7.5, 1H), 6.60 (s, 1H), 7.18 (d, J=8.1, 1H), 7.68 (m, 2H), 7.97 (s, 1H), 9.85 (s, 1H), 12.70 (s, 1H).

Example 76: N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-4-methylphenyl)-2-(4-methylpiperazine-1-yl) acetamide

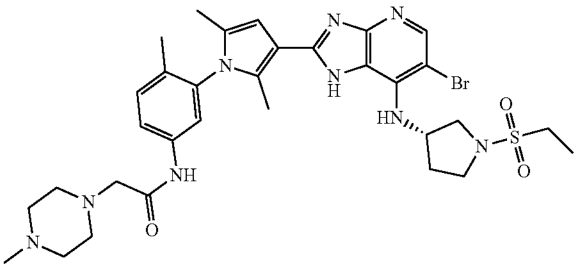 [SMILES: CCS(=O)(=O)N1CC[C@H](Nc2c(Br)cnc3nc(-c4cc(C)n(-c5cc(NC(=O)CN6CCN(C)CC6)ccc5C)c4C)[nH]c23)C1]

$^1$H NMR (300 MHz, DMSO-$d_6$) δ 1.18 (t, J=7.3, 3H), 1.88 (s, 3H), 1.91 (s, 3H), 2.13 (m, 1H), 2.29 (s, 3H), 2.37 (m, 4H), 2.62 (m, 8H), 3.08 (q, J=7.2, 2H), 3.18 (s, 2H), 3.30 (m, 2H), 3.50 (m, 1H), 3.69 (m, 1H), 5.65 (m, 1H), 5.76 (s, 1H), 6.61 (s, 1H), 7.39 (d, J=8.3, 1H), 7.61 (m, 2H), 7.97 (m, 1H), 9.86 (s, 1H), 12.72 (s, 1H).

Example 77: N—(4-(3-(6-bromo-7-(((S)-1-(ethylsulfony) pyrolidine-3-yl)amino)-1H-imidazo[4,5-b] pyridine-2-yl)-2,5-dimethyl-1H-pyrrol-1-yl)-3-methylphenyl)-2-morpholinoacetamide

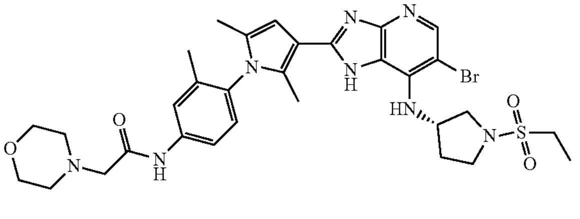 [SMILES: CCS(=O)(=O)N1CC[C@H](Nc2c(Br)cnc3nc(-c4cc(C)n(-c5ccc(NC(=O)CN6CCOCC6)cc5C)c4C)[nH]c23)C1]

$^1$H NMR (300 MHZ, CHLOROFORM-d) δ 1.36 (t, J=7.3, 3H), 2.01 (s, 3H), 2.03 (s, 3H), 2.10 (m, 1H), 2.35 (s, 3H), 2.48 (m, 1H), 2.67 (t, J=4.9, 4H), 3.02 (m, 2H), 3.20 (s, 2H), 3.55 (m, 3H), 3.84 (m, 5H), 5.01 (d, J=8.1, 1H), 5.74 (m, 1H), 6.42 (s, 1H), 7.16 (d, J=8.3, 1 H), 7.59 (m, 2H), 8.15 (s, 1H), 9.19 (s, 1H), 11.70 (br. s., 1H).

Example 78: N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-4-methylphenyl)-2-morpholinoacetamide

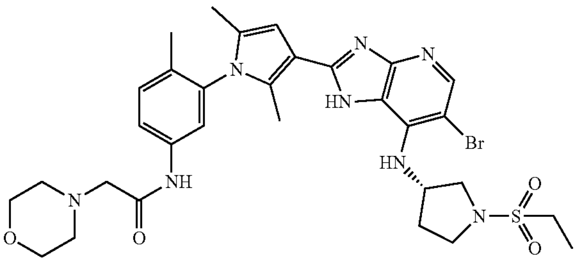 [SMILES: CCS(=O)(=O)N1CC[C@H](Nc2c(Br)cnc3nc(-c4cc(C)n(-c5cc(NC(=O)CN6CCOCC6)ccc5C)c4C)[nH]c23)C1]

$^1$H NMR (300 MHZ, DMSO-$d_6$) δ 1.18 (t, J=7.5, 3H), 1.88 (s, 3H), 1.91 (s, 3H), 2.12 (m, 1H), 2.31 (m, 4H), 2.5 (m, 4H), 3.09 (m, 4H), 3.2 (m, 2H), 3.47 (m, 1H), 3.65 (m, 5H), 5.64 (m, 1H), 5.76 (d, J=8.1, 1H), 6.61 (s, 1H), 7.39 (d, J=8.1, 1H), 7.63 (m, 2H), 7.97 (s, 1H), 9.87 (s, 1H), 12.71 (br. s, 1H).

Example 79: N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-2-methylphenyl)-3-(dimethylamino) propenamide

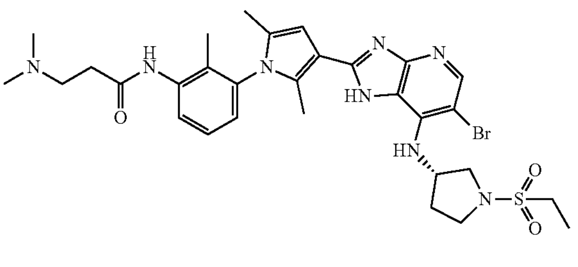 [SMILES: CCS(=O)(=O)N1CC[C@H](Nc2c(Br)cnc3nc(-c4cc(C)n(-c5cccc(NC(=O)CCN(C)C)c5C)c4C)[nH]c23)C1]

$^1$H NMR (300 MHZ, CHLOROFORM-d) δ 1.36 (t, J=7.4, 3H), 2.01 (m, 6H), 2.10 (m, 1H), 2.35 (m, 3H), 2.46 (m, 7H), 2.54 (t, J=5.5, 2H), 2.69 (t, J=5.5, 2H), 3.03 (m, 2H), 3.57 (m, 3H), 3.84 (m, 1H), 5.01 (d, J=7.7, 1H), 5.75 (m, 1H), 6.45 (s, 1H), 7.12 (d, J=8.4, 1H), 7.50 (m, 2H), 8.17 (s, 1H), 11.22 (s, 1H), 12.17 (m, 1H).

Example 80: N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-4-methylphenyl)-3-(dimethylamino) propenamide

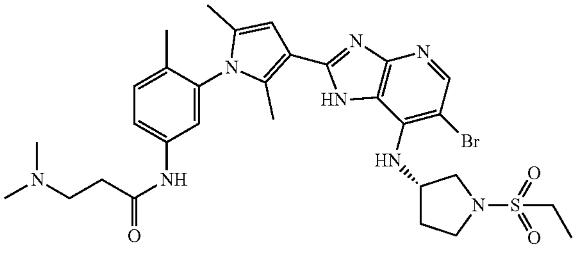 [SMILES: CCS(=O)(=O)N1CC[C@H](Nc2c(Br)cnc3nc(-c4cc(C)n(-c5cc(NC(=O)CCN(C)C)ccc5C)c4C)[nH]c23)C1]

$^{1}$H NMR (300 MHZ, CHLOROFORM-d) δ 1.36 (t, J=7.5, 3H), 1.96 (s, 3H), 2.02 (s, 3H), 2.06 (m, 1H), 2.37 (s, 3H), 2.44 (m, 7H), 2.58 (t, J=5.5, 2H), 2.76 (t, J=5.5, 2H), 3.03 (m, 2H), 3.54 (m, 3H), 3.85 (m, 1H), 5.00 (d, J=7.5, 1H), 5.73 (m, 1H), 6.41 (s, 1H), 7.29 (d, J=8.0, 1H), 7.51 (m, 2H), 8:14 (s, 1H), 10.94 (s, 1H), 11.41 (br. s, 1H).

Example 81: (3-(3-(6-bromo-7-(((S)-1-(ethylsulfonyl) pyrrolidine-3-yl)amino)-1H-imidazo[4,5-b] pyridine-2-yl)-2,5-dimethyl-1H-pyrrol-1-yl)-2-methylphenyl) (4-methylpiperazine-1-yl) methanone

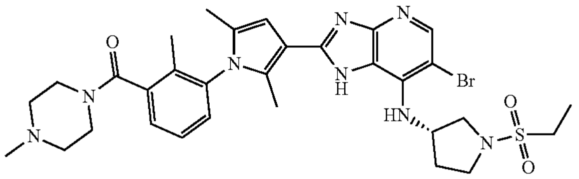 [SMILES: CCS(=O)(=O)N1CC[C@H](Nc2c(Br)cnc3nc(-c4cc(C)n(-c5cccc(C(=O)N6CCN(C)CC6)c5C)c4C)[nH]c23)C1]

$^{1}$H NMR (300 MHZ, CHLOROFORM-d) δ 1.36 (t, J=7.5, 7.5, 3H), 1.97 (s, 3H), 2 (s, 1H), 2.03 (s, 2H), 2.09 (m, 1H), 2.35 (m, 9H), 2.51 (br. s, 3H), 3.02 (m, 2H), 3.28 (br. s, 2H), 3.54 (m, 3H), 3.88 (m, 3H), 5 (d, J=7.8, 1H), 5.74 (br. s, 1H), 6.47 (d, J=6.4, 1H), 7.34 (m, 1H), 7.41 (m, 1H), 8.17 (s, 1H), 12.07 (br. s, 1H).

Example 82:3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-N-(2-(dimethylamino)ethyl)-2-methylbenzamide

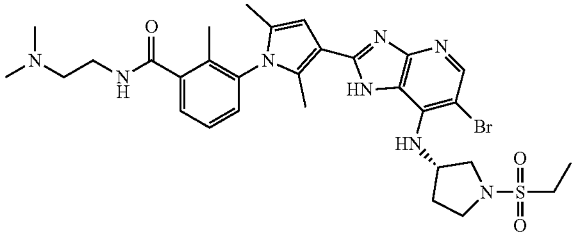 [SMILES: CCS(=O)(=O)N1CC[C@H](Nc2c(Br)cnc3nc(-c4cc(C)n(-c5cccc(C(=O)NCCN(C)C)c5C)c4C)[nH]c23)C1]

$^{1}$H NMR (300 MHZ, CHLOROFORM-d) δ 1.36 (t, J=7.4, 7.4, 3H), 2.01 (s, 3H), 2.1 (m, 4H), 2.34 (s, 5H), 2.36 (s, 3H), 2.47 (dd, J=12.8,7.2, 2H), 2.62 (t, J=5.6, 2H), 3.02 (m, 2H), 3.57 (m, 5H), 3.84 (dd, J=10.5, 6.0, 1H), 5.02 (d, J=8.0, 1H), 5.74 (d, J=11.9, 1H), 6.46 (s, 1H), 6.7 (br. s, 1H), 7.26 (m, 1H) 7.37 (t, J=7.9, 7.9, 1H), 7.54 (d, J=7.7, 1H), 8.16 (s, 1H), 12.1 (br. s, 1H).

Example 83: (3-(3-(6-bromo-7-(((S)-1-(ethylsulfonyl) pyrrolidine-3-yl)amino)-1H-imidazo[4,5-b] pyridine-2-yl)-2,5-dimethyl-1H-pyrrol-1-yl)-2-methylphenyl) (morpholino) methanone

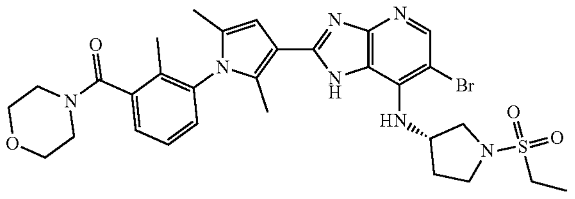 [SMILES: CCS(=O)(=O)N1CC[C@H](Nc2c(Br)cnc3nc(-c4cc(C)n(-c5cccc(C(=O)N6CCOCC6)c5C)c4C)[nH]c23)C1]

$^{1}$H NMR (300 MHZ, CHLOROFORM-d) δ 1.36 (t, J=7.4, 3H), 2.03 (m, 7H), 2.35 (m, 3H), 2.47 (m, 1H), 3.01 (m, 2H), 3.28 (br. s, 2H), 3.55 (m, 5H), 3.79 (br. s, 3H), 3.93 (m, 2H), 5.02 (m, 1H), 5.74 (br. s, 1H), 6.46 (m, 1H), 7.26 (m, 1H), 7.35 (m, 1H), 7.42 (m, 1H), 8.16 (s, 1H), 12.07 (br. s, 1H).

Example 84: N-(3-(3-(6-bromo-7-(((S)-1-(ethylsulfonyl) pyrolidine-3-yl)amino)-1H-imidazo[4,5-b] pyridine-2-yl)-2,5-dimethyl-1H-pyrrol-1-yl)-2-methylphenyl)-2-(dimethylamino) acetamide

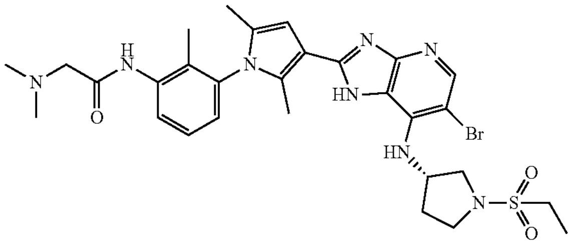 [SMILES: CCS(=O)(=O)N1CC[C@H](Nc2c(Br)cnc3nc(-c4cc(C)n(-c5cccc(NC(=O)CN(C)C)c5C)c4C)[nH]c23)C1]

$^{1}$H NMR (300 MHZ, CHLOROFORM-d) δ 1.37 (t, J=7.3, 3H), 1.92 (s, 3H), 2.03 (s, 3H), 2.11 (m, 1H), 2.37 (s, 3H), 2.46 (m, 7H), 3.03 (m, 2H), 3.17 (s, 2H), 3.56 (m, 3H), 3.85 (m, 1H), 5.03 (d, J=7.9, 1H), 5.76 (m, 1H), 6.50 (s, 1H), 7.02 (m, J=8.0, 1H), 7.38 (t, J=7.5, 1 H), 8.19 (s, 1H), 8.28 (t, J=7.50 Hz, 1H), 9.43 (d, J=8.1, 1H), 12.74 (s, 1H).

Example 85: N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-2-methylphenyl)-2-morpholinoacetamide

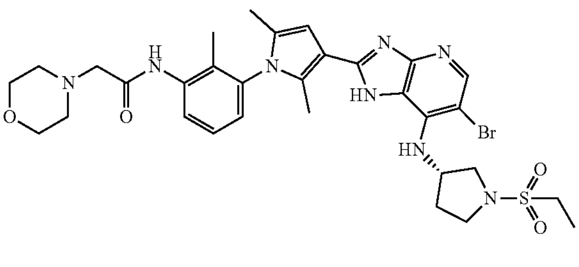 [SMILES: CCS(=O)(=O)N1CC[C@H](Nc2c(Br)cnc3nc(-c4cc(C)n(-c5cccc(NC(=O)CN6CCOCC6)c5C)c4C)[nH]c23)C1]

$^1H$ NMR (300 MHZ, CHLOROFORM-d) δ 1.36 (t, J=7.5, 3H), 1.93 (s, 3H), 2.01 (s, 3H), 2.12 (m, 1H), 2.36 (s, 3H), 2.47 (m, 1H), 2.70 (t, J=5.0, 4H), 3.02 (m, 2H), 3.24 (s, 2H), 3.46 (m, 1H), 3.61 (m, 2H), 3.77 (t, J=5.0, 4H), 3.87 (m, 1H), 5.01 (m, 1H), 5.70 (m, 1H), 6.43 (s, 1H), 7.03 (m, 1H), 7.39 (t, J=7.7, 1H), 8.16 (s, 1H), 8.34 (m, 1H), 9.43 (d, J=6.7, 1H), 11.57 (br. s, 1H).

Example 86: N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-2-methylphenyl)-3-(dimethylamino) propanamide

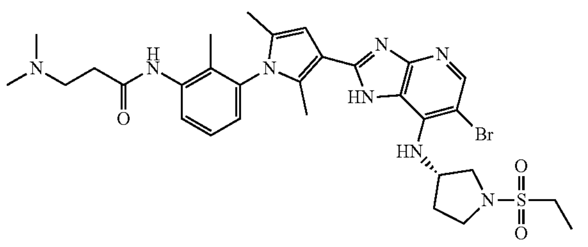 [SMILES: CCS(=O)(=O)N1CC[C@H](Nc2c(Br)cnc3nc(-c4cc(C)n(-c5cccc(NC(=O)CCN(C)C)c5C)c4C)[nH]c23)C1]

$^1H$ NMR (300 MHz, DMSO-$d_6$) δ 1.18 (t, J=7.5, 3H), 1.76 (s, 3H), 1.89 (s, 3H), 2.10 (m, 1H), 2.22 (s, 6H), 2.29 (m, 4H), 2.50 (m, 2H), 2.59 (m, 2H), 3.08 (m, 2H), 3.29 (m, 1H), 3.33 (m, 1H), 3.48 (m, 1H), 3.69 (m, 1H), 5.64 (m, 1H), 5.73 (m, J=1.1, 1H), 6.61 (s, 1H), 7.05 (d, J=8.1, 1H), 7.36 (t, J=8.1, 1H), 7.94 (m, 2H), 10.27 (s, 1H), 12.72 (br. s, 1H).

Example 87: N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-2-methylphenyl)-2-(4-methylpiperazine-1-yl) acetamide

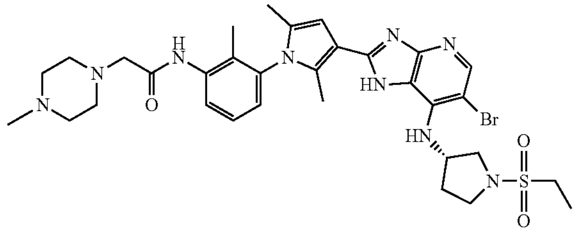 [SMILES: CCS(=O)(=O)N1CC[C@H](Nc2c(Br)cnc3nc(-c4cc(C)n(-c5cccc(NC(=O)CN6CCN(C)CC6)c5C)c4C)[nH]c23)C1]

$^1H$ NMR (300 MHZ, DMSO-$d_6$) δ 1.18 (t, J=7.5, 3H), 1.80 (s, 3H), 1.90 (s, 3H), 2.15 (m, 4H), 2.33 (m, 8H), 2.59 (m, 4H), 3.09 (m, 2H), 3.15 (s, 2H), 3.26 (m, 1H), 3.38 (m, 1H), 3.48 (m, 1H), 3.68 (m, 1H), 5.64 (m, 1H), 5.77 (d, J=7.5, 1H), 6.62 (s, 1H), 7.07 (m, 1H), 7.39 (s, 1H), 7.97 (m, 2H), 9.58 (s, 1H), 12.72 (s, 1H).

Hereinafter, the compounds of Examples 88 to 90 were synthesized according to the representative synthesis method 3.

Example 88: N-(3-(3-(6-bromo-7-((3-sulfamoylphenyl)amino)-1H-imidazo[4,5-b]pyridine-2-yl)-2,5-dimethyl-1H-pyrrol-1-yl)-4-methylphenyl)-2-morpholinoacetamide

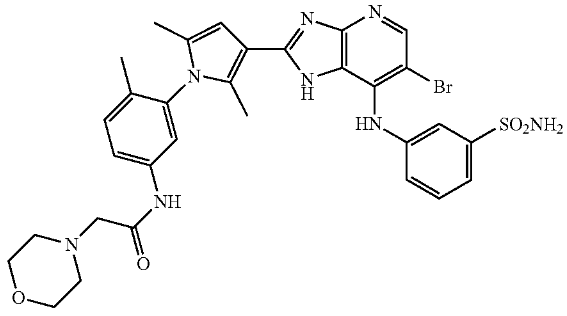 [SMILES: Cc1ccc(NC(=O)CN2CCOCC2)cc1-n1c(C)cc(-c2nc3ncc(Br)c(Nc4cccc(S(N)(=O)=O)c4)c3[nH]2)c1C]

$^1H$ NMR (300 MHZ, DMSO-$d_6$) δ 1.82 (s, 3H), 1.89 (s, 3H), 1.97 (s, 3H), 2.5 (m, 4H), 3.13 (s, 2H), 3.64 (t, J=5.0, 4H), 6.60 (s, 1H), 7.18 (s, 2H), 7.31 (m, 4H), 7.55 (s, 2H), 7.66 (m, 1H), 8.20 (s, 1H), 8.51 (s, 1H), 9.87 (s, 1H), 12.84 (br. s, 2H).

Example 89: N-(3-(3-(6-bromo-7-((3-sulfamoylphenyl)amino)-1H-imidazo[4,5-b]pyridine-2-yl)-2,5-dimethyl-1H-pyrrol-1-yl)-4-methylphenyl)-2-(4-methylpiperazine-1-yl) acetamide

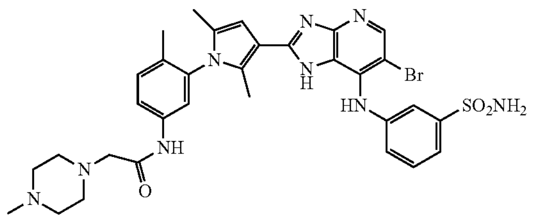 [SMILES: Cc1ccc(NC(=O)CN2CCN(C)CC2)cc1-n1c(C)cc(-c2nc3ncc(Br)c(Nc4cccc(S(N)(=O)=O)c4)c3[nH]2)c1C]

$^1H$ NMR (300 MHZ, CHLOROFORM-d) δ 1.90 (s, 3H), 1.96 (s, 3H), 2.02 (s, 3H), 2.33 (s, 3H), 2.52 (m, 4H), 2.68 (m, 4H), 3.17 (br. s., 2H), 5.49 (br. s, 2H), 6.19 (br. s, 1H), 6.85 (br. s, 1H), 7.40 (m, 7H), 8.16 (s, 1H), 9.23 (s, 1H).

Example 90: N-(3-(3-(6-bromo-7-((3-sulfamoylphenyl)amino)-1H-imidazo[4,5-b]pyridine-2-yl)-2,5-dimethyl-1H-pyrrol-1-yl)-4-methylphenyl)-2-(dimethylamino) acetamide

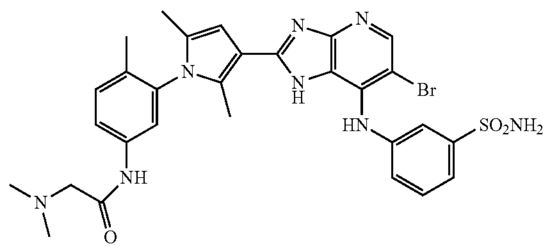 [SMILES: Cc1ccc(NC(=O)CN(C)C)cc1-n1c(C)cc(-c2nc3ncc(Br)c(Nc4cccc(S(N)(=O)=O)c4)c3[nH]2)c1C]

$^1H$ NMR (300 MHZ, DMSO-$d_6$) δ 1.81 (s, 3H), 1.87 (s, 3H), 2 (m, 3H), 2.27 (s, 6H), 3.07 (s, 2H), 6.58 (s, 1H), 7.18

(br. s, 2H), 7.3 (m, 3H), 7.57 (m, 2H), 7.65 (s, 1H), 7.72 (m, 1H), 8.17 (br. s, 1H), 8.53 (br. s, 1H), 9.88 (s, 1H), 12.95 (br. s, 1H).

Hereinafter, the compounds of Examples 91 to 93 were synthesized according to the representative synthesis method 1.

Example 91: (3-(3-(6-bromo-7-(((S)-1-(ethylsulfonyl) pyrrolidine-3-yl)amino)-1H-imidazo[4,5-b] pyridine-2-yl)-2,5-dimethyl-1H-pyrrol-1-yl)-4-methylphenyl) (morpholino) methanone

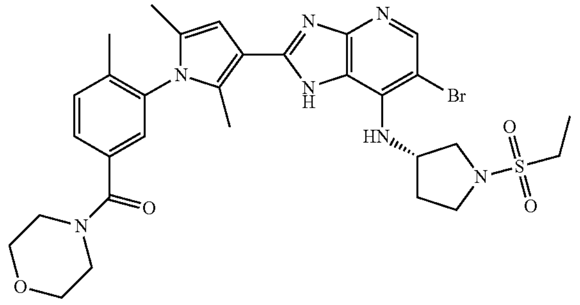 [SMILES: CCS(=O)(=O)N1CC[C@H](Nc2c(Br)cnc3nc(-c4cc(C)n(-c5cc(C(=O)N6CCOCC6)ccc5C)c4C)[nH]c23)C1]

$^1$H NMR (300 MHZ, CHLOROFORM-d) δ 1.38 (t, J=7.5, 3H), 2.06 (m, 7H), 2.39 (s, 3H), 2.48 (m, 1H), 3.03 (m, 2H), 3.67 (m, 12H), 5.05 (d, J=7.5, 1H), 5.76 (m, 1H), 6.53 (s, 1H), 7.26 (m, 1H), 7.49 (m, 2H), 8.20 (s, 1H), 13.00 (s, 1H).

Example 92: (3-(3-(6-bromo-7-(((S)-1-(ethylsulfonyl) pyrrolidine-3-yl)amino)-1H-imidazo[4,5-b] pyridine-2-yl)-2,5-dimethyl-1H-pyrrol-1-yl)-4-methylphenyl) (4-methylpiperazine-1-yl) methanone

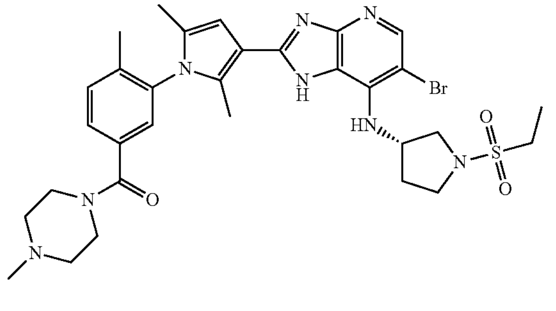 [SMILES: CCS(=O)(=O)N1CC[C@H](Nc2c(Br)cnc3nc(-c4cc(C)n(-c5cc(C(=O)N6CCN(C)CC6)ccc5C)c4C)[nH]c23)C1]

$^1$H NMR (300 MHz, CHLOROFORM-d) δ 1.37 (t, J=7.5, 3H), 2.06 (m, 7H), 2.36 (m, 11H), 3.02 (m, 2H), 3.68 (m, 8H), 5.03 (d, J=7.5, 1H), 5.74 (m, 1H), 6.48 (s, 1H), 7.26 (m, 1H), 7.47 (m, 2H), 8.17 (s, 1H), 12.21 (br. s, 1H).

Example 93:3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-N-(2-(dimethylamino)ethyl)-4-methylbenzamide

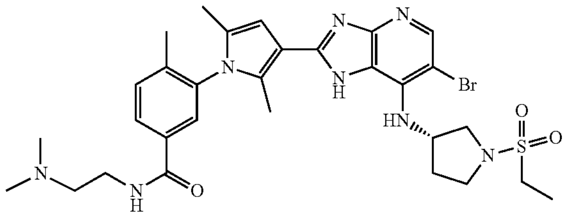 [SMILES: CCS(=O)(=O)N1CC[C@H](Nc2c(Br)cnc3nc(-c4cc(C)n(-c5cc(C(=O)NCCN(C)C)ccc5C)c4C)[nH]c23)C1]

$^1$H NMR (300 MHZ, CHLOROFORM-d) δ 1.36 (t, J=7.5, 3H), 2.02 (s, 3H), 2.07 (s, 3H), 2.31 (m, 10H), 2.47 (m, 1H), 2.54 (m, 2H), 3.03 (m, 2H), 3.55 (m, 5H), 3.84 (m, 1H), 5.03 (d, J=7.5, 1H), 5.75 (m, 1H), 6.49 (s, 1H), 6.88 (br. s., 1H), 7.46 (d, J=8.20 Hz, 1H), 7.65 (d, J=6.1, 1H), 7.84 (t, J=7.26 Hz, 1H), 8.18 (s, 1H), 12.36 (br. s, 1H).

Hereinafter, the compounds of Examples 94 to 96 were synthesized according to the representative synthesis method 3.

Example 94:3-((6-bromo-2-(2,5-dimethyl-1-(2-methyl-5-(morpholine-4-carbonyl)phenyl)-1H-pyrrol-3-yl)-1H-imidazo[4,5-b]pyridine-7-yl)amino) benzenesulfonamide

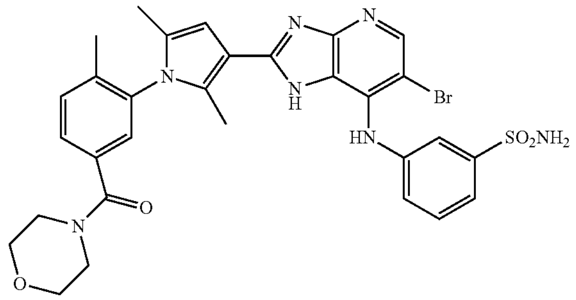 [SMILES: Cc1ccc(C(=O)N2CCOCC2)cc1-n1c(C)cc(-c2nc3ncc(Br)c(Nc4cccc(S(N)(=O)=O)c4)c3[nH]2)c1C]

$^1$H NMR (300 MHZ, CHLOROFORM-d) δ 1.92 (s, 3H), 1.98 (s, 3H), 2.05 (br. s, 3H), 3.70 (m, 8H), 5.62 (br. s, 2H), 6.22 (br. s, 1H), 6.81 (br. s, 1H), 7.17 (br. s, 1H), 7.41 (m, 4H), 7.56 (br. s, 1H), 7.80 (br. s, 1H), 8.11 (br. s, 1H).

Example 95:3-((6-bromo-2-(2,5-dimethyl-1-(2-methyl-5-(4-methylpiperazine-1-carbonyl)phenyl)-1H-pyrrol-3-yl)-1H-imidazo[4,5-b]pyridine-7-yl) amino)benzenesulfonamide

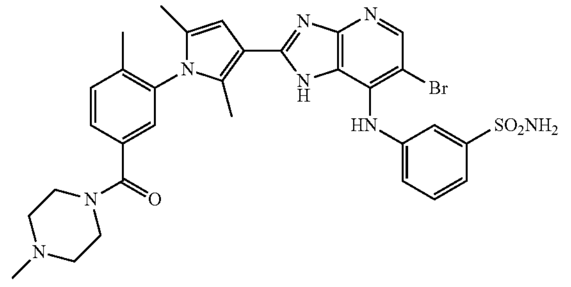 [SMILES: Cc1ccc(C(=O)N2CCN(C)CC2)cc1-n1c(C)cc(-c2nc3ncc(Br)c(Nc4cccc(S(N)(=O)=O)c4)c3[nH]2)c1C]

$^{1}$H NMR (300 MHz, DMSO-$d_6$) δ 1.87 (s, 3H), 1.90 (s, 3H), 2.00 (br. s, 3H), 2.18 (m, 4H), 2.31 (m, 4H), 3.59 (br. s, 3H), 6.60 (br. s, 1H), 7.24 (m, 6H), 7.49 (m, 3H), 8.18 (s, 1H), 8.50 (br. s, 1H), 12.79 (br. s, 1H).

Example 96:3-(3-(6-bromo-7-((3-sulfamoylphenyl) amino)-1H-imidazo[4,5-b]pyridine-2-yl)-2,5-dimethyl-1H-pyrrol-1-yl)-N-(2-(dimethylamino)ethyl)-4-methylbenzamide

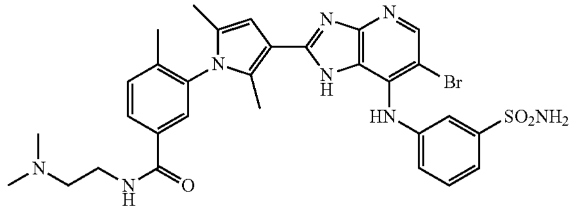 [SMILES: Cc1ccc(C(=O)NCCN(C)C)cc1-n1c(C)cc(-c2nc3ncc(Br)c(Nc4cccc(S(N)(=O)=O)c4)c3[nH]2)c1C]

$^{1}$H NMR (300 MHz, DMSO-$d_6$) δ 1.88 (s, 3H), 1.93 (s, 3H), 2.01 (s, 3H), 2.16 (s, 6H), 2.38 (t, J=7.5, 2H), 3.2 (t, 2H), 6.61 (s, 1H), 7.15 (br. s, 2H), 7.31 (m, 3H), 7.52 (m, 2H), 7.68 (s, 1H), 7.90 (m, 1H), 8.19 (s, 1H), 8.48 (m, 2H), 12.87 (br. s, 1H).

Hereinafter, the compounds of Examples 97 and 98 were synthesized according to the representative synthesis method 1.

Example 97: (4-(3-(6-bromo-7-(((S)-1-(ethylsulfonyl) pyrrolidine-3-yl)amino)-3H-imidazo[4,5-b] pyridine-2-yl)-2,5-dimethyl-1H-pyrrol-1-yl)-3-methylphenyl) (4-methylpiperazine-1-yl) methanone

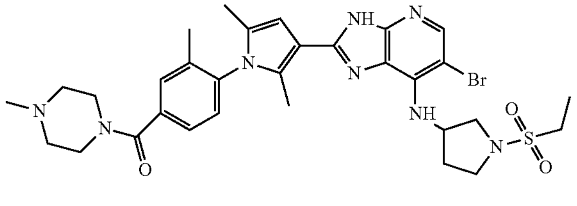 [SMILES: CCS(=O)(=O)N1CCC(Nc2c(Br)cnc3[nH]c(-c4cc(C)n(-c5ccc(C(=O)N6CCN(C)CC6)cc5C)c4C)nc23)C1]

$^{1}$H NMR (300 MHz, CHLOROFORM-d) δ 1.37 (t, J=7.3, 7.3, 3H), 2.01 (s, 3H), 2.05 (s, 3H), 2.36 (s, 7H), 2.47 (m, 6H), 3.03 (m, 2H), 3.55 (m, 5H, 3.85 (m, 3H), 5.01 (d, J=7.3, 1H), 5.73 (m, 1H), 6.53 (s, 1H), 7.22 (br. s, 1H), 7.37 (d, J=10, 1H), 7.46 (br. s, 1H), 8.15 (s, 1H), 11.46 (br. s, 1H).

Example 98: (4-(3-(6-bromo-7-(((S)-1-(ethylsulfonyl) pyrrolidine-3-yl)amino)-3H-imidazo[4,5-b] pyridine-2-yl)-2,5-dimethyl-1H-pyrrol-1-yl)-3-methylphenyl) (morpholino) methanone

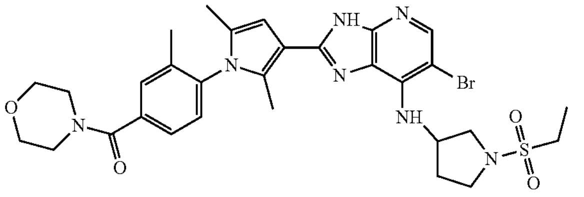 [SMILES: CCS(=O)(=O)N1CCC(Nc2c(Br)cnc3[nH]c(-c4cc(C)n(-c5ccc(C(=O)N6CCOCC6)cc5C)c4C)nc23)C1]

$^{1}$H NMR (300 MHZ, CHLOROFORM-d) δ 1.37 (t, J=7.6, 7.6, 3H), 2.01 (br. s, 3H), 2.06 (br. s, 4H) 2.37 (br. s, 3H), 2.46 (br. s, 1H), 3.02 (m, 2H), 3.45 (m, 1H), 3.61 (m, 3H), 3.78 (br. s, 5H), 3.89 (m, 2H), 5.01 (d, J=7.8, 1H), 5.72 (br. s, 1H), 6.45 (s, 1H) 7.22 (br. s, 1H), 7.26 (m, 1H), 7.36 (m, 1H), 7.47 (m, 1H), 8.17 (s, 1H), 11.92 (br. s, 1H).

<Experimental Example 1> Evaluation of Inhibitory Activity of Enzyme Units

In order to measure the kinase inhibitory activity of the compounds of the above examples, analysis was performed according to the protocol for each kinase.

(1) Mlk1 (Human)

MLK1 kinase protein and compounds were added to a buffer system containing 8 mM MOPS pH7.0, 0.2 mM EDTA, 2 mg/mL casein, 10 mM Magnesium acetate and [γ-$^{33}$P]-ATP, and then a Mg/ATP mixture was added to the system to initiate a reaction. After culturing at room temperature for 40 minutes, 0.5% phosphoric acid was added to terminate the reaction. 10 μL of the reaction mixture was spotted on a P30 filtermat and washed four times in 0.425% phosphoric acid for a total of 4 minutes. After washing once with methanol, the filtermat was dried and scintillated.

(2) Mlk2 (Human)

MLK2 kinase protein and compounds were added to a buffer system containing 8 mM MOPS pH 7.0, 0.2 mM EDTA, 0.33 mg/mL myelin basic protein, 10 mM Magnesium acetate and [y–33P]-ATP, and then a Mg/ATP mixture was added to the system to initiate a reaction. After culturing at room temperature for 40 minutes, 0.5% phosphoric acid was added to terminate the reaction. 10 μL of the reaction mixture was spotted on a P30 filtermat and washed four times in 0.425% phosphoric acid for a total of 4 minutes. After washing once with methanol, the filtermat was dried and scintillated.

(3) Mlk3 (Human)

MLK3 kinase protein and compounds were added to a buffer system containing 8 mM MOPS pH 7.0, 0.2 mM EDTA, 0.33 mg/mL myelin basic protein, 5 mM DTT, 10 mM Magnesium acetate and [γ-$^{33}$P]-ATP, and then a Mg/ATP mixture was added to the system to initiate a reaction. After culturing at room temperature for 120 minutes, 0.5% phosphoric acid was added to terminate the reaction. 10 μL of the reaction mixture was spotted on a P30 filtermat and washed four times in 0.425% phosphoric acid for a total of 4 minutes. After washing once with methanol, the filtermat was dried and scintillated.

The inhibitory effects on MLK1, MLK2, and MLK3 of the compounds according to the present disclosure prepared in the above examples were measured, and the results are shown in Table 1 below. For reference, the part marked "N.T." means "Not Tested."

TABLE 1

| | $IC_{50}$(nM) | | |
|---|---|---|---|
| Examples | MLK3 | MLK2 | MLK1 |
| 1 | 4 | N.T. | N.T. |
| 2 | 4 | N.T. | N.T. |
| 3 | 5 | N.T. | N.T. |
| 4 | 13 | N.T. | 56 |
| 5 | 6 | 92 | 47 |
| 6 | 6 | 181 | 34 |
| 7 | 6 | N.T. | 44 |
| 8 | 7 | N.T. | N.T. |
| 9 | 10 | N.T. | N.T. |
| 10 | 7 | N.T. | N.T. |
| 11 | 7 | N.T. | N.T. |
| 12 | 7 | 65 | 52 |
| 13 | 7 | N.T. | N.T. |
| 14 | 17 | N.T. | N.T. |
| 15 | 34 | N.T. | N.T. |
| 16 | 11 | N.T. | N.T. |
| 17 | 12 | N.T. | N.T. |
| 18 | 13 | 109 | 75 |
| 19 | 14 | 90 | 36 |
| 20 | 14 | 217 | 31 |
| 21 | 15 | 243 | 75 |
| 22 | 17 | 186 | 38 |
| 23 | 17 | 56 | 25 |
| 24 | 20 | 95 | 29 |
| 25 | 26 | 250 | 71 |
| 26 | 19 | N.T. | N.T. |
| 27 | 20 | 178 | 176 |
| 28 | 57 | N.T. | N.T. |
| 29 | 25 | N.T. | N.T. |
| 31 | 35 | N.T. | N.T. |
| 32 | 32 | N.T. | N.T. |
| 33 | 38 | N.T. | N.T. |
| 34 | 41 | N.T. | N.T. |
| 35 | 46 | N.T. | N.T. |
| 36 | 46 | N.T. | N.T. |
| 37 | 47 | N.T. | N.T. |
| 38 | 52 | N.T. | N.T. |
| 39 | 72 | N.T. | N.T. |
| 40 | 68 | N.T. | N.T. |
| 41 | 70 | N.T. | N.T. |
| 42 | 83 | N.T. | N.T. |
| 43 | 85 | N.T. | N.T. |
| 44 | 27 | 211 | 109 |
| 45 | 32 | 524 | 85 |
| 49 | 15 | N.T. | 50 |
| 50 | >30,000 | N.T. | >30,000 |
| 51 | 330 | N.T. | 53 |
| 52 | 324 | N.T. | 87 |
| 53 | 23181 | N.T. | 10561 |
| 54 | 136 | N.T. | 84 |
| 55 | 5922 | N.T. | 4655 |
| 56 | 122 | N.T. | N.T. |
| 57 | 97 | N.T. | N.T. |
| 58 | 53 | N.T. | N.T. |
| 59 | 19 | N.T. | N.T. |
| 60 | 27 | N.T. | 24 |
| 61 | 30 | N.T. | 19 |
| 62 | 17 | N.T. | 22 |
| 63 | 14 | N.T. | 22 |
| 64 | 14 | N.T. | 34 |
| 65 | 26 | N.T. | 42 |
| 66 | 17 | N.T. | 22 |
| 67 | 19 | N.T. | 32 |
| 68 | 16 | N.T. | 25 |
| 69 | 13 | N.T. | 22 |
| 70 | 18 | N.T. | 36 |
| 71 | 26 | N.T. | 36 |
| 72 | 15 | N.T. | 25 |
| 73 | 25 | N.T. | 25 |
| 74 | 46 | N.T. | 43 |
| 75 | 16 | N.T. | 30 |
| 76 | 63 | N.T. | 64 |
| 77 | 7 | N.T. | 19 |
| 78 | 47 | N.T. | 25 |
| 79 | 7 | N.T. | 35 |
| 80 | 33 | N.T. | 33 |
| 81 | 9 | N.T. | 14 |
| 82 | 14 | N.T. | 34 |
| 83 | 12 | N.T. | 22 |
| 84 | 8 | N.T. | 16 |
| 85 | 11 | N.T. | 14 |
| 86 | 7 | N.T. | 15 |
| 87 | 13 | N.T. | 24 |
| 88 | 52 | N.T. | 82 |
| 89 | 81 | N.T. | 169 |
| 90 | 92 | N.T. | 160 |
| 91 | 25 | N.T. | 19 |
| 92 | 26 | N.T. | 15 |
| 93 | 54 | N.T. | 33 |
| 94 | 73 | N.T. | 52 |
| 95 | 60 | N.T. | 37 |
| 96 | 137 | N.T. | 145 |
| 97 | 20 | N.T. | 14 |
| 98 | 14 | N.T. | 14 |

According to the results in Table 1 above, it can be understood that the compound of Formula 1 according to the present disclosure had excellent MLK family, particularly, MLK3 inhibitory effect.

<Experimental Example 2> Identification of Mechanism of Action related to MLK3 Activity Inhibition In order to identify the mechanism of action related to the inhibition of MLK3 activity of the compounds, using the human breast cancer cell line MDA-MB-231, the compounds of Example 7 were treated at a concentration of 3 μM to identify phosphorylation patterns of MKK3, p38, and paxillin, which are sub-signal transduction proteins of MLK3 by Western blot. The results are shown in FIG. 1.

The cell line was spread on a 6-well plate at a concentration of 40,000 cells/well, and after 24 hours, the compounds of Example 7 were treated and cultured for 60 hours. Thereafter, the cultured cells were added to the lysis buffer, Protein extraction solution (RIPA buffer; Elpis Biotech), with a protease inhibitor cocktail (cat.no.88666) and a phosphatase inhibitor cocktail (cat no.A32957) from Pierce to dissolve, and centrifugation (14,000 rpm) was performed at 4° C. for 15 minutes to obtain pure protein remaining in the upper layer. Protein was quantified using BCA protein quantification kit (Bio-Rad), and the same amount of protein was mixed in sample buffer (Elpis Biotech), heated at 100° C. for 10 minutes, and separated from 10% SDS-polyacrylamide gel. The subsequent procedure was based on a basic western blot experimental method, and the separated protein was transferred to a PVDF membrane (Amersham Biosciences), and the protein expression level using an antibody and millipore's ECL was identified using Atto's chemiluminescence imaging system. Antibodies used were anti-MKK3 (8535), anti-phospho-MKK3 (12280), anti-p38 (9212), anti-phospho-p38 (9211), anti-paxillin (2542), anti-phospho-paxillin (2541) from Cell signaling.

Referring to FIG. 1, it was identified that the compounds of the examples according to the present disclosure exhibited the effect of inhibiting the activity of MLK3 subproteins by inhibiting phosphorylation of MLK3 and MLK3 sub-signal transduction proteins.

<Experimental Example 3> Evaluation 1 of Cancer Cell Proliferation Inhibitory Activity (Cancer Cell Killing Effect)

In order to identify whether the compound has anticancer activity, the human breast cancer cell line MDA-MB-231, the colorectal cancer cell line HT-29, the acute myeloid leukemia cell line U937, and the chronic myeloid leukemia cell line K562 were used. The cell line was cultured using RPMI-1640 medium containing 10% fetal bovine serum. Welgene products were used as the medium, and hyclone products were used for fetal bovine serum, and 1% of antibiotics for cell culture from Gibco were used as the culture medium.

Each cell was spread on a 96-well plate at a concentration of 2,000 cells/well, and 10 M of each of the compounds according to the examples was treated after 24 hours. The compounds used were prepared with 10 mM DMSO, and diluted with a medium so that the final concentration was 10 μM, and the final concentration of DMSO was 0.1%. After 72 hours of treatment with the compounds, anticancer activity was measured using CCK-8 (Dojindo). The measurement method complied with the experimental method presented in the product, and the absorbance at a wavelength of 450 nm was measured with a microplate reader (Hidex) to identify the presence of anticancer activity of the compounds. When the absorbance of the wells without cells was calculated as '0' and the absorbance of the negative control group not treated with the compounds was calculated as '100, ' the relative % average value was deemed as the cell activity value, (100-cell activity value) % was expressed as an anticancer activity value to evaluate the degree of inhibition of cell activity compared to the negative control group. When the anticancer activity value was 50% or more, it was denoted as '+++', when it was more than 10% and less than 50%, it was denoted as '++', and when it was 10% or less, it was denoted as '+.'

The results of the above experiments are shown in Table 2 below.

TABLE 2

| | Cancer cell proliferation inhibitory activity | | | |
|---|---|---|---|---|
| Examples | MDAMB231 | U937 | HT29 | K562 |
| 1 | ++ | ++ | ++ | + |
| 2 | +++ | +++ | +++ | +++ |
| 3 | +++ | +++ | ++ | +++ |
| 4 | ++ | +++ | +++ | +++ |
| 7 | ++ | +++ | ++ | +++ |
| 13 | ++ | +++ | ++ | ++ |
| 14 | + | ++ | ++ | + |
| 15 | +++ | ++ | + | ++ |
| 16 | ++ | +++ | ++ | +++ |
| 26 | ++ | ++ | ++ | + |
| 31 | + | ++ | +++ | ++ |
| 33 | ++ | ++ | + | + |
| 35 | ++ | ++ | +++ | + |
| 37 | +++ | ++ | +++ | + |
| 38 | ++ | +++ | +++ | +++ |
| 39 | ++ | + | ++ | ++ |
| 40 | ++ | +++ | +++ | ++ |

Referring to Table 2, it was identified that the compounds of the examples according to the present disclosure exhibited a cell activity inhibitory effect (cancer cell killing effect) of cancer cells against MDA-MB-231, HT-29, U937 and K562 cell lines, which are cancer cell lines.

<Experimental Example 4> Evaluation 2 of Cancer Cell Proliferation Inhibitory Activity (Cancer Cell Killing Effect)

In order to identify whether the compounds have anticancer activity, the acute myeloid leukemia cell line U937, the acute lymphoblastic leukemia cell line Jurkat, the gastric cancer cell lines AGS, Hs76T, and the human lung cancer cell line A549 were used. The cell line was cultured using RPMI-1640 medium (U937, Jurkat, AGS, A549) or DMEM (Hs746T) medium containing 10% fetal bovine serum. Welgene products were used as the medium, and hyclone products were used for fetal bovine serum, and 1% of antibiotics for cell culture from Gibco were used as the culture medium.

Each cell was spread on a 96-well plate at a concentration of 2,000 cells/well, and 10 μM of each of the compounds according to the examples was treated after 24 hours. The compounds used were prepared with 10 mM DMSO, and diluted with a medium so that the final concentration was 10 μM, and the final concentration of DMSO was 0.1%. After 72 hours of treatment with the compounds, anticancer activity was measured using CCK-8 (Dojindo). The measurement method complied with the experimental method presented in the product, and the absorbance at a wavelength of 450 nm was measured with a microplate reader (Hidex) to identify the presence of anticancer activity of the compounds. When the absorbance of the wells without cells was calculated as '0' and the absorbance of the negative control group not treated with the compounds was calculated as '100,' the relative % average value was deemed as the cell activity value, (100-cell activity value) % was expressed as an anticancer activity value to evaluate the degree of inhibition of cell activity compared to the negative control group. When the anticancer activity value was 50% or more, it was denoted as '+++', when it was more than 10% and less than 50%, it was denoted as '++', and when it was 10% or less, it was denoted as '+' For reference, the part marked "N.T." means "Not Tested."

The results of the above experiments are shown in Table 3 below.

TABLE 3

| | Cancer cell proliferation inhibitory activity | | | | |
|---|---|---|---|---|---|
| Examples | U937 | Jurkat | AGS | Hs746T | A549 |
| 1 | ++ | ++ | ++ | N.T. | N.T. |
| 2 | ++ | ++ | +++ | N.T. | N.T. |
| 3 | ++ | +++ | N.T. | +++ | ++ |
| 4 | +++ | +++ | +++ | N.T. | N.T. |
| 5 | ++ | ++ | +++ | N.T. | N.T. |
| 6 | ++ | +++ | +++ | N.T. | N.T. |
| 7 | +++ | +++ | +++ | N.T. | N.T. |
| 8 | +++ | +++ | +++ | +++ | +++ |
| 9 | +++ | +++ | +++ | +++ | +++ |
| 10 | ++ | +++ | ++ | N.T. | N.T. |
| 11 | ++ | +++ | +++ | N.T. | N.T. |
| 12 | ++ | ++ | +++ | N.T. | N.T. |
| 13 | ++ | +++ | +++ | N.T. | N.T. |
| 14 | ++ | ++ | ++ | N.T. | N.T. |
| 15 | ++ | + | ++ | N.T. | N.T. |
| 16 | + | ++ | ++ | N.T. | N.T. |

TABLE 3-continued

| Examples | U937 | Jurkat | AGS | Hs746T | A549 |
|---|---|---|---|---|---|
| | Cancer cell proliferation inhibitory activity | | | | |
| 17 | ++ | +++ | +++ | N.T. | N.T. |
| 18 | N.T. | N.T. | +++ | ++ | ++ |
| 19 | +++ | +++ | +++ | N.T. | N.T. |
| 20 | + | ++ | ++ | N.T. | N.T. |
| 21 | ++ | ++ | +++ | N.T. | N.T. |
| 22 | N.T. | N.T. | ++ | N.T. | N.T. |
| 23 | ++ | +++ | ++ | N.T. | N.T. |
| 24 | ++ | ++ | ++ | N.T. | N.T. |
| 25 | ++ | +++ | +++ | N.T. | N.T. |
| 26 | ++ | ++ | ++ | N.T. | N.T. |
| 27 | + | + | ++ | N.T. | N.T. |
| 28 | + | ++ | ++ | N.T. | N.T. |
| 29 | + | ++ | ++ | N.T. | N.T. |
| 30 | + | ++ | ++ | N.T. | N.T. |
| 31 | ++ | ++ | ++ | N.T. | N.T. |
| 32 | ++ | ++ | ++ | N.T. | N.T. |
| 33 | + | ++ | ++ | N.T. | N.T. |
| 34 | ++ | ++ | ++ | N.T. | N.T. |
| 35 | ++ | ++ | ++ | N.T. | N.T. |
| 36 | + | + | + | N.T. | N.T. |
| 37 | ++ | ++ | ++ | N.T. | N.T. |
| 38 | ++ | +++ | +++ | N.T. | N.T. |
| 39 | ++ | +++ | +++ | N.T. | N.T. |
| 40 | ++ | +++ | ++ | N.T. | N.T. |
| 41 | ++ | ++ | ++ | N.T. | N.T. |
| 42 | ++ | +++ | +++ | N.T. | N.T. |
| 43 | ++ | +++ | ++ | N.T. | N.T. |
| 44 | ++ | ++ | ++ | N.T. | N.T. |
| 45 | ++ | + | ++ | N.T. | N.T. |
| 46 | ++ | +++ | ++ | N.T. | N.T. |
| 50 | N.T. | N.T. | N.T. | N.T. | N.T. |
| 51 | +++ | +++ | N.T. | +++ | ++ |
| 52 | +++ | +++ | N.T. | +++ | ++ |
| 53 | N.T. | N.T. | N.T. | N.T. | N.T. |
| 54 | +++ | +++ | N.T. | +++ | +++ |
| 55 | N.T. | N.T. | N.T. | N.T. | N.T. |
| 56 | +++ | +++ | +++ | +++ | +++ |
| 57 | +++ | +++ | +++ | +++ | +++ |
| 58 | + | + | + | + | + |
| 59 | ++ | ++ | + | ++ | + |
| 60 | +++ | +++ | +++ | +++ | +++ |
| 61 | +++ | +++ | +++ | +++ | +++ |
| 62 | +++ | +++ | +++ | +++ | +++ |
| 63 | +++ | +++ | +++ | +++ | +++ |
| 64 | +++ | +++ | +++ | +++ | +++ |
| 65 | +++ | +++ | +++ | +++ | + |
| 66 | ++ | +++ | +++ | +++ | ++ |
| 67 | +++ | +++ | +++ | ++ | ++ |
| 68 | +++ | +++ | +++ | +++ | +++ |
| 69 | +++ | +++ | +++ | ++ | ++ |
| 70 | +++ | +++ | +++ | ++ | ++ |
| 71 | ++ | +++ | +++ | +++ | + |
| 72 | +++ | +++ | +++ | +++ | ++ |
| 73 | +++ | +++ | +++ | +++ | +++ |
| 74 | +++ | +++ | +++ | +++ | +++ |
| 75 | +++ | +++ | +++ | +++ | +++ |
| 76 | +++ | +++ | +++ | +++ | + |
| 77 | +++ | +++ | +++ | ++ | ++ |
| 78 | +++ | +++ | +++ | +++ | +++ |
| 79 | +++ | +++ | +++ | +++ | +++ |
| 80 | +++ | +++ | +++ | +++ | +++ |
| 81 | +++ | +++ | +++ | ++ | ++ |
| 82 | +++ | +++ | +++ | +++ | +++ |
| 83 | +++ | +++ | +++ | +++ | ++ |
| 84 | +++ | +++ | +++ | +++ | +++ |
| 85 | +++ | +++ | +++ | ++ | ++ |
| 86 | +++ | +++ | +++ | +++ | +++ |
| 87 | +++ | +++ | +++ | +++ | +++ |
| 88 | ++ | +++ | +++ | +++ | ++ |
| 89 | + | ++ | ++ | ++ | + |
| 90 | ++ | +++ | +++ | ++ | ++ |
| 91 | +++ | +++ | +++ | +++ | +++ |
| 92 | +++ | +++ | +++ | +++ | ++ |
| 93 | +++ | +++ | +++ | +++ | ++ |
| 94 | ++ | ++ | ++ | +++ | + |
| 95 | + | ++ | ++ | ++ | + |
| 96 | + | + | + | ++ | + |
| 97 | +++ | +++ | +++ | ++ | +++ |
| 98 | +++ | +++ | +++ | +++ | ++ |

Referring to Table 3, it can be understood that the compounds of the examples according to the present disclosure exhibited a cell activity inhibitory effect (cancer cell killing effect) of cancer cells against U937, Jurkat, AGS, Hs746T and A549 cell lines, which are cancer cell lines.

<Experimental Example 5> Evaluation 2 of Cancer Cell Proliferation Inhibitory Activity (Cancer Cell Killing Effect)

In order to identify the anticancer activity according to the concentration of the compounds, using the human breast cancer cell line MDA-MB-231 and the acute T-cell leukemia cell line Jurkat, the compounds of Example 7 were treated at concentrations of 0.1, 0.3, 1, 3, 10, and 30 μM. The anticancer activity was evaluated in the same manner as in Experimental Example 3, and the concentration inhibiting 50% was calculated using an Excel program and expressed as an $IC_{50}$ value.

The results of the above experiments are shown in FIG. 2.

Referring to FIG. 2, it was identified that the compounds of the examples according to the present disclosure exhibited an excellent inhibition of cancer cell activity (cancer cell killing effect) at a concentration in a micromolar unit with respect to MDA-MB-231 and Jurkat cell lines, which are cancer cell lines.

<Experimental Example 6> Evaluation 4 of Cancer Cell Proliferation Inhibitory Activity (Cancer Cell Killing Effect)

In order to identify the anticancer activity according to the concentration of the compounds, using the human gastric cancer cell line HS746T, the compounds of the examples were treated at concentrations of 0.1, 0.3, 1, 3, 10, and 30 μM, respectively. The anticancer activity was evaluated in the same manner as in Experimental Example 3, and the concentration inhibiting 50% was calculated using an Excel program and expressed as an $IC_{50}$ value. For reference, the part marked "N.T." means "Not Tested."

The results of the above experiments are shown in Table 4 below.

TABLE 4

| Examples | $IC_{50}$(μM) |
|---|---|
| 7 | 7.4 |
| 8 | 3.4 |
| 9 | 3.69 |
| 50 | N.T. |
| 51 | >10 |
| 52 | >10 |
| 53 | N.T. |
| 54 | 6.78 |
| 55 | N.T. |
| 56 | 5.63 |
| 57 | 5.49 |
| 58 | N.T. |
| 59 | N.T. |

TABLE 4-continued

| Examples | $IC_{50}$(μM) |
|---|---|
| 60 | 5.56 |
| 61 | 5.32 |
| 62 | 5.53 |
| 63 | 5.28 |
| 64 | 4.09 |
| 65 | 2.71 |
| 66 | 5.19 |
| 67 | >10 |
| 68 | N.T. |
| 69 | N.T. |
| 70 | N.T. |
| 71 | N.T. |
| 72 | 9.28 |
| 73 | 5.42 |
| 74 | 6.12 |
| 75 | 6.23 |
| 76 | 7 |
| 77 | >10 |
| 78 | 7.33 |
| 79 | 3.06 |
| 80 | 6.51 |
| 81 | >10 |
| 82 | 5.97 |
| 83 | 8.59 |
| 84 | 5.85 |
| 85 | >10 |
| 86 | 4.82 |
| 87 | 5.71 |
| 88 | 7.72 |
| 89 | >10 |
| 90 | >10 |
| 91 | 6.7 |
| 92 | 8.65 |
| 93 | 6.76 |
| 94 | 5.96 |
| 95 | >10 |
| 96 | >10 |
| 97 | >10 |
| 98 | 8.11 |

Referring to Table 4, it was identified that the compounds of the examples according to the present disclosure exhibited excellent inhibition of cancer cell activity (cancer cell killing effect) at a concentration in a micromolar unit with respect to the Hs746T cell line, which is a cancer cell line.

<Experimental Example 7> Evaluation of Cancer Cell Metastasis Inhibitory Activity In order to identify the cancer metastasis inhibitory effect of the compounds, the human breast cancer cell line MDA-MB-231 was used. After culturing for 24 hours at 15,000 cells/well in an ImageLock 96-well plate (Essen BioScience), it was replaced with a serum-free medium. Using a 96-well Wound maker (Essen BioScience), cells were uniformly scraped for each well to form a wound, the compounds were treated at a concentration of 1 or 3 μM, respectively, and every 12 hours, the remaining distance of the wound was measured using IncuCyte software. All experiments were repeated three times, and FIG. 3 is a photograph showing the result after 60 hours of wound formation.

Referring to FIG. 3, it was identified that the compounds of the examples according to the present disclosure exhibited an excellent cancer metastasis inhibitory effect at a concentration in a micromolar unit with respect to the cancer cell line, MDA-MB-231.

<Experimental Example 8> Fibrosis Inhibition Evaluation 1

In order to identify whether the compounds inhibit the symptoms of non-alcoholic fatty liver disease, the human liver cancer cell line HepG2 was purchased from ATCC and used. The cell line was cultured in 5% $CO_2$, 37° C. environment using DMEM (Dulbecco's modification of Eagle's medium) added with Gibco's FBS (Fetal Bovine Serum) 10%, penicillin 100 U/mL, and streptomycin 100 μg/mL.

To induce fibrosis, palmitic acid (sigma) was used. 20 mM of palmitic acid and 0.001N of NaOH were mixed with DPBS (Dulbecco's Phosphate-Buffered Saline), maintained at 70° C. for 30 minutes to make a suspension, and then mixed with 5% fatty acid free BSA solution in a 1:3 ratio (5 mM). Then, conjugation was carried out at 37° C.

The group that did not induce fibrosis by treatment with palmitic acid was placed as the non-induction group, the group treated with palmitic acid was placed as the negative control group, and the group treated with palmitic acid and compound was placed as the experimental group.

After cell culture, total RNA was isolated using Trizol reagent (invitrogen) according to the manufacturer's instructions. 1 μg of total RNA thus obtained was converted into cDNA using a reverse-transcription system. The types and sequences of primers used in the experiment are shown in Table 5 below. Real-time PCR was performed according to the method recommended by the manufacturer using the power SYBR green PCR master mix (Applied Biosystem), and relative gene expression values were quantitatively expressed based on the house keeping gene α-actin. 2× SYBR Green PCR Master Mix 10 μl, cDNA 9 μl, primer (sense) 0.2 μl, primer (anti-sense) 0.2 μl, and distilled water 0.6 μl were mixed to adjust the total volume to 20 μl. For initial denaturation, only the first cycle was amplified at 95° C. for 10 minutes, the remaining 40 cycles were amplified at 95° C. for 15 seconds, and annealing and extension were performed at 60° C. for 1 minute.

The relative degree of expression inhibition (%) of each fibrosis marker gene by the compounds of the examples was calculated according to Equation 1 below.

$$\text{Relative degree of expression inhibition (\%)} = 100 - \text{relative degree of expression (\%)} = 100 - \left(\frac{\text{experimental group} - \text{non-induction group}}{\text{negative control group} - \text{non-induction group}} \times 100\ (\%)\right) \quad \text{[Equation 1]}$$

TABLE 5

| Genes | Forward primer (5'-3') | Reverse primer (5'-3') |
|---|---|---|
| β-actin | GGACTTCGAGCAAGAGATGG (SEQ ID NO: 1) | AGCACTGTGTTGGCGTACAG (SEQ ID NO: 2) |
| α-SMA | CCGACCGAATGCAGAAG (SEQ ID NO: 3) | ACAGAGTATTTGCGCTCCGGA (SEQ ID NO: 4) |

TABLE 5-continued

| Genes | Forward primer (5'-3') | Reverse primer (5'-3') |
|---|---|---|
| Col1A1 | CGAAGACATCCCACCAATCAC (SEQ ID NO: 5) | ACAGATCACGTCATCGCACAA (SEQ ID NO: 6) |
| Col6A3 | CTCTACCGAGCCCAGGTGTT (SEQ ID NO: 7) | ATGAGGGTGCGAACGTACTG (SEQ ID NO: 8) |

The results of the above experiments are shown in Table 6 below.

TABLE 6

| | Relative degree of expression inhibition (%) | | |
|---|---|---|---|
| | α-SMA | Col1A1 | Col6A3 |
| Non-induction group | 100 | 100 | 100 |
| Negative control group | 0 | 0 | 0 |
| Experimental group (Example 7) | 73.1 | 200.2 | 116.2 |

Referring to Table 6, it was identified that the compounds of the examples according to the present disclosure inhibited the expression of the fibrosis marker gene induced by palmitic acid in HepG2, a liver cancer cell line, through which the antifibrotic effect of the compounds according to the present disclosure was identified.

<Experimental Example 9> Fibrosis Inhibition Evaluation 2

In order to identify the preventive and therapeutic effect of the compounds for non-alcoholic steatohepatitis, the human liver cancer cell line HepG2 was purchased from ATCC and used. The cell line was cultured in 5% $CO_2$, 37° C. environment using DMEM (Dulbecco's modification of Eagle's medium) added with Gibco's FBS (Fetal Bovine Serum) 10%, penicillin 100 U/mL, and streptomycin 100 μg/mL.

To induce fibrosis, palmitic acid (sigma) was used. 20 mM of palmitic acid and 0.001 N of NaOH were mixed with DPBS (Dulbecco's Phosphate-Buffered Saline), maintained at 70° C. for 30 minutes to make a suspension, and then mixed with 5% fatty acid free BSA solution in a 1:3 ratio (5 mM). Then, conjugation was carried out at 37° C.

The group that did not induce fibrosis by treatment with palmitic acid was placed as the non-induction group, the group treated with palmitic acid was placed as the negative control group, and the group treated with palmitic acid and compound was placed as the experimental group.

After cell culture, total RNA was isolated using Trizol reagent (invitrogen) according to the manufacturer's instructions. 1 μg of total RNA thus obtained was converted into cDNA using a reverse-transcription system. The types and sequences of primers used in the experiment are shown in Table 6 below. Real-time PCR was performed according to the method recommended by the manufacturer using the power SYBR green PCR master mix (Applied Biosystem), and relative gene expression values were quantitatively expressed based on the house keeping gene β-actin. 2× SYBR Green PCR Master Mix 10 μl, cDNA 9 μl, primer (sense) 0.2 μl, primer (anti-sense) 0.2 μl, and distilled water 0.6 μl were mixed to adjust the total volume to 20 μl. For initial denaturation, only the first cycle was amplified at 95° C. for 10 minutes, the remaining 40 cycles were amplified at 95° C. for 15 seconds, and annealing and extension were performed at 60° C. for 1 minute.

The relative degree of expression inhibition (%) of each fibrosis marker gene by the compounds of the examples was calculated according to Equation 1 above.

TABLE 7

| Genes | Forward primer (5'-3') | Reverse primer (5'-3') |
|---|---|---|
| β-actin | TAGCCATCCAGGCTGTGCTG (SEQ ID NO: 9) | CAGGATCTTCATGAGGTAGTC (SEQ ID NO: 10) |
| Fibronectin-1 | CCCTATCTCTGAYACCGTTGTCC (SEQ ID NO: 11) | TGCCGCAACTACTGTGATTCGG (SEQ ID NO: 12) |
| TGF-β1 | TGCTCCAAACCACAGAGTAGGC (SEQ ID NO: 13) | CCCAGAACACTAAGCCCATTGC (SEQ ID NO: 14) |
| α-SMA | TCAGCGCCTCCAGTTCCT (SEQ ID NO: 15) | AAAAAAAACCACGAGTAACAAATCAA (SEQ ID NO: 16) |

The results of the above experiments are shown in Table 8 below.

TABLE 8

| | Relative degree of expression inhibition (%) | | |
|---|---|---|---|
| | α-SMA | TGF-β1 | Fibronectin-1 |
| Non-induction group | 100 | 100 | 100 |
| Negative control group | 0 | 0 | 0 |
| Example 2 | 48.35 | 97.39 | 77.72 |
| Example 3 | ambiguous | 109.05 | 72.85 |
| Example 11 | 24.73 | 99.40 | 86.85 |
| Example 12 | 49.92 | 113.03 | 74.32 |
| Example 36 | 79.46 | 66.72 | 82.94 |
| Example 44 | 73.45 | 57.05 | 75.60 |
| Example 45 | 74.97 | 33.15 | 60.64 |
| Example 53 | 74.74 | 33.15 | 69.92 |

TABLE 8-continued

| | Relative degree of expression inhibition (%) | | |
|---|---|---|---|
| | α-SMA | TGF-β1 | Fibronectin-1 |
| Example 58 | 66.53 | 48.93 | 69.83 |
| Example 76 | 69.54 | 121.79 | 93.95 |
| Example 81 | 61.69 | 44.28 | 61.05 |
| Example 88 | 74.86 | 56.45 | 86.78 |
| Example 93 | 73.82 | 42.54 | 74.05 |
| Example 95 | 67.81 | 45.25 | 65.78 |
| Example 96 | 37.83 | 92.86 | 61.67. |

Referring to Table 8, it was identified that the compounds of the examples according to the present disclosure inhibited the expression of the fibrosis marker gene induced by palmitic acid in HepG2, a liver cancer cell line, through which the antifibrotic effect of the compounds according to the present disclosure was identified.

<Experimental Example 10> Evaluation of Inhibition of Non-Alcoholic Steatohepatitis in Animal Models In order to identify the effect of the compounds on non-alcoholic fatty liver disease, an animal model with non-alcoholic steatohepatitis in which 6-week-old C57BL/6J mice were fed a methionine and choline deficiency (MCD) diet was used. The normal diet group was fed the normal diet (Chow) voluntarily, and the MCD group was induced to the non-alcoholic steatohepatitis model through the voluntary feeding of the MCD diet for 8 weeks (Molecules 2014, 19, 8189-8211). Animals were housed in well-ventilated environmental conditions maintained at a temperature of 23±2° C. and a relative humidity of 55±5%. Fluorescent lighting was provided for about 12 hours per day, and the litter was changed once a week.

After 8 weeks of normal diet or MCD diet, the MCD-fed animals were administered drugs intraperitoneally once a day for 4 weeks. At that time, all animals maintained the conventional diet. Among the MCD-fed animals, the "experimental group" was administered with 10 mg/kg of the compound of Example 7, and the "negative control group" was administered with Vehicle intraperitoneally once a day for 4 weeks. The configuration of the animal group of this experimental example is shown in Table 9 below.

TABLE 9

| | Diets (12 weeks) | Dosage (mg/kg) | Start of dosing | End of dosing |
|---|---|---|---|---|
| Non-induction group | Normal diet | Not applicable | Not applicable | Not applicable |
| Negative control group | MCD diet | 10 | Week 9 | Week 12 |
| Experimental group | MCD diet | 10 | Week 9 | Week 12 |

Body weight, feed and drinking water intake were measured once a week, and serum biochemical indicators (ALT, AST, ALP, TG, Glucose, and Albumin) and histopathological indicators (brunt score evaluation after Sirius-Red staining) after 12 weeks of experimentation were evaluated. Some of the results are shown in FIGS. 4 to 6. Referring to FIGS. 4 to 6, it was confirmed that the compounds of the examples according to the present disclosure improved the evaluation indicators for non-alcoholic steatohepatitis induced by the MCD diet, through which the preventive and therapeutic effects of the compounds according to the present disclosure on non-alcoholic steatohepatitis was identified.

<Experimental Example 11> Evaluation of Inhibitory Activity Against LRRK2

In order to identify the activity inhibitory effect on the LRRK2 wild-type and LRRK2 mutant (G2019S) kinase of the example compound according to the present disclosure, BL21-derived *E. coli* bacteria (*E. coli*) were cultured in a 24-well plate until the growth phase (log phase). After culturing, T7 phage tagged with LRRK2 wild-type or LRRK2 mutant (G2019S) was used to infect the multiplicity of infection (MOI) at 0.4. Thereafter, the *E. coli* bacteria were stirred at 32° C. for 90 to 150 minutes to allow dissolution. The lysate of *E. coli* bacteria was centrifuged (6,000×g) and filtered (0.2 μm), and the obtained tagged T7 phage was transfected into HEK293 cells, and a DNA-tagged kinase protein (LRRK2 or LRRK2 G2019S) was obtained.

Streptavidin-coated magnetic beads were treated with bionylated low-molecular ligands at room temperature for 30 minutes to prepare an affinity resin. After blocking the biotinylated ligand with extra biotin, it is washed with Pierce's buffer, SeaBlock (1% BSA, 0.05% Tween 20, 1 mM DTT) to remove unbound ligand and reduce non-specific binding. The binding reaction was carried out by mixing the affinity beads obtained from HEK293 cells with the kinase and the ligand bound, and the example compound contained in 1× buffer.

The compound was prepared at a concentration of 40× in 100% DMSO and used after dilution, and all binding reactions were performed in a final volume of 0.02 ml in a 384-well plate. After stirring the plate for 1 hour at room temperature, the affinity beads were washed with wash buffer (1×PBS, 0.05% Tween 20), and were resuspended in elution buffer (1× PBS, 0.05% Tween 20, 0.5 μM non-biotinylated affinity ligand).

The activity inhibitory effect on the LRRK2 wild-type and LRRK2 mutant (G2019S) kinases of the example compounds according to the present disclosure was measured and shown in Table 10 below.

TABLE 10

| Compounds | Concentrations (nM) | Residual active values (%) LRRK2 | LRRK2(G2019S) |
|---|---|---|---|
| Example 2 | 100 | 17.0 | 4.0 |
| | 500 | 3.5 | 0.8 |
| Example 3 | 100 | 17.0 | 3.5 |
| | 500 | 3.1 | 0.9 |
| Example 7 | 100 | 2.9 | 2.3 |
| | 500 | 0.4 | 1.5 |
| Example 11 | 100 | 28.0 | 7.9 |
| | 500 | 6.9 | 1.7 |
| Example 12 | 100 | 16.0 | 3.6 |
| | 500 | 3.7 | 0.5 |
| Example 25 | 100 | 49.0 | 15.0 |
| | 500 | 17.0 | 3.3 |
| Example 54 | 100 | 24.0 | 6.3 |
| | 500 | 4.1 | 0.4 |
| Example 58 | 100 | 5.0 | 1.4 |
| | 500 | 0.7 | 0.2 |
| Example 76 | 100 | 3.6 | 0.9 |
| | 500 | 1.1 | 0.1 |
| Example 81 | 100 | 0.7 | 0.0 |
| | 500 | 0.6 | 0.1 |

TABLE 10-continued

| Compounds | Concentrations (nM) | Residual active values (%) LRRK2 | LRRK2(G2019S) |
|---|---|---|---|
| Example 88 | 100 | 73.0 | 57.0 |
| | 500 | 46.0 | 19.0 |
| Example 93 | 100 | 60.0 | 66.0 |
| | 500 | 51.0 | 25.0 |
| Example 94 | 100 | 70.0 | 59.0 |
| | 500 | 40.0 | 16.0 |
| Example 95 | 100 | 68.0 | 79.0 |
| | 500 | 43.0 | 24.0 |
| Example 96 | 100 | 0.4 | 0.8 |
| | 500 | 0.0 | 0.6 |
| Example 98 | 100 | 18.0 | 8.2 |
| | 500 | 3.5 | 1.0 |

Referring to Table 10, the activity inhibitory effect on the LRRK2 wild-type and LRRK2 mutant (G2019S) kinase of the example compounds according to the present disclosure was identified.

<Experimental Example 12> Evaluation of Phosphorylation Inhibition of LRRK2

In order to identify the phosphorylation inhibitory effect of the LRRK2 kinase of the example compound according to the present disclosure, the NIH-3T3 cell line known as the LRRK2 expressing cell line was used, and DMEM medium supplemented with Gibco's FBS 10% and Penicillin/Streptomycin 1% was used and cultured in an environment of 5% $CO_2$, 37° C.

After culturing in a 12-well plate with $2\times10^5$ cells, LRRK2 inhibitors HG-10-102-01 and GNE0877 (comparative compounds 1 and 2, respectively), and MLK inhibitor CEP1347 (comparative compound 3) of Example 7 were treated with concentrations of 5, 20, 100, and 1000 nM, respectively. After culturing for 24 hours, protein was obtained using lysis buffer (50 mM Tris-HCl (pH7.5), 0.5% TX-100, 150 mM NaCl, 0.5 mM EDTA, Protease inhibitor mixture, 0.2 mM PMSF). The obtained protein was quantified using the BCA kit of Thermo fisher scientific, and after heating at 75° C. for 5 minutes, Western blotting was performed. As the primary antibodies of LRRK2, phospho-LRRK2 and β-actin, Abcam's products were used, and LRRK2 and phospho-LRRK2 antibodies were reacted at a ratio of 1:1000 and β-actin antibody at a ratio of 1:5000. The results of the above experiments are shown in FIG. 7.

Referring to FIG. 7, it was identified that the example compound according to the present disclosure inhibited LRRK2 phosphorylation at a level similar to that of Comparative Compounds 1 and 2, which are LRRK2 inhibitors, in the NIH-3T3 cell line, which is an LRRK2-expressing cell line.

<Experimental Example 13> Evaluation of Protective Effect against Nerve Cell Damage In order to identify the protective effect of the example compound according to the present disclosure against nerve damage, a fetus was isolated from a rat at 15 days of pregnancy, and then the cerebral cortical region was extracted and used as primary cerebral cortical neurons. The cells were aliquoted in a 12-well plate with $2\times10^5$ cells and cultured for 24 hours, then replaced with Neurobasal medium from Gibco and cultured. LRRK2 G22019S was transfected using Invitrogen's Lipofectamine and Opti-MEM on the 11th day in vitro, and 6 hours later, the example compounds or comparative compounds were treated at concentrations of 0.01, 0.1, and 1 μM. After fixing the cells by treatment with 4% PFA, neurites were observed by immunostaining using Abcam's GFP antibody. The protective effect of each compound against nerve damage was evaluated by changing the length of the neurite. The results of the above experiments are shown in FIG. 8.

Referring to FIG. 8, it was identified that the example compound according to the present disclosure dose-dependently protected against neuronal damage caused by LRRK2 G2019S mutation overexpression.

<Experimental Example 14> Antiviral Effect Evaluation 1

In order to identify the inhibitory effect of the compound on influenza activity, the MDCK cell line grown sufficiently in a 96-well plate was washed with phosphate-buffered saline (PBS), and then was inoculated with influenza virus of 50-100 plaque forming units (PFU) per well. It was left at 35° C. for about 1 hour to infect the cells with the virus. After removing the culture medium and washing with phosphate-buffered saline, a MEM culture medium containing 2 μg/ml TPCK-trypsin in which each example compound was diluted to various concentrations was added to each well. In the third day after infection, cell activity was assessed using MTT (Sigma) [Jang YJ et al., (2014). Antiviral Res 107:66-75.]. By measuring the absorbance at 540 nm and 690 nm wavelengths, 50% cytotoxic concentration ($CC_{50}$) and 50% effective concentration ($EC_{50}$) were calculated.

The results of the above experiments are shown in Table 11 below. For reference, the part marked with "ND" means "Not Determined."

TABLE 11

| Compounds | Toxicity ($CC_{50}$, μM) Mock | Antiviral activity ($EC_{50}$, μM) PR8 | HK | LE | Selectivity index: $CC_{50}/EC_{50}$ PR8 | HK | LE |
|---|---|---|---|---|---|---|---|
| Example 23 | >100 | >100 | 31.6 | >100 | ND | >3.2 | ND |
| Example 12 | >100 | 100 | 27 | >100 | >1.0 | >3.7 | ND |
| Example 7 | >100 | 31.9 | 40 | >100 | >3.1 | >2.5 | ND |
| Example 4 | >100 | 11.1 | 9.8 | 9.9 | >9.0 | >10.2 | >10.1 |
| Example 17 | >100 | 92.9 | 10.8 | >100 | >1.1 | >9.3 | ND |

Referring to Table 11, it was identified that the compounds of the examples according to the present disclosure exhibited an effect (antiviral effect) of inhibiting cytotoxicity due to virus infection at a micromolar concentration of the influenza virus-infected MDCK cell line.

<Experimental Example 15> Antiviral Effect Evaluation 2

In order to identify the inhibitory effect of the compound on influenza activity, the A549 cell line, a human lung cancer cell line grown sufficiently in a 24-well plate, was washed with phosphate-buffered saline (PBS), and then was inoculated with influenza virus (A/PR8) of 14,000 plaque forming units (PFU) per well. It was cultured at 35° C. for 1 hour to infect the cells with the virus. After removing the culture medium and washing with phosphate-buffered saline, an RPMI culture medium containing 0.1 μg/ml TPCK-trypsin diluted to 11, 33, and 100 μM concentrations of each example compound was added to each well and cultured at 35° C.

In order to measure the amount of influenza virus present in the cell culture medium, each cell culture medium was collected after 2 days of culture, diluted 10-fold from 10-1 to 10-8, and infected with 100% grown MDCK cells in a 96-well plate. Three days after infection, cell activity was measured using MTT (Sigma), and a 50% endpoint was calculated using the Reed-Muench or Spearman-Karber method. This was expressed as TCID50/ml (tissue culture infective dose 50%), which is a unit expressed as a titer of the dilution factor at which the virus-inoculated cells were infected by 50%. The negative control group was infected with the virus but not treated with the example compound.

The results of the experiments above are shown in FIGS. 9 to 14.

Referring to FIGS. 9 to 14, it was identified that the compounds of the examples according to the present disclosure exhibited an effect (antiviral effect) of inhibiting cytotoxicity due to influenza virus infection.

<Experimental Example 16> Antiviral Effect Evaluation in Animal Models

In order to identify the inhibitory effect of the compound on influenza activity in an animal model, a mouse model infected with mouse-adapted PR8 (hereinafter referred to as "maPR8") virus was used. The model was established by infecting 7-week-old Balb/c mice with a virus corresponding to a titer of 3 $MLD_{50}$ (a mouse half lethal dose) through the nasal route. In order to observe the therapeutic effect, the compound of Example 4 was intraperitoneally administered one day before virus infection (day 0). During the period of animal experimentation, the experimental group (compound of Example 4) was administered once a day at a concentration of 10 mg/kg/day for 9 days. Three mice were used per group, and the antiviral efficacy was measured by weight measurement. Subjects whose body weight had decreased by 30% or more from the start of the experiment were euthanized (according to the regulations of the Animal Experimentation Committee of the Korea Research Institute of Chemical Technology) [Shin JS et al., (2017) J Microbiol. 55:979-983].

The results of the experiments above are shown in FIGS. 15 and 16.

Referring to FIGS. 15 and 16, it was identified that the animal group administered with the compound of the examples according to the present disclosure normalized the body weight of the influenza virus-infected mouse model and increased the survival rate.

The above description is merely illustrative of the present disclosure, and it would be understood by those skilled in the technical field to which the present disclosure pertains that the present disclosure may be implemented in a modified form without departing from the essential characteristics of the present disclosure. Therefore, the described examples and experimental examples should be considered in an illustrative rather than a restrictive perspective. The scope of the present disclosure is indicated in the claims rather than the foregoing description, and all differences within the equivalent scope thereof should be construed as being included in the present disclosure.

What is claimed is:

1. A compound selected from the group consisting of the following compounds, a stereoisomer thereof, a solvate thereof, a hydrate thereof, or a pharmaceutically acceptable salt thereof:

1) (S)-6-bromo-2-(2,5-dimethyl-1-(4-morpholinophenyl)-1H-pyrrol-3-yl)-N-(1-(ethylsulfonyl) pyrrolidine-3-yl)-3H-imidazo[4,5-b]pyridine-7-amine;

2) (S)-6-bromo-2-(2,5-dimethyl-1-(3-morpholinophenyl)-1H-pyrrol-3-yl)-N-(1-(ethylsulfonyl) pyrrolidine-3-yl)-3H-imidazo[4,5-b]pyridine-7-amine;

3) (S)-6-bromo-2-(2,5-dimethyl-1-(3-(2-morpholinoethoxy)phenyl)-1H-pyrrol-3-yl)-N-(1-(ethylsulfonyl) pyrrolidine-3-yl)-1H-imidazo[4,5-b]pyridine-7-amine;

4) (S)-6-bromo-2-(2,5-dimethyl-1-(4-(2-morpholinoethoxy)phenyl)-1H-pyrrol-3-yl)-N-(1-(ethylsulfonyl) pyrrolidine-3-yl)-1H-imidazo[4,5-b]pyridine-7-amine;

5) (S)-(4-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)phenyl) (morpholino) methanone;

6) (S)-(3-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)phenyl) (morpholino) methanone;

7) N-(3-(3-(6-bromo-7-(((S)-1-(ethylsulfonyl) pyrrolidine-3-yl)amino)-3H-imidazo[4,5-b]pyridine-2-yl)-2,5-dimethyl-1H-pyrrol-1-yl)-4-methylphenyl) methanesulfonamide;

8) N-(4-(3-(6-bromo-7-(((S)-1-(ethylsulfonyl) pyrrolidine-3-yl)amino)-3H-imidazo[4,5-b]pyridine-2-yl)-2,5-dimethyl-1H-pyrrol-1-yl)-3-methylphenyl) methanesulfonamide;

9) N-(3-(3-(6-bromo-7-(((S)-1-(ethylsulfonyl) pyrrolidine-3-yl)amino)-3H-imidazo[4,5-b]pyridine-2-yl)-2,5-dimethyl-1H-pyrrol-1-yl)-2-methylphenyl) methanesulfonamide;

10) (S)-6-bromo-2-(2,5-dimethyl-1-(4-(morpholinosulfonyl)phenyl)-1H-pyrrol-3-yl)-N-(1-(ethylsulfonyl) pyrrolidine-3-yl)-3H-imidazo[4,5-b]pyridine-7-amine;

11) (S)-6-bromo-2-(2,5-dimethyl-1-(3-(morpholinosulfonyl)phenyl)-1H-pyrrol-3-yl)-N-(1-(ethylsulfonyl) pyrrolidine-3-yl)-3H-imidazo[4,5-b]pyridine-7-amine;

12) (S)—N-(3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)phenyl) methanesulfonamide;

13) (S)-6-bromo-2-(1-(2,6-dichlorophenyl)-2,5-dimethyl-1H-pyrrol-3-yl)-N-(1-(ethylsulfonyl) pyrrolidine-3-yl)-3H-imidazo[4,5-b]pyridine-7-amine;

14) 6-bromo-2-(1-(2,5-dichlorophenyl)-2,5-dimethyl-1H-pyrrol-3-yl)-N—((S)-1-(ethylsulfonyl) pyrrolidine-3-yl)-3H-imidazo[4,5-b]pyridine-7-amine;

15) (S)-6-bromo-2-(1-(3,4-dichlorophenyl)-2,5-dimethyl-1H-pyrrol-3-yl)-N-(1-(ethylsulfonyl) pyrrolidine-3-yl)-3H-imidazo[4,5-b]pyridine-7-amine;

16) 6-bromo-2-(1-(2-chlorophenyl)-2,5-dimethyl-1H-pyrrol-3-yl)-N—((S)-1-(ethylsulfonyl) pyrrolidine-3-yl)-3H-imidazo[4,5-b]pyridine-7-amine;

17) 3-(3-(6-bromo-7-(((S)-1-(ethylsulfonyl) pyrrolidine-3-yl)amino)-3H-imidazo[4,5-b]pyridine-2-yl)-2,5-dimethyl-1H-pyrrol-1-yl)-4-chlorobenzenesulfonamide;

18) (S)-3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)-N-methylbenzenesulfonamide;

19) (S)-3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)-N-ethylbenzenesulfonamide;

20) (S)-3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)benzamide;

21) (S)-6-bromo-N-(1-(ethylsulfonyl) pyrrolidine-3-yl)-2-(1-(3-(2-methoxyethoxy)phenyl)-2,5-dimethyl-1H-pyrrol-3-yl)-1H-imidazo[4,5-b]pyridine-7-amine;

22) (S)-6-bromo-N-(1-(ethylsulfonyl) pyrrolidine-3-yl)-2-(1-(4-(2-methoxyethoxy)phenyl)-2,5-dimethyl-1H-pyrrol-3-yl)-1H-imidazo[4,5-b]pyridine-7-amine;

23) (S)-3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)benzenesulfonamide;

24) (S)-4-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)benzenesulfonamide;

25) (S)-6-bromo-2-(2,5-dimethyl-1-phenyl-1H-pyrrol-3-yl)-N-(1-(ethylsulfonyl) pyrrolidine-3-yl)-3H-imidazo [4,5-b]pyridine-7-amine;

26) 3-((6-bromo-2-(1-(2,6-dichlorophenyl)-2,5-dimethyl-1H-pyrrol-3-yl)-3H-imidazo[4,5-b]pyridine-7-yl) amino)benzenesulfonamide;

27) 3-((6-bromo-2-(2,5-dimethyl-1-(4-(morpholine-4-carbonyl)phenyl)-1H-pyrrol-3-yl)-3H-imidazo[4,5-b] pyridine-7-yl)amino)benzenesulfonamide;

28) 3-((6-bromo-2-(2,5-dimethyl-1-(3-(morpholine-4-carbonyl)phenyl)-1H-pyrrol-3-yl)-3H-imidazo[4,5-b] pyridine-7-yl)amino)benzenesulfonamide;

29) 3-((6-bromo-2-(2,5-dimethyl-1-(4-(morpholinosulfonyl)phenyl)-1H-pyrrol-3-yl)-3H-imidazo[4,5-b]pyridine-7-yl)amino)benzenesulfonamide;

30) 3-((6-bromo-2-(2,5-dimethyl-1-(3-(morpholinosulfonyl)phenyl)-1H-pyrrol-3-yl)-3H-imidazo[4,5-b]pyridine-7-yl)amino)benzenesulfonamide;

31) 3-((6-bromo-2-(1-(2-chlorophenyl)-2,5-dimethyl-1H-pyrrol-3-yl)-3H-imidazo[4,5-b]pyridine-7-yl)amino) benzenesulfonamide;

32) 3-((6-bromo-2-(2,5-dimethyl-1-(2-methyl-4-(methylsulfonamido)phenyl)-1H-pyrrol-3-yl)-3H-imidazo[4,5-b]pyridine-7-yl)amino)benzenesulfonamide;

33) 3-((6-bromo-2-(2,5-dimethyl-1-(2-methyl-5-(methylsulfonamido)phenyl)-1H-pyrrol-3-yl)-3H-imidazo[4,5-b]pyridine-7-yl)amino)benzenesulfonamide;

34) 3-((6-bromo-2-(2,5-dimethyl-1-(2-methyl-3-(methylsulfonamido)phenyl)-1H-pyrrol-3-yl)-3H-imidazo[4,5-b]pyridine-7-yl)amino)benzenesulfonamide;

35) 3-((6-bromo-2-(1-(2,5-dichlorophenyl)-2,5-dimethyl-1H-pyrrol-3-yl)-3H-imidazo[4,5-b]pyridine-7-yl) amino)benzenesulfonamide;

36) 3-(3-(6-bromo-7-((3-sulfamoylphenyl)amino)-3H-imidazo[4,5-b]pyridine-2-yl)-2,5-dimethyl-1H-pyrrole-1-yl)-4-chlorobenzenesulfonamide;

37) 3-((6-bromo-2-(2,5-dimethyl-1-(3-morpholinophenyl)-1H-pyrrol-3-yl)-3H-imidazo[4,5-b]pyridine-7-yl) amino)benzenesulfonamide;

38) 3-((6-bromo-2-(2,5-dimethyl-1-(3-(2-morpholinoethoxy)phenyl)-1H-pyrrol-3-yl)-1H-imidazo[4,5-b]pyridine-7-yl)amino)benzenesulfonamide;

39) 3-((6-bromo-2-(2,5-dimethyl-1-(4-(2-morpholinoethoxy)phenyl)-1H-pyrrol-3-yl)-1H-imidazo[4,5-b]pyridine-7-yl)amino)benzenesulfonamide;

40) 3-((6-bromo-2-(2,5-dimethyl-1-(4-morpholinophenyl)-1H-pyrrol-3-yl)-3H-imidazo[4,5-b]pyridine-7-yl) amino)benzenesulfonamide;

41) 3-((2-(1-(benzo[d][1,3]dioxole-5-yl)-2,5-dimethyl-1H-pyrrol-3-yl)-6-bromo-3H-imidazo[4,5-b]pyridine-7-yl)amino)benzenesulfonamide;

42) 3-((6-bromo-2-(1-(3-(2-methoxyethoxy)phenyl)-2,5-dimethyl-1H-pyrrol-3-yl)-1H-imidazo[4,5-b]pyridine-7-yl)amino)benzenesulfonamide;

43) 3-((6-bromo-2-(2,5-dimethyl-1-phenyl-1H-pyrrol-3-yl)-1H-imidazo[4,5-b]pyridine-7-yl)amino)benzenesulfonamide;

44) 3-(3-(7-(benzo[d][1,3]dioxole-5-yl-amino)-6-bromo-3H-imidazo[4,5-b]pyridine-2-yl)-2,5-dimethyl-1H-pyrrol-1-yl)benzenesulfonamide;

45) 2-(1-(benzo[d][1,3]dioxole-5-yl)-2,5-dimethyl-1H-pyrrol-3-yl)-6-bromo-N-(4-(2-methoxyethoxy)phenyl)-3H-imidazo[4,5-b]pyridine-7-amine;

46) 3-(3-(6-bromo-7-((4-(2-methoxyethoxy)phenyl)amino)-3H-imidazo[4,5-b]pyridine-2-yl)-2,5-dimethyl-1H-pyrrol-1-yl)benzenesulfonamide;

47) 3-((6-bromo-2-(2,5-dimethyl-1-(pyridine-3-yl)-1H-pyrrol-3-yl)-1H-imidazo[4,5-b]pyridine-7-yl)amino)benzenesulfonamide;

48) 3-((6-bromo-2-(2,5-dimethyl-1-(pyridine-4-ylmethyl)-1H-pyrrol-3-yl)-1H-imidazo[4,5-b]pyridine-7-yl)amino)benzenesulfonamide;

49) (S)-2-(1-(benzo[d][1,3]dioxole-5-yl)-2,5-dimethyl-1H-pyrrol-3-yl)-6-bromo-N-(1-(ethylsulfonyl) pyrrolidine-3-yl)-3H-imidazo[4,5-b]pyridine-7-amine;

50) N-(3-(3-(7-(((S)-1-(ethylsulfonyl) pyrrolidine-3-yl)amino)-3H-imidazo[4,5-b]pyridine-2-yl)-2,5-dimethyl-1H-pyrrol-1-yl)-4-methylphenyl) methanesulfonamide;

51) N-(3-(3-(6-chloro-7-(((S)-1-(ethylsulfonyl) pyrrolidine-3-yl)amino)-3H-imidazo[4,5-b]pyridine-2-yl)-2,5-dimethyl-1H-pyrrol-1-yl)-4-methylphenyl) methanesulfonamide;

52) (S)-6-chloro-2-(2,5-dimethyl-1-(4-(2-morpholinoethoxy)phenyl)-1H-pyrrol-3-yl)-N-(1-(ethylsulfonyl) pyrrolidine-3-yl)-1H-imidazo[4,5-b]pyridine-7-amine;

53) (S)-2-(2,5-dimethyl-1-(4-(2-morpholinoethoxy)phenyl)-1H-pyrrol-3-yl)-N-(1-(ethylsulfonyl) pyrrolidine-3-yl)-1H-imidazo[4,5-b]pyridine-7-amine;

54) (S)-(3-(3-(6-chloro-7-((1-(ethylsulfonyl) pyrrolidine-3-yl)amino)-1H-imidazo[4,5-b]pyridine-2-yl)-2,5-dimethyl-1H-pyrrol-1-yl)phenyl) (morpholino) methanone;

55) (S)-(3-(3-(7-((1-(ethylsulfonyl) pyrrolidine-3-yl)amino)-3H-imidazo[4,5-b]pyridine-2-yl)-2,5-dimethyl-1H-pyrrol-1-yl)phenyl) (morpholino) methanone;

56) (S)-3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)-N-(2-(diethylamino)ethyl)benzamide;

57) (S)-4-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)-N-(2-(diethylamino)ethyl)benzamide;

58) (S)-3-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)benzoic acid;

59) (S)-4-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)benzoic acid;

60) (S)-3-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)-N-((dimethylamino)methyl) benzamide;

61) (S)-3-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)-N-(2-(dimethylamino)ethyl)-N-methylbenzamide;

62) (S)-4-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)-N-(2-(dimethylamino)ethyl) benzamide;

63) (S)-4-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)-N-(2-(dimethylamino)ethyl)-N-methylbenzamide;

64) (S)—N-(3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)phenyl)-2-(dimethylamino) acetamide;

65) (S)—N-(3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)phenyl)-2-(4-methylpiperazine-1-yl) acetamide;

66) (S)—N-(3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)phenyl)-2-morpholinoacetamide;

67) (S)-(4-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)phenyl) (4-methylpiperazine-1-yl) methanone;

68) (S)-(3-(3-(6-bromo-7-((1-(ethylsulfonyl) pyrrolidine-3-yl)amino)-1H-imidazo[4,5-b]pyridine-2-yl)-2,5-dimethyl-1H-pyrrol-1-yl)phenyl) (4-methylpiperazine-1-yl) methanone;

69) (S)-3-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)-N-(2-morpholinoethyl)benzamide;

70) (S)-4-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)-N-(2-morpholinoethyl)benzamide;

71) (S)-3-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)-N-(2-(4-methylpiperazine-1-yl)ethyl)benzamide;

72) (S)-4-(3-(6-bromo-7-((1-(ethylsulfonyl) pyrrolidine-3-yl)amino)-3H-imidazo[4,5-b]pyridine-2-yl)-2,5-dimethyl-1H-pyrrol-1-yl)-N-(2-(4-methylpiperazine-1-yl)ethyl)benzamide;

73) N-(4-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-3-methylphenyl)-2-(dimethylamino) acetamide;

74) N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-4-methylphenyl)-2-(dimethylamino) acetamide;

75) N-(4-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-3-methylphenyl)-2-(4-methylpiperazine-1-yl) acetamide;

76) N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-4-methylphenyl)-2-(4-methylpiperazine-1-yl) acetamide;

77) N-(4-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-3-methylphenyl)-2-morpholinoacetamide;

78) N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-4-methylphenyl)-2-morpholinoacetamide;

79) N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-2-methylphenyl)-3-(dimethylamino) propanamide;

80) N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-4-methylphenyl)-3-(dimethylamino) propanamide;

81) (3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-2-methylphenyl) (4-methylpiperazine-1-yl) methanone;

82) 3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-N-(2-(dimethylamino)ethyl)-2-methylbenzamide;

83) (3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-2-methylphenyl) (morpholino) methanone;

84) N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-2-methylphenyl)-2-(dimethylamino) acetamide;

85) N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-2-methylphenyl)-2-morpholinoacetamide;

86) N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-2-methylphenyl)-3-(dimethylamino) propanamide;

87) N-(3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-2-methylphenyl)-2-(4-methylpiperazine-1-yl) acetamide;

88) N-(3-(3-(6-bromo-7-((3-sulfamoylphenyl)amino)-1H-imidazo[4,5-b]pyridine-2-yl)-2,5-dimethyl-1H-pyrrol-1-yl)-4-methylphenyl)-2-morpholinoacetamide;

89) N-(3-(3-(6-bromo-7-((3-sulfamoylphenyl)amino)-1H-imidazo[4,5-b]pyridine-2-yl)-2,5-dimethyl-1H-pyrrol-1-yl)-4-methylphenyl)-2-(4-methylpiperazine-1-yl) acetamide;

90) N-(3-(3-(6-bromo-7-((3-sulfamoylphenyl)amino)-1H-imidazo[4,5-b]pyridine-2-yl)-2,5-dimethyl-1H-pyrrol-1-yl)-4-methylphenyl)-2-(dimethylamino) acetamide;

91) (3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-4-methylphenyl) (morpholino) methanone;

92) (3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-4-methylphenyl) (4-methylpiperazine-1-yl) methanone;

93) 3-(3-(6-bromo-7-(((S)-1-(ethylsulfonyl) pyrrolidine-3-yl)amino)-1H-imidazo[4,5-b]pyridine-2-yl)-2,5-dimethyl-1H-pyrrol-1-yl)-N-(2-(dimethylamino)ethyl)-4-methylbenzamide;

94) 3-((6-bromo-2-(2,5-dimethyl-1-(2-methyl-5-(morpholine-4-carbonyl)phenyl)-1H-pyrrol-3-yl)-1H-imidazo[4,5-b]pyridine-7-yl)amino)benzenesulfonamide;

95) 3-((6-bromo-2-(2,5-dimethyl-1-(2-methyl-5-(4-methylpiperazine-1-carbonyl)phenyl)-1H-pyrrol-3-yl)-1H-imidazo[4,5-b]pyridine-7-yl)amino)benzenesulfonamide;

96) 3-(3-(6-bromo-7-((3-sulfamoylphenyl)amino)-1H-imidazo[4,5-b]pyridine-2-yl)-2,5-dimethyl-1H-pyrrol-1-yl)-N-(2-(dimethylamino)ethyl)-4-methylbenzamide;

97) (4-(3-(6-bromo-7-(((S)-1-(ethylsulfonyl) pyrrolidine-3-yl)amino)-3H-imidazo[4,5-b]pyridine-2-yl)-2,5-dimethyl-1H-pyrrol-1-yl)-3-methylphenyl) (4-methylpiperazine-1-yl) methanone;

98) (4-(3-(6-bromo-7-(((S)-1-(ethylsulfonyl) pyrrolidine-3-yl)amino)-3H-imidazo[4,5-b]pyridine-2-yl)-2,5-dimethyl-1H-pyrrol-1-yl)-3-methylphenyl) (morpholino) methanone.

2. A pharmaceutical composition comprising the compound represented by Formula claim 1, a stereoisomer thereof, a solvate thereof, a hydrate thereof, or a pharmaceutically acceptable salt thereof as an active ingredient.

3. The pharmaceutical composition of claim 2, wherein the compound inhibits protein kinase activity.

4. The pharmaceutical composition of claim 3, wherein the protein kinase is at least one selected from the group consisting of MLK1, MLK2, MLK3, MLK4, DLK, LZK, ZAK and LRRK2.

* * * * *